(12) United States Patent
Glovinsky et al.

(10) Patent No.: US 8,834,368 B2
(45) Date of Patent: Sep. 16, 2014

(54) GOLDMANN APPLANATION TONOMETER, BIOMICROSCOPY DEVICE AND RELATED METHODS

(76) Inventors: Yosef Glovinsky, Petach Tikva (IL); Vadim Shmukler, Rishon Lezion (IL); Ilia Piven, Ramat Gan (IL)

(*) Notice: Subject to any disclaimer, the term of this patent is extended or adjusted under 35 U.S.C. 154(b) by 0 days.

(21) Appl. No.: 13/595,538

(22) Filed: Aug. 27, 2012

(65) Prior Publication Data
US 2013/0085369 A1    Apr. 4, 2013

Related U.S. Application Data

(63) Continuation-in-part of application No. 13/037,355, filed on Feb. 28, 2011, and a continuation-in-part of application No. PCT/US2011/026561, filed on Feb. 28, 2011.

(60) Provisional application No. 61/414,423, filed on Nov. 17, 2010, provisional application No. 61/319,117, filed on Mar. 30, 2010, provisional application No. 61/308,339, filed on Feb. 26, 2010.

(51) Int. Cl.
*A61B 3/16* (2006.01)
*A61B 3/13* (2006.01)
*A61B 3/135* (2006.01)

(52) U.S. Cl.
USPC ............................. 600/405; 600/399; 351/245

(58) Field of Classification Search
USPC .................................... 600/399, 405; 351/245
See application file for complete search history.

(56) References Cited

U.S. PATENT DOCUMENTS

| | | | |
|---|---|---|---|
| 2,235,319 A | | 3/1941 | Jobe |
| 3,070,997 A | | 1/1963 | Papritz et al. |
| 3,944,342 A | | 3/1976 | Martinez |
| 4,175,839 A | | 11/1979 | Muller et al. |
| 4,508,121 A | * | 4/1985 | Myers ........................ 600/382 |
| 4,735,209 A | | 4/1988 | Foody |
| 5,000,563 A | * | 3/1991 | Gisel et al. ................... 351/245 |
| 5,363,155 A | | 11/1994 | Urinowski et al. |
| 5,471,260 A | * | 11/1995 | Luce et al. .................... 351/245 |
| 5,488,443 A | | 1/1996 | Ota et al. |
| 6,072,623 A | | 6/2000 | Kitajima et al. |
| 6,083,160 A | | 7/2000 | Lipman |
| 7,329,003 B2 | * | 2/2008 | Nicolini ....................... 351/245 |
| 2011/0275923 A1 | | 11/2011 | Glovinsky et al. |

FOREIGN PATENT DOCUMENTS

| | | | | |
|---|---|---|---|---|
| DE | 2005004642 | | 8/2006 | |
| JP | 2003235803 | | 8/2003 | |
| WO | WO2006044056 | * | 4/2006 | ............ A61B 3/13 |
| WO | WO 2006044056 A2 | * | 4/2006 | ............ A61B 3/13 |

* cited by examiner

*Primary Examiner* — Rene Towa
*Assistant Examiner* — Emily Lloyd
(74) *Attorney, Agent, or Firm* — Marc Van Dyke; 4th Dimension IP

(57) ABSTRACT

Apparatus and methods for subjecting a patient to an slit lamp microscopy and/or Goldmann tonometry eye examination are disclosed herein. In some embodiments, the patient is in a side-lying down position at a time of the examination. In some embodiments, it is possible to examine an upper and/or lower eye—for example, a lower eye slightly above a supporting surface. Related apparatus are disclosed herein. In some embodiments, the apparatus includes a bed and/or a headrest and/or a face immobilization assembly are disclosed herein.

10 Claims, 64 Drawing Sheets

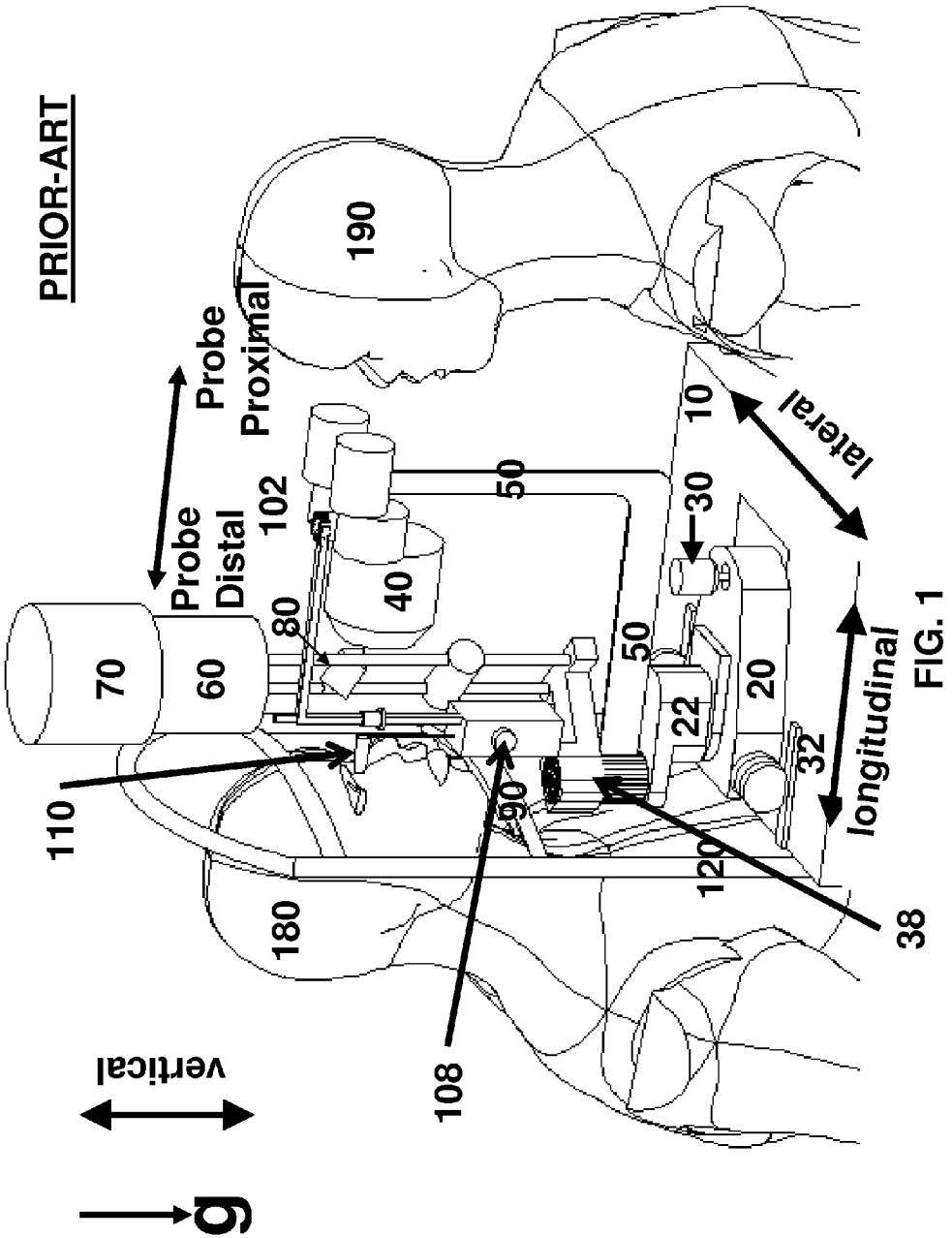

PRIOR-ART

Portable Applanation Tonometer (Perkins)

Portable Applanation Tonometer (Perkins)
PRIOR-ART

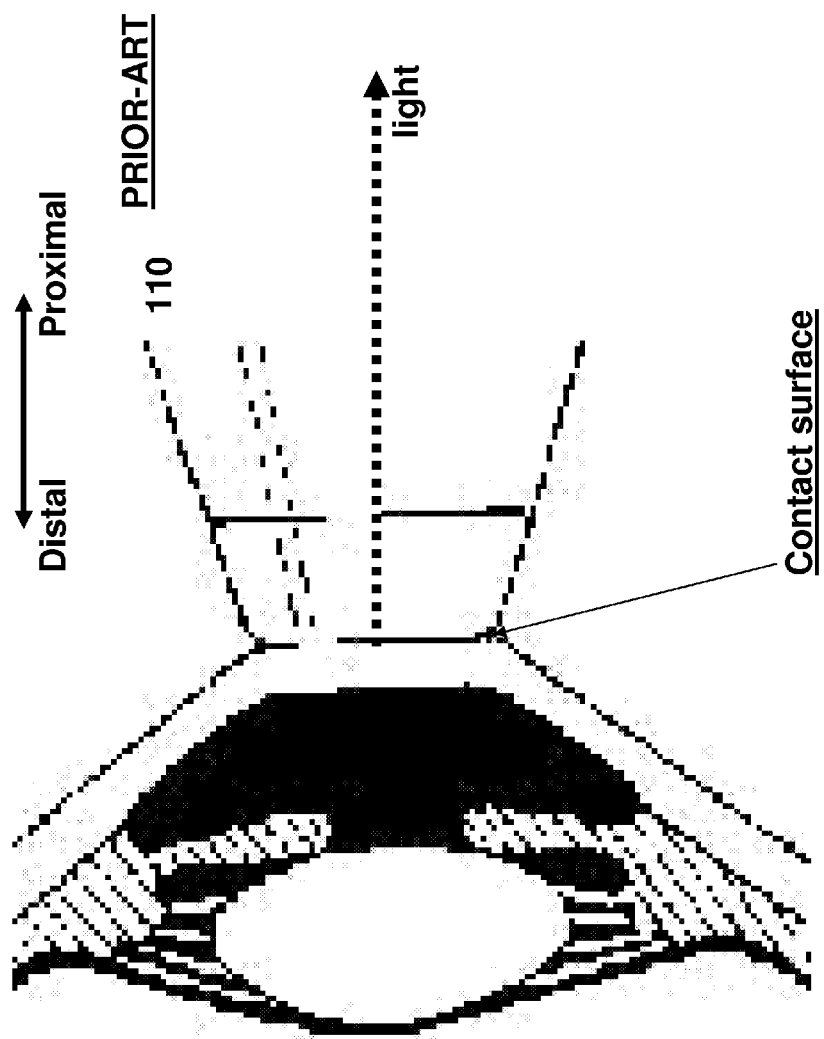

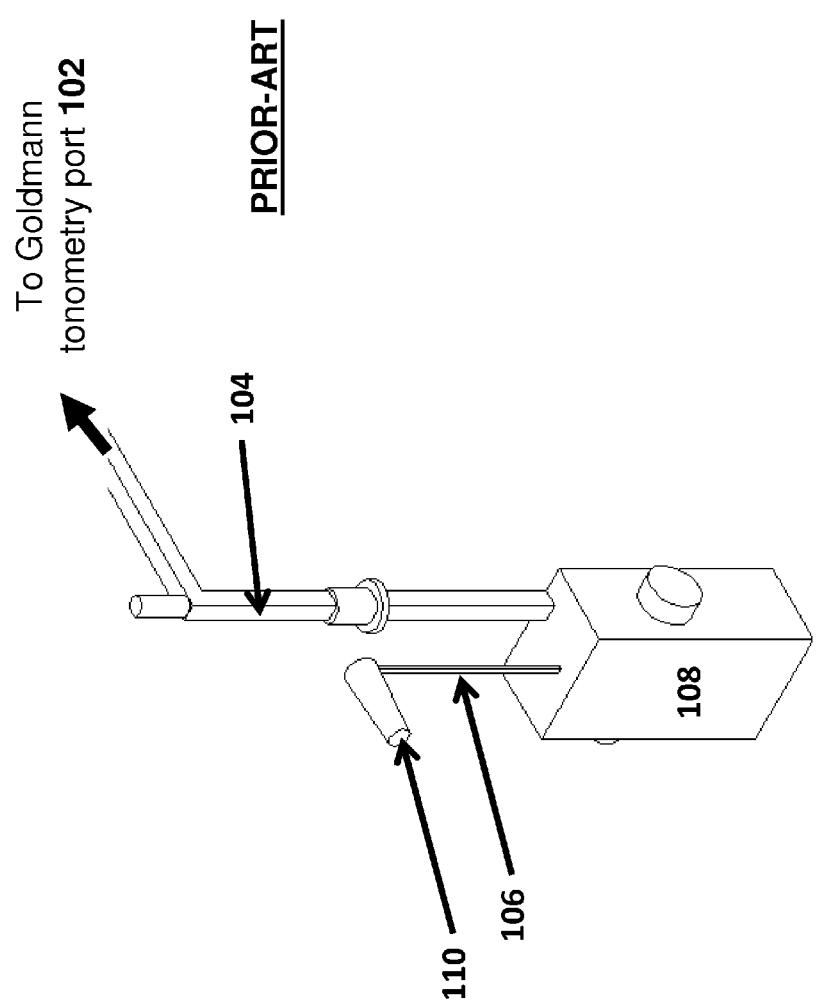
FIG. 5B  PRIOR-ART

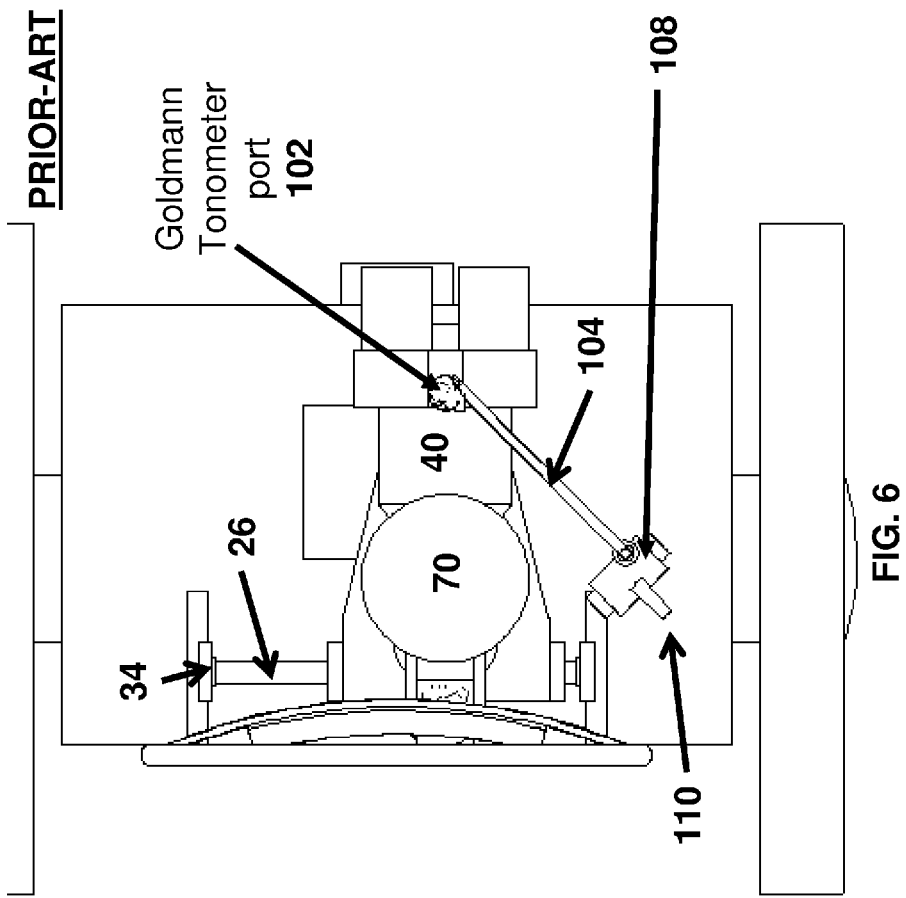

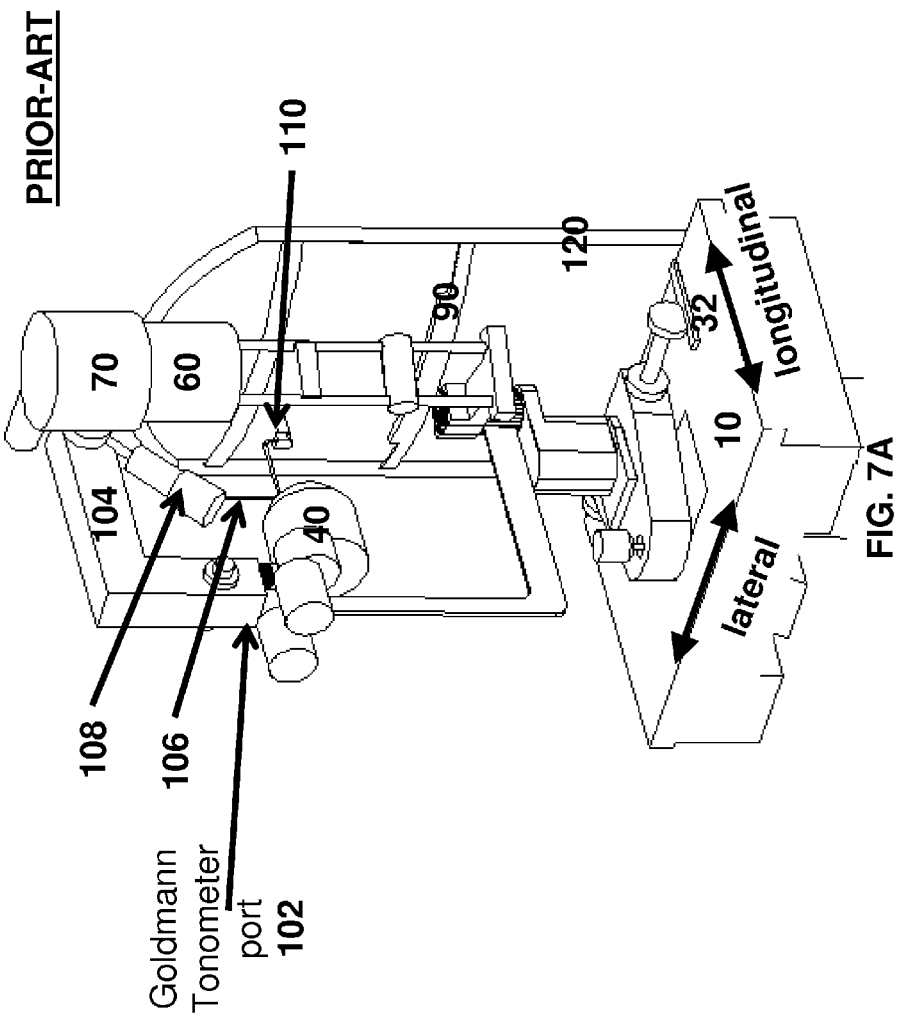

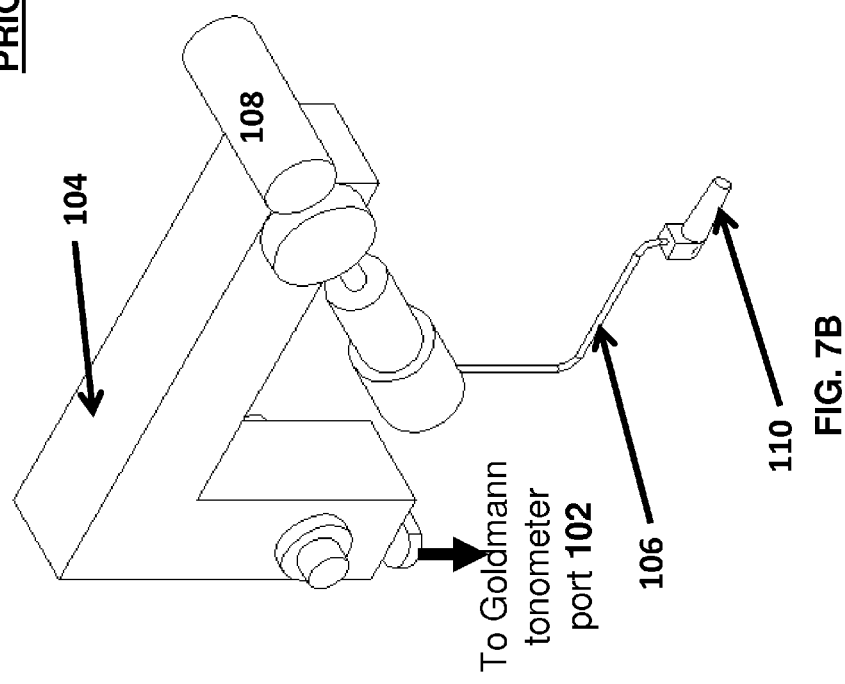

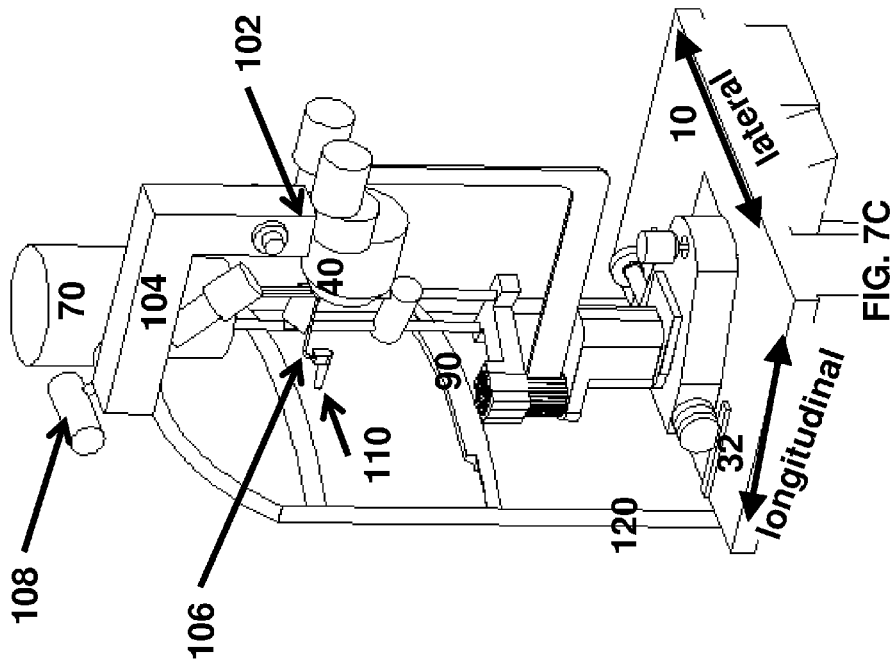
FIG. 7C PRIOR-ART

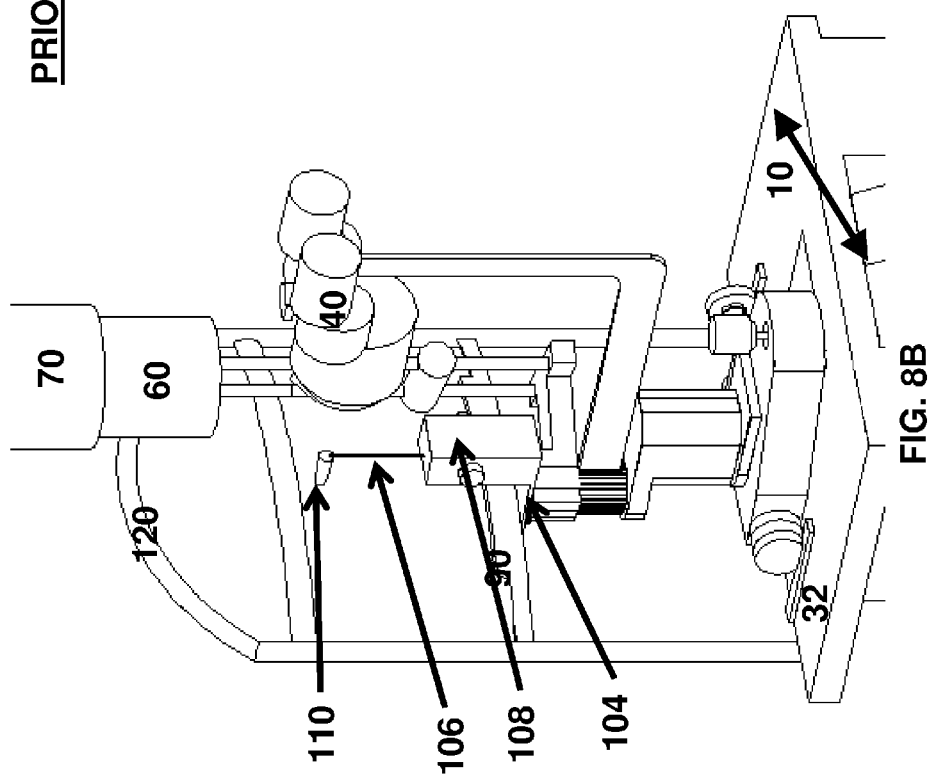

PRIOR-ART

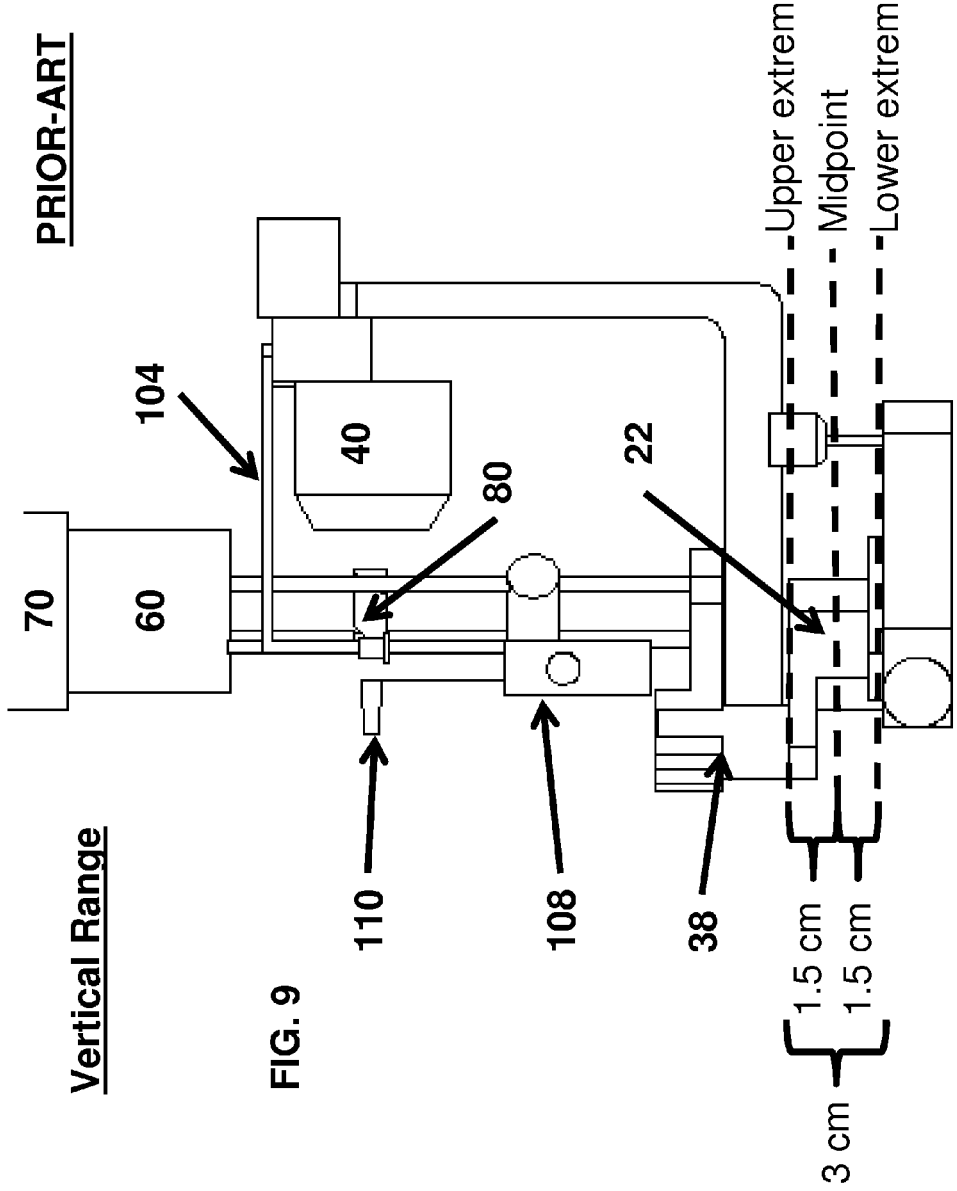

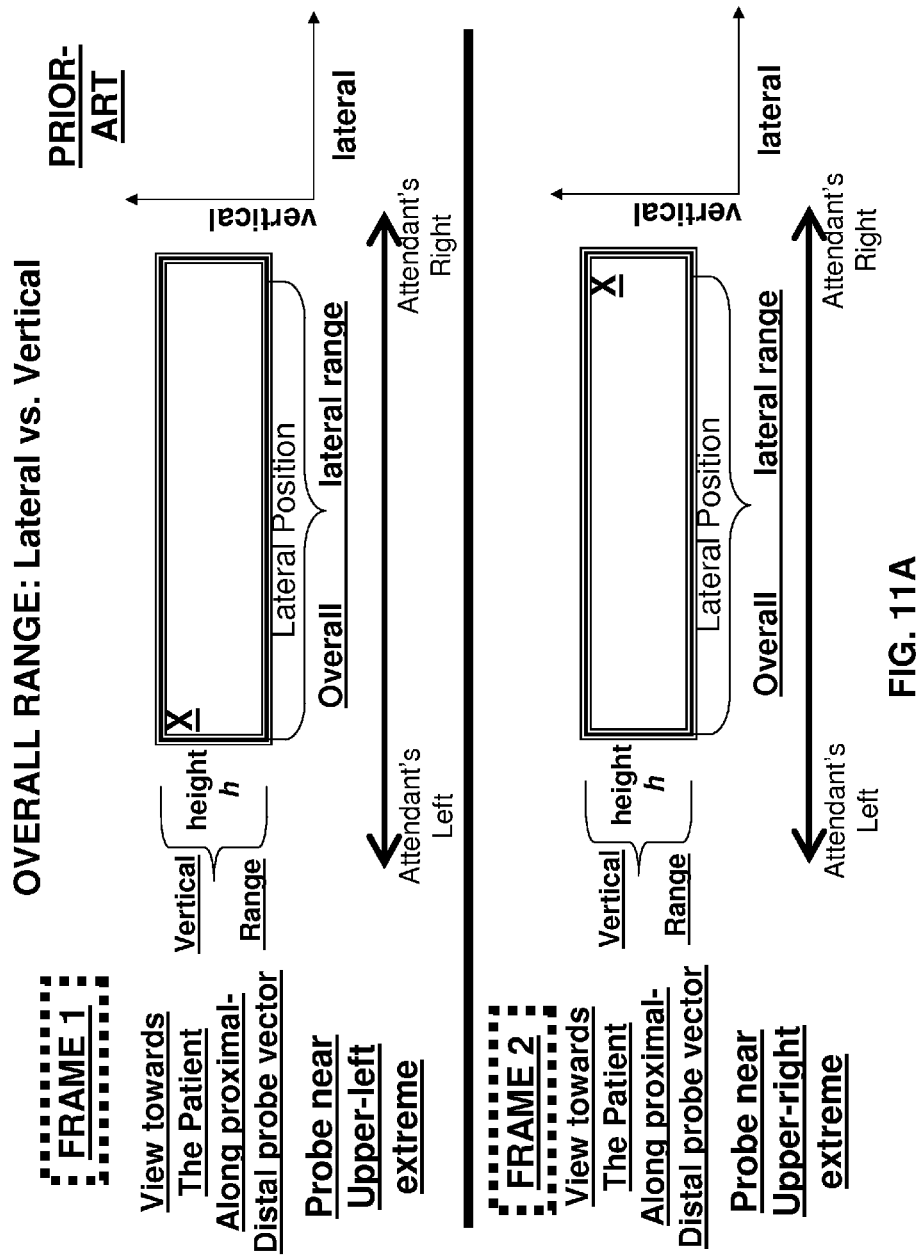

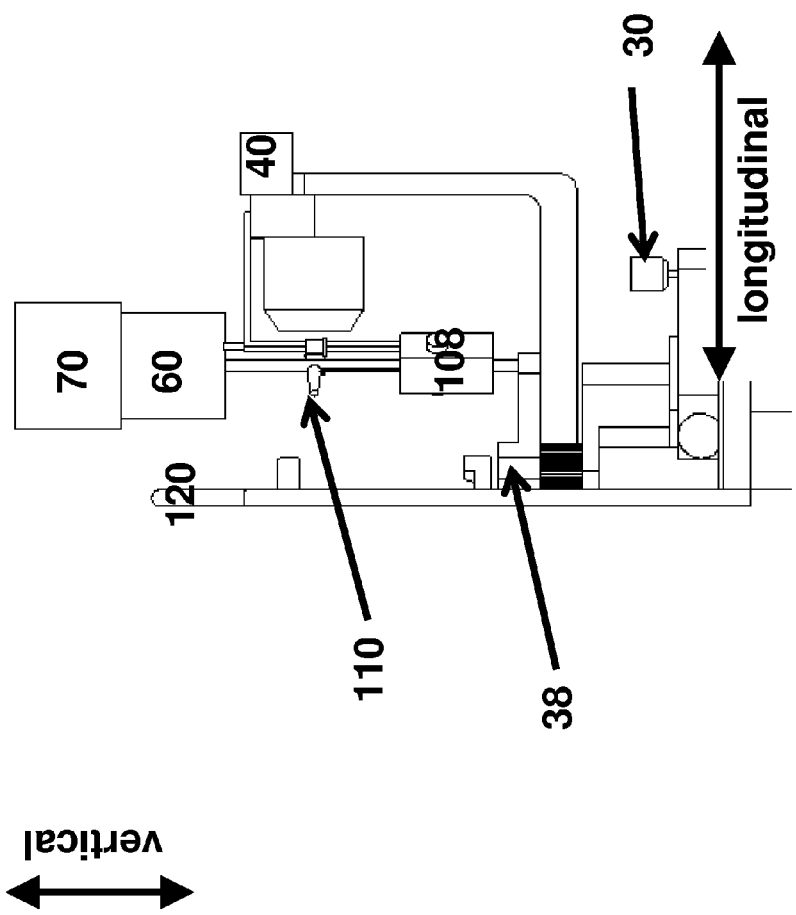
FIG. 14A  PRIOR-ART

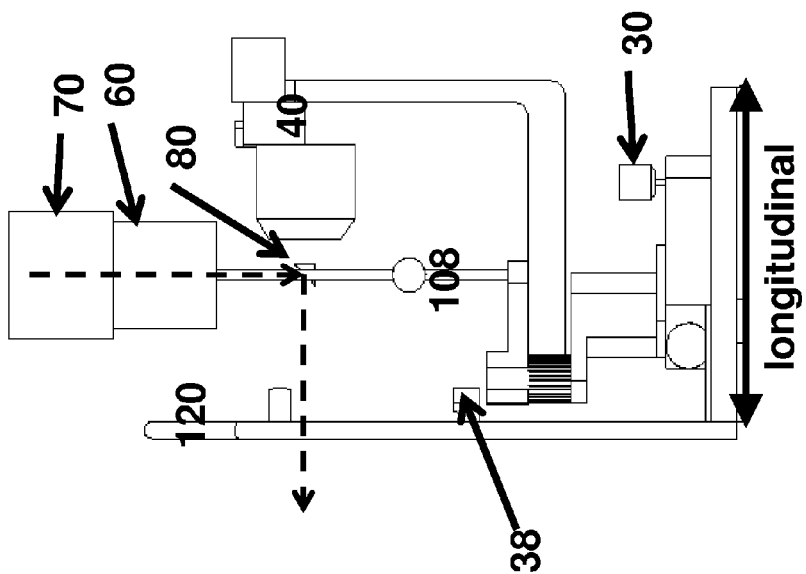

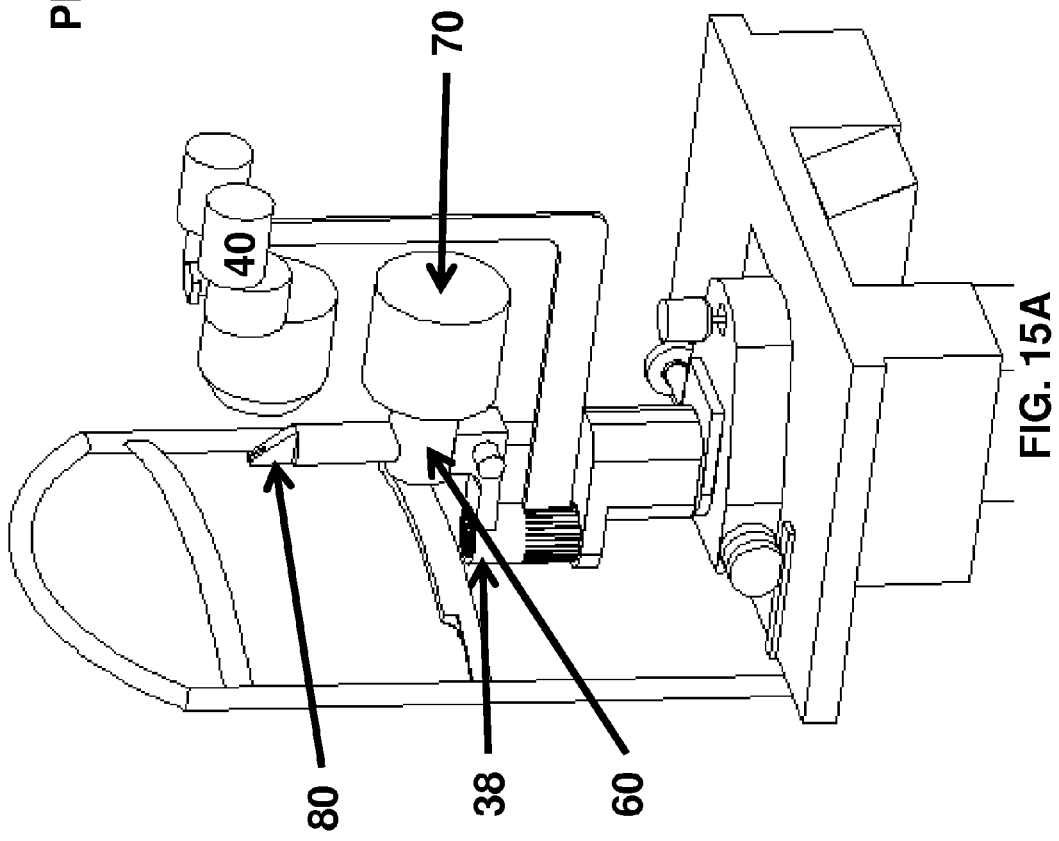

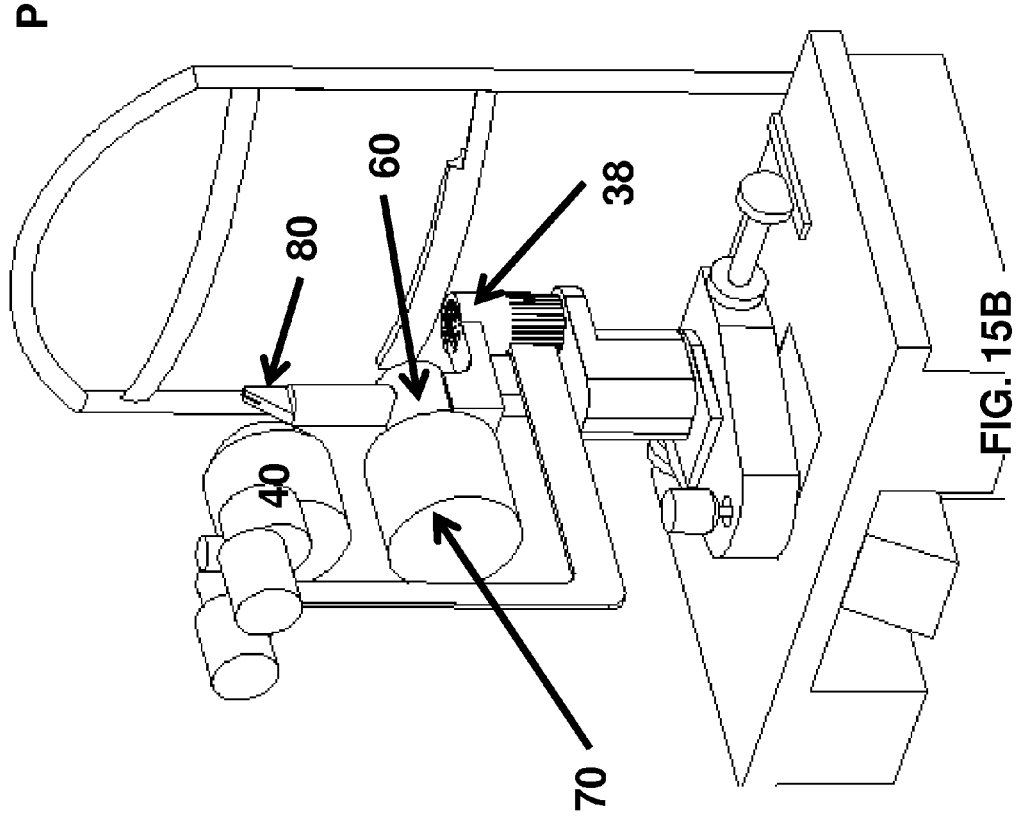

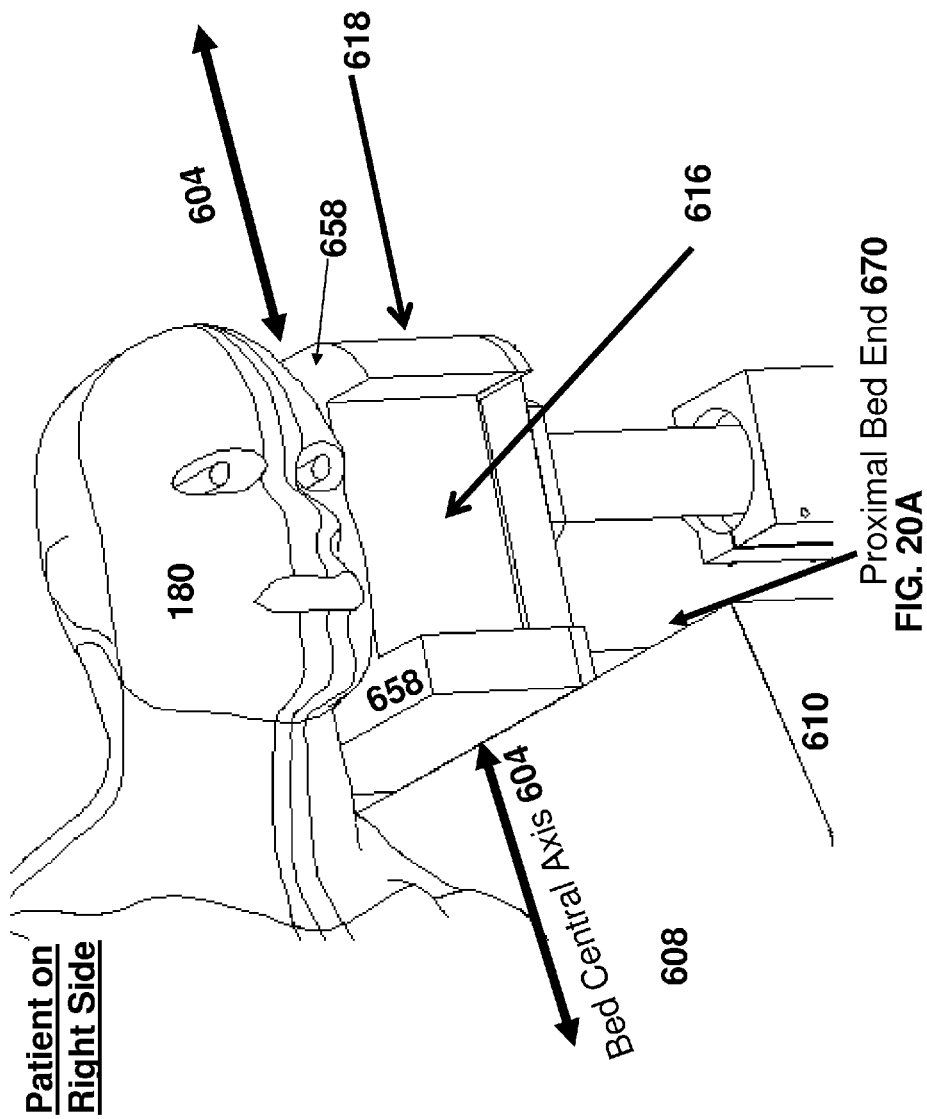

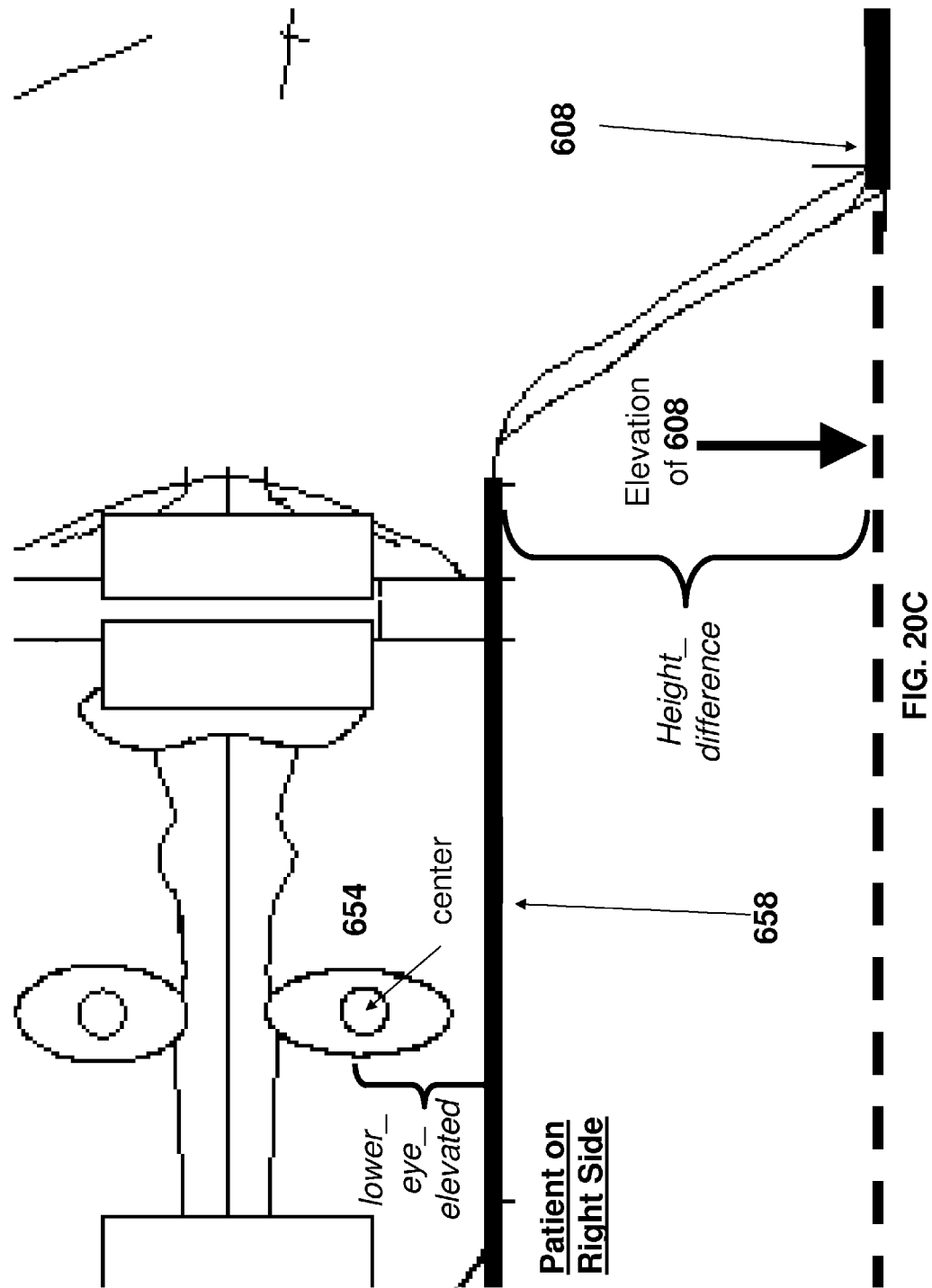

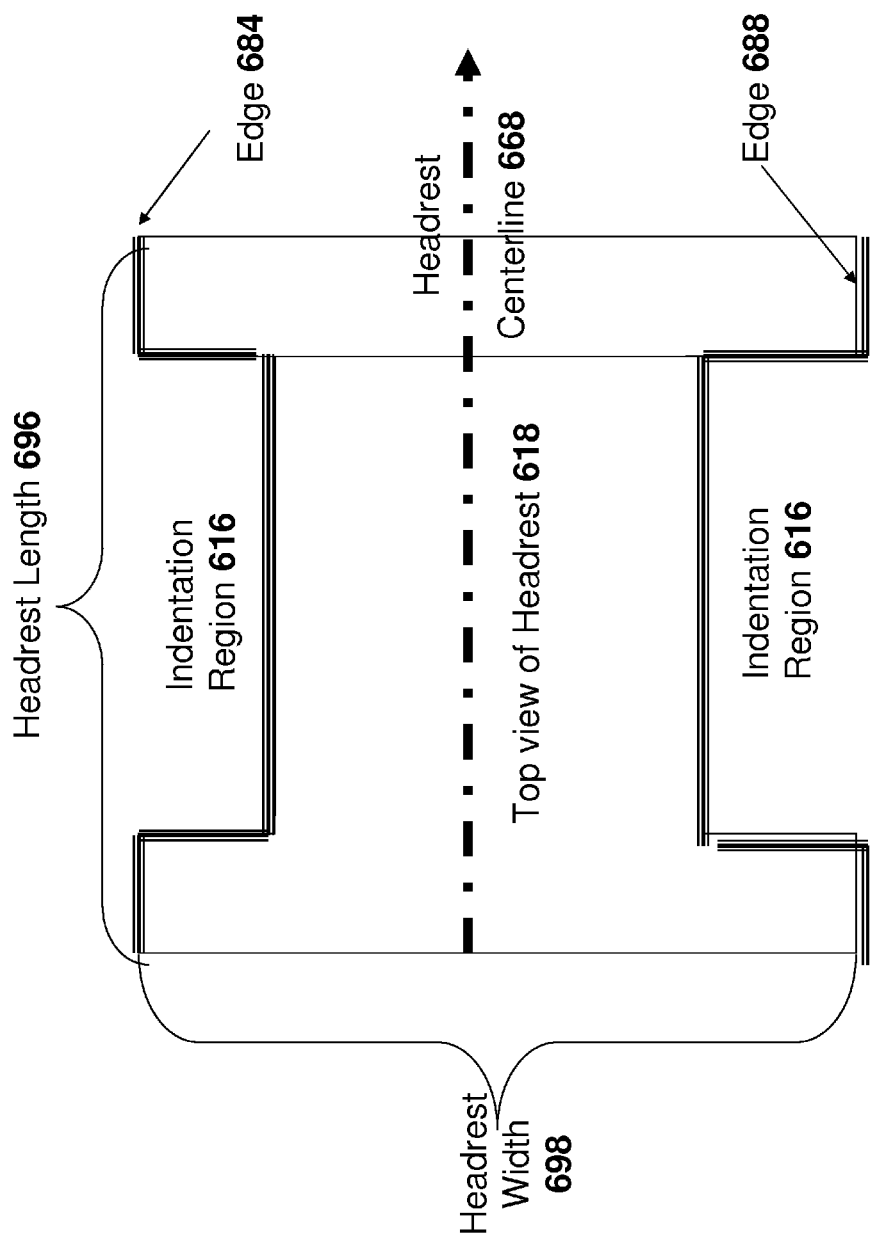

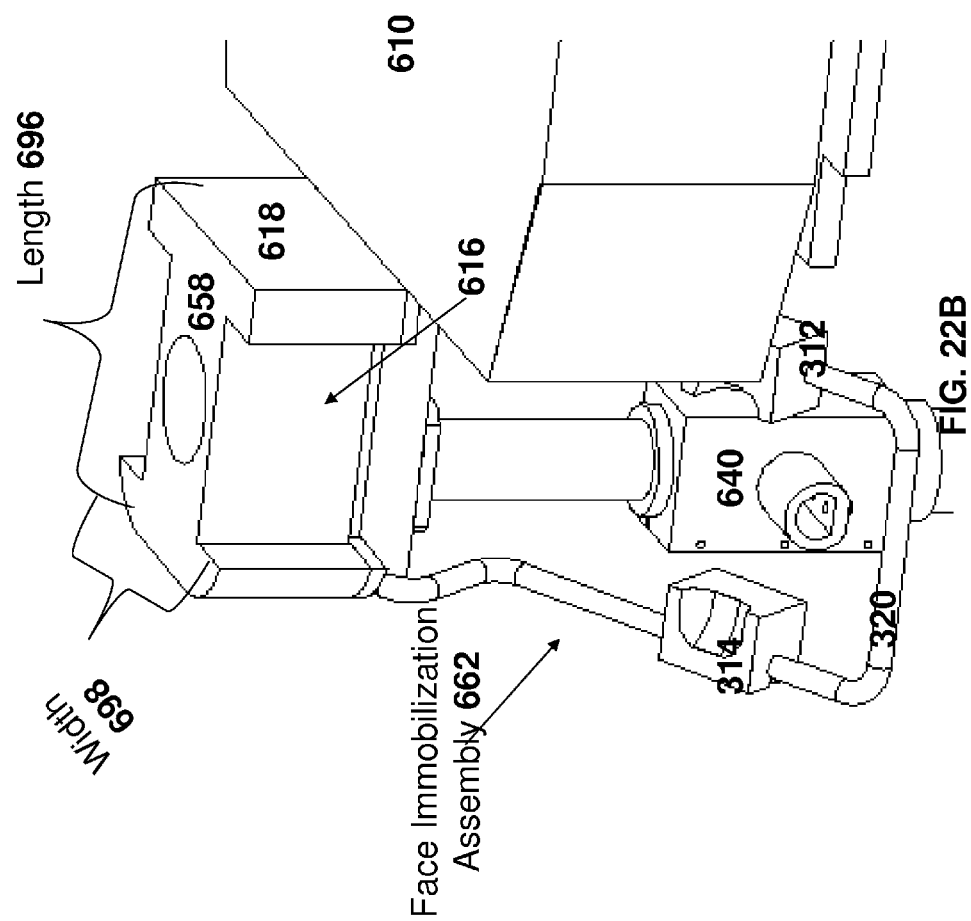

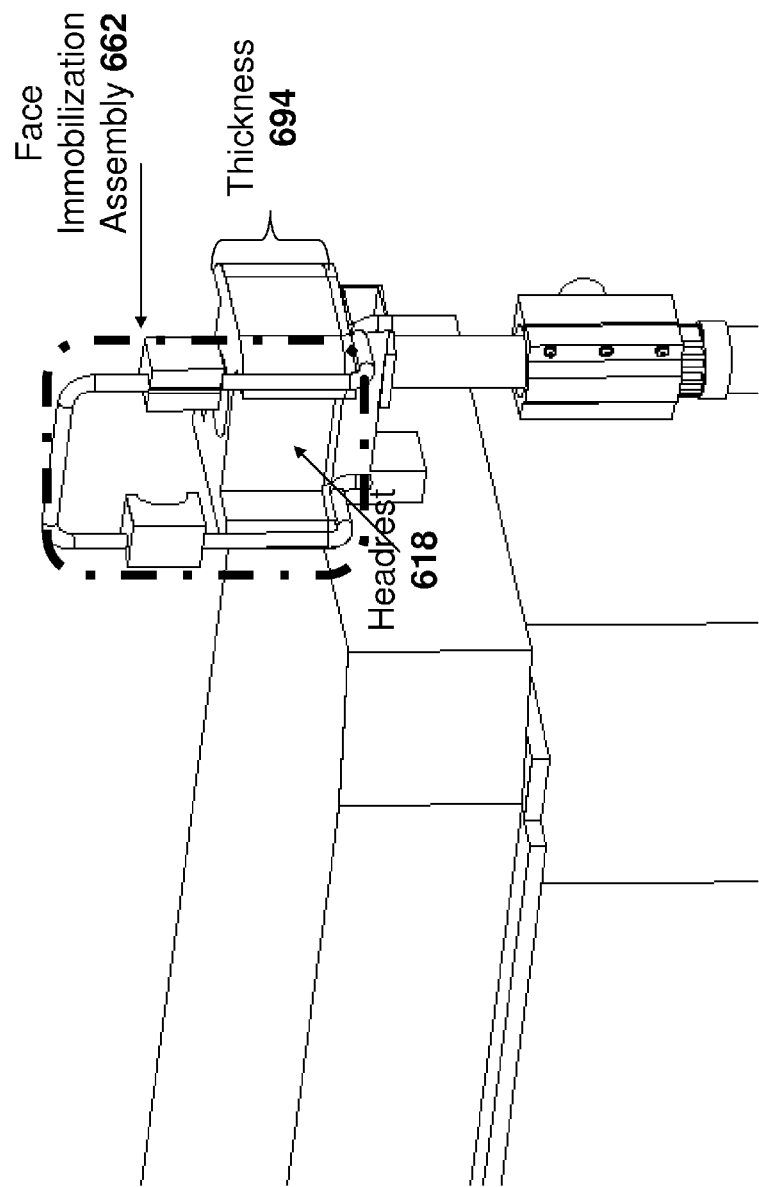

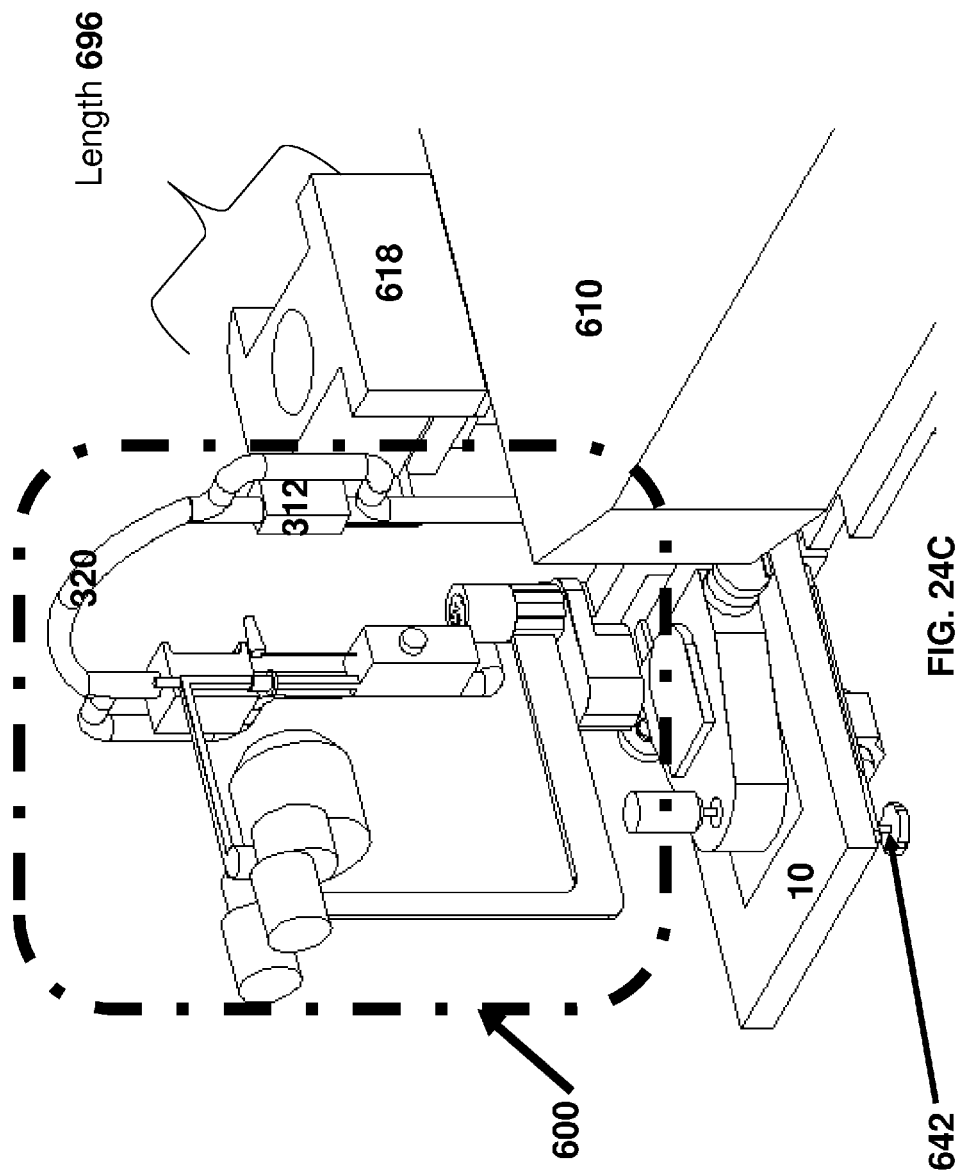

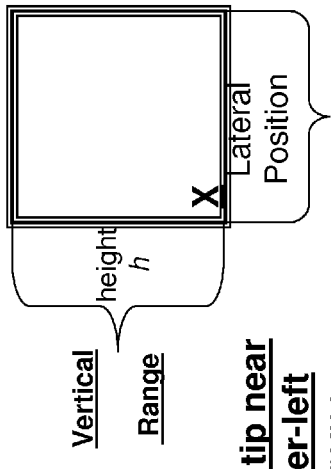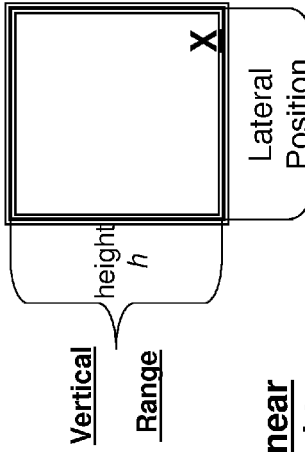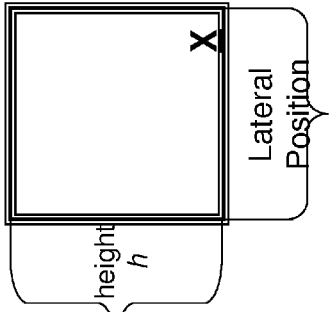
FIG. 27B

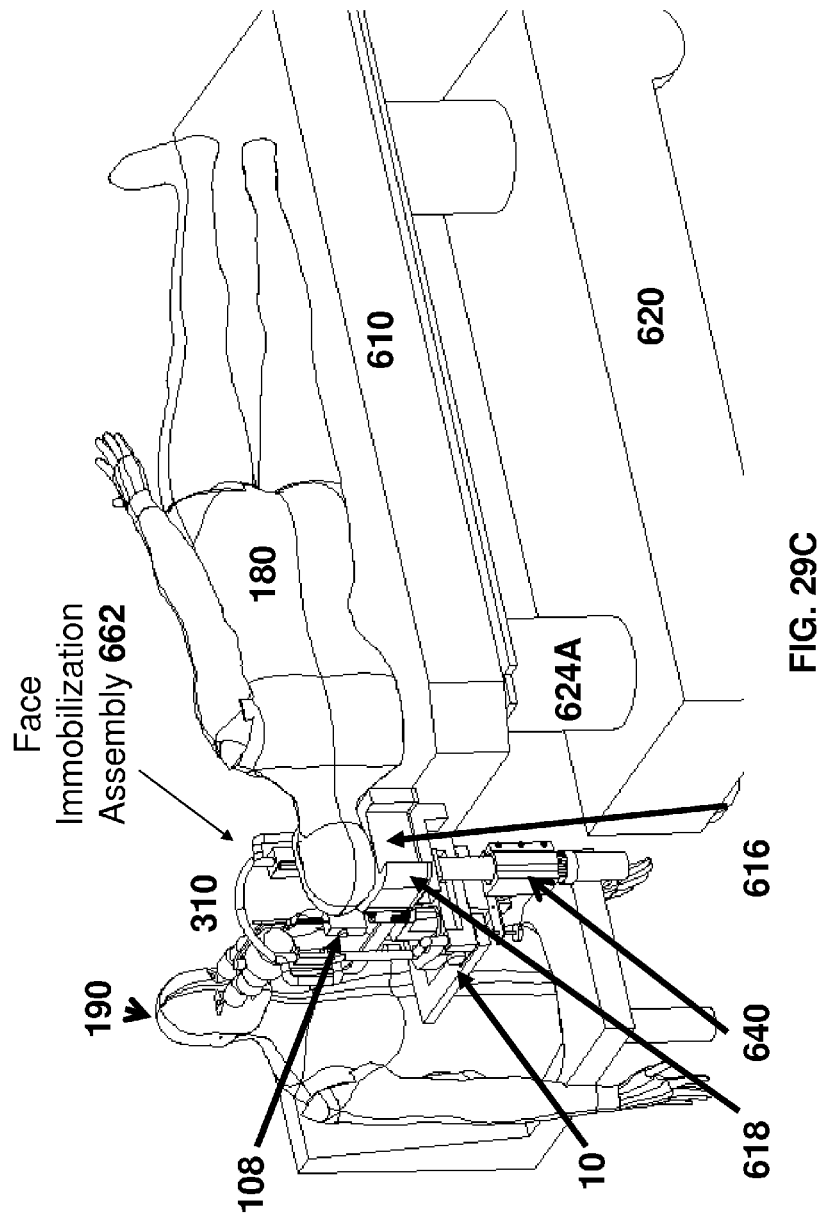

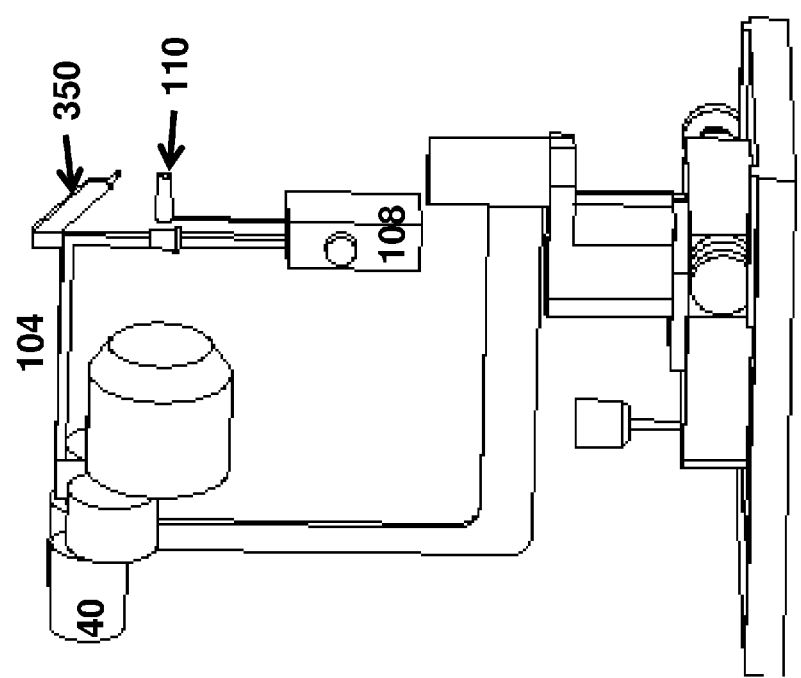

GOLDMANN APPLANATION TONOMETER, BIOMICROSCOPY DEVICE AND RELATED METHODS

CROSS-REFERENCE TO RELATED APPLICATIONS

This patent application is a continuation-in-part of U.S. Non-Provisional Patent Application Number 13037355 filed on Feb. 28, 2011. This patent application is a continuation-in-part of PCT/US11/26561 filed on Feb. 28, 2011. This patent application claims the benefit of U.S. Provisional Patent Application No. 61/414,423 filed on Nov. 17, 2010. This patent application claims the benefit of U.S. Provisional Patent Application No. 61/319,117 filed on Mar. 30, 2010. This patent application claims the benefit of U.S. Provisional Patent Application No. 61/308,339 filed on Feb. 26, 2010.

FIELD OF THE INVENTION

Embodiments of the disclosed subject-matter relate to applanation tonometry devices and/or slit lamp devices and related methods for eye examination.

BACKGROUND AND RELATED ART

The intra-ocular pressure (TOP), i.e., the pressure within the eyeball, of a person is one of the most important parameters indicating the health status of the person's eye. Various eye diseases cause the TOP to be higher or lower than normal, but it is mainly elevated when the patient is suffering from glaucoma. Glaucoma is an extremely common condition afflicting about 2% of the population over 40 years of age and is one of the major causes of blindness in the world. This disease has no symptoms and is usually diagnosed by tonometry measuring the TOP of the subject. Tonometry is therefore a routine procedure in all eye examinations, especially those of adults.

There are various types of tonometers for measuring the TOP. One type, called an "indentation tonometer", or "impression tonometer", measures the TOP by measuring a deformation produced in the subject's cornea when a constant force is applied. However, the more common type is the "applanation tonometer", which flattens the cornea and measures the force applied. The commonest and most reliable tonometer used at the present time is called the Goldmann applanation tonometer, in which a flat plate is pressed against the subject's cornea, and the area of applanation is viewed by means of a slit-lamp and microscope until the diameter of applanation is found to be 3.06 mm. Thus, it was found by Goldmann that at an applanation diameter of 3.06 mm (or an applanation area of 7.35 $mm^2$), the force required to distort the cornea from its convex shape to a flat shape counterbalances the surface tension effect of the tear-film of the subject, such that when using this applanation diameter, the force in grams multiplied by "10" is directly converted to the TOP in mm of Hg.

In the Goldmann tonometer, the applanation area is measured by optically splitting it into two halves by a biprism, one half being displaced 3.06 mm relative to the other. A fluorescent solution is first applied to the eye to form a ring which is seen as two semi-circles. A control (e.g. a manually rotatable dial) is used to apply a flattening force to the subject's cornea. When the two semi-circular rings touch, the position of the dial, calibrated in mm Hg, indicates the force required to produce an applanation diameter of 3.06 mm.

Tonometer devices in general, and applanation tonometry devices in particular, may be classified either as (i) slit-lamp-mounted tonometers (for example, the Goldmann tonometer slit-lamp apparatus in FIG. 1) and (ii) portable tonometers (for example, the Perkins tonometer illustrated in FIG. 2). Both the Goldmann and Perkins tonometry devices have been widely used for detecting glaucoma and for evaluating patients with glaucoma for decades.

There is an ongoing medical need for improved tools and methods for detecting and monitoring glaucoma. In particular, there is an ongoing medical need for improved tonometry device and methods.

A Discussion of Goldmann Tonometry Devices and of Slit-Lamp Devices

FIG. 1 is a drawing of a conventional slit-lamp Goldmann applanation tonometry system for measuring an intraocular pressure of a patient's eye. At a time when the face of the patient 180 is immobilized in the rectangular-shaped face-immobilizing-frame 120 including substantially-horizontal chin rest 90, medical attendant 190 controls the position of tonometry probe 110 using a mechanical controller 30 to move the distal tip of probe 110 into contact with the patient's cornea. Horizontal-orientation-constrained probe 110 is mounted to the biomicroscopy device so that its orientation is mechanically constrained in a 'horizontal' orientation/horizontal local plane perpendicular to a gravity vector.

As is illustrated in FIGS. 1 and 4, the examination is carried out when patient is sitting. Thus, the examination is carried when the head of the patient 180 is oriented so that an inter-pupillary vector connecting his/her eyes is horizontal and/or is co-planar with the inter-pupillary vector connecting the eyes of medical attendant 190.

As shown in FIG. 3, light incident upon the patient's cornea at the time of contact between a distal end of probe 110 and the patient's cornea enters into tonometry probe 110 and traverses the tonometry probe in a 'proximal direction.' After traversing the tonometry probe 110, this light continues in the 'proximal' direction until it enters into microscope assembly 40. The location at which the distal end of the tonometry probe contacts the cornea of the patient 190 is in the field of view of the microscopy assembly and is viewable by medical attendant 190—for example, as semi-circles.

Because tonometer probe 110 points away from attendant 190 and towards patient 180, the 'proximal' and 'distal' ends of the proximal-distal vector of FIGS. 1 and 4 (this vector happens to be substantially horizontal) are labeled such that 'proximal' means closer to attendant 190, while 'distal' means farther from attendant 190 (and closer to the eye of patient 180). Horizontal-orientation-constrained tonometry probe 110 points 'away from' attendant 190 and to patient 180—thus, the proximal-distal vector of probe 110 of FIGS. 3 and 5A correspond to the proximal-distal vector of FIGS. 1 and 4.

In FIGS. 1-4 two horizontal directions are illustrated—the 'lateral direction' which corresponds to attendant's left and right, and the 'longitudinal direction' which is the vector from attendant 190 to the patient 180 and/or coincides with the vector from a centroid of microscope assembly 40 and tonometry probe 110 and/or coincides the 'proximal-distal' vector. As will be discussed below (see, for example, FIGS. 9-11 and the accompanying discussion), conventional slit lamp devices and Goldmann applanation tonometry devices are constructed so that the set of possible 'longitudinal,' 'lateral' and 'vertical' positions of a distal end (i.e. a centroid of the distal end) of tonometry probe are range-bound.

Typically, Goldmann applanation systems are provided as 'add-ons' to a biomicroscopy slit-lamp device and can be reversibly mounted to the slit-lamp device. Commercially, a number of vendors sell slit-lamps and Goldmann applanation assemblies separately. Thus, it may be said that the slit-lamp biomicroscopy device and the Goldmann applanation system of FIG. 1 'share' a common illumination source (i.e. slit-lamp 70 light of illumination column which emits a substantially-vertical narrow beam of light) and a common microscope assembly 40. The 'common components' may be used either to measure the patient's IOP when in 'Goldmann tonometry mode' or for other biomicroscopy functionality.

FIG. 1 illustrates a conventional slit-lamp Goldmann applanation system when the Goldmann applanation assembly is mounted to the slit-lamp. FIG. 4 illustrates the slit lamp in the absence of the Goldmann applanation 'add-on' assembly—i.e. when the Goldmann applanation assembly is not mounted to the slit lamp.

The conventional slit-lamp apparatus of FIGS. 1 and 4 includes: (i) a lower base 10—for example, including a tabletop as illustrated, (ii) an upper base 20 or carriage which is movable (for example, slidable or glidable or otherwise movable) over the surface of the lower base 10; (iii) microscope assembly 40 which supported by microscope support arm 50; and (iv) an illumination column including slit-lamp light 70.

In the example of FIG. 1, upper base (carriage) 20 bears the weight of the microscopy assembly 40 and the illumination column via base column 22, and horizontal motion (i.e. lateral or longitudinal) of the upper base 20 over the lower base 10 causes 'in-tandem' motion of the both the microscope assembly 40 and the illumination column. For the specific system illustrated in FIGS. 1 and 4, there are two ways to horizontally move the upper base (carriage) 20 over the surface of the lower base: (i) a 'coarse-movement' mode whereby the medical attendant (or anyone else) may directly place his/her hands on upper base (carriage) 20 and directly move upper base (carriage) 20 horizontally; and (ii) a 'fine-movement mode' regulated by a manual or motorized control 30 such as a joystick.

When the Goldmann tonometry assembly including probe 110 and spring-container 108 is mounted to the slit-lamp (e.g. via port 102), the position of the probe 110 is fixed relative to movable carriage 20 at a time when the device is operated. Because both probe 110 as well as microscope assembly 40 are both mounted to upper base (carriage) 20, the probe 110 and microscope assembly 40 move horizontally in tandem with each other (for example, in 'fine-movement' mode (i.e. using control 30) or in 'coarse-movement mode). Furthermore, probe 110 is mounted to the slit-lamp and to movable upper base (carriage) 20 such that the probe 110 and microscope assembly 40 move vertically in tandem—for example, by raising or lowering an upper surface of base-column 22 which bears the weight of both microscope assembly 40 and probe 110.

For this purpose, a 'vertical motion controller' that is either separate from the horizontal motion controller 30 or the same as (i.e. in a 'dual-mode controller) horizontal motion controller 30.

In particular implementations, microscope assembly 40 and/or probe 110 also move horizontally and/or vertically 'in-tandem' with slit-lamp light 70, passive optical component(s) (e.g. minor) configured to re-direct a beam of light from a substantially vertical to a substantially horizontal direction.

The position of face-immobilizing-frame 120 is rigidly fixed relative to the lower base 10 so that vertical and/or horizontal motion of upper base (carriage) 20 relative to lower base 10 moves probe 110 relative to the fixed-position face-immobilizing-frame 120. When the patient 180 places his/her face over chin rest 90, the elevation of his/her face and the height of his/her eyes is fixed. Motion of the distal end of horizontal-orientation-fixed probe 110 (and hence 'in-tandem' horizontal and vertical motion of microscopy assembly 40) relative to the patient's eyes is provided using one or more controller(s) 30. As explained below, in Goldmann tonometry devices, both horizontal and vertical-motion is range-limited.

FIGS. 5A-5C illustrates some exemplary Goldmann tonometry assemblies and components thereof. In FIG. 5A, tonometry probe 110 is connected, via probe arm 106 to spring-loaded control container 108 (e.g. box) which urges tonometry probe 110 forward (i.e. in the 'distal direction') with an amount of force controllable by spring control/knob 116. In the example of FIG. 5A, spring-loaded controller 108 is connected to the Goldmann tonometry port 102 via a mediating attachment element 104. As illustrated in FIG. 5B, tonometry probe 110 includes a central axis 114 and is attached to probe arm 106 via socket 112. FIG. 6 is a top view of the device of FIG. 1.

FIGS. 7-8 illustrate additional configurations whereby a tonometry probe is mounted directly or indirectly to a slit lamp device and/or a movable carriage 20 so that the probe position and orientation relative to microscope assembly 40 is fixed for in-tandem horizontal and vertical motion and/or so that probe 110 move 'in-tandem' with microscope assembly 40 and/or with other component(s). FIG. 7B illustrates the tonometry assembly in isolation; FIGS. 7A and 7C illustrate the same tonometry assembly mounted to the slit-lamp.

For the examples of FIGS. 5A-5B and 7B, it is observed that (i) Goldmann probe 110 is mechanically constrained in a horizontal orientation; (ii) an elevation difference between Goldmann probe 110 and spring-loaded controller 108 (or springs thereof) is mechanically constrained and fixed; (iii) probe 110 is mounted to the biomicroscopy device and/or carriage 20 and/or slit-lamp device via spring-loaded controller 108. and (iv) probe 110 is not housed in a common housing with spring-loaded controller 108—instead, probe 110 (i.e. within socket or probe-holder 112) is housed separately from spring-loaded controller 108 and connected to spring-loaded controller 108 via probe arm 106 for transmitting forces which is also 'external' to housing of spring-loaded controller 108.

In the examples of FIGS. 1 and 7 the probe may be said to be 'hanging' from the slit lamp—in FIG. 1 spring-loaded controller 108 (i.e. which supports tonometry probe 110) is hanging from the slit lamp, and in FIG. 7 probe 110 is 'hanging' from a higher element which rests atop the slit-lamp. Thus, in some examples, the tonometry probe may be said to be hanging. In contrast, in FIGS. 8A-8B the tonometry probe is suspended above a spring-loaded controller 108 which rests upon a portion of the slit lamp. Both the 'hanging' and 'non-hanging' cases provide in-tandem vertical and horizontal motion between the microscope 40 and the probe 110—in both cases, carriage 20 bears the weight of both microscope 40 and probe 110.

Horizontal and Vertical 'Overall' Ranges of Mounted Probe 110 in Tandem with One or More Additional Elements Vertical Range of 'Vertical In-Tandem Motion' of Probe 110 and Microscope Assembly 40—

The 'vertical range' of tonometry probe 110 refers to the range of in-tandem vertical movement (i.e. during normal operation of the slit lamp and when the height of lower base 10 and/or a portion of carriage/upper base 20 is fixed) of mounted horizontal-orientation-constrained probe 110 in tandem with microscope assembly 40 and/or monocular or binocular eyepiece 42 thereof. Even though conventional devices provide this feature, the total 'vertical range' is relatively small—in the case of the Pharos L-0185, the total 'vertical range' is 3 cm, as illustrated in FIG. 9A.

In many conventional slit-lamp-mounted Goldmann tonometer devices, this 'vertical in-tandem motion' also includes in-tandem motion of illumination column 60 and/or slit-lamp light 70, and/or in-tandem motion of passive optical component(s) 80 (e.g. including one or more minors of a minor assembly 80) which diverts light to a 'substantially vertical light' into a substantially horizontal direction.

In many conventional slit-lamp-mounted Goldmann tonometer devices, the horizontal and/or vertical in-tandem motion of mounted horizontally-oriented probe 110 is provided by horizontal and/or vertical motion of base column 22, which simultaneously bears the weight of microscope assembly 40, probe 110, illumination column 60, slit-lamp light 70, and passive optical components (e.g. including one or more mirrors of a mirror assembly 80). As noted above, these passive optical components divert a 'substantially vertical light beam' from slit lamp light 70 into a substantially horizontal direction. As illustrated in FIG. 9B, the 'vertical range' of probe 110 in-tandem with microscope assembly 40 is provided by vertical motion of base-column 22.

Longitudinal and Lateral 'Overall' Range of in-Tandem Horizontal Motion of Probe 110 Together with Microscope Assembly As is clear from FIGS. 1 and 4, the 'lateral direction' refers to 'side-to-side' motion while the 'longitudinal direction' refers to 'frontward and backward' motion.

In Goldmann tonometry devices, mounted horizontal-orientation-constrained probe 110 horizontally moves in-tandem with carriage 20 and/or in-tandem with microscope assembly 40. The 'in-tandem horizontal motion range' assumes that the location of lower base 10 which bears the weight of the probe 110, carriage 20 and microscope assembly 40 is fixed, and refers to motion relative to lower base 10.

As is true for the case of 'vertical range,' in conventional slit-lamps, the 'horizontal in-tandem motion' (i.e. which is bounded for a fixed position of lower base 10 by a lateral or longitudinal in-tandem overall 'range') of horizontal-orientation-constrained probe 110 carriage 20 and/or with microscope assembly 40 may also include in-tandem motion with slit-lamp light 70, and/or in-tandem motion of passive optical components (e.g. including one or more mirrors of a mirror assembly 80)

For the specific examples of FIGS. 1, 4, 7, and 8, the 'longitudinal range' is limited by the length (i.e. in the 'longitudinal direction') of rail 32 over carriage 20 or a wheel 34 thereof moves relative to 'fixed' lower base 10. For the Pharos L-1085, a commercially-available slit-lamp device, the longitudinal range is 7 cm.

For the specific examples of FIGS. 1, 4, 7, and 8, the 'lateral range' is limited by the length of rack 26. For the Pharos L-1085, a commercially-available slit-lamp device, the lateral range is 11.5 cm.

It is possible to for attendant 190 to longitudinally move mounted probe 110 (e.g. in tandem with microscope assembly 40) by manually pushing forward or pulling back upper base (carriage) 20 over base 10—since carriage 20 bears the weight of probe 110 as well as microscope assembly 40, this causes in-tandem longitudinal motion of probe 110 together with microscope assembly 40. As is true for the 'vertical range case,' this 'in-tandem motion may also refer to in-tandem longitudinal motion of illumination column 60 and/or slit lamp light 70 and/or optical components.

As shown in FIGS. 10A-10B, in conventional slit-lamp-mounted Goldmann tonometry devices the lateral ranges slightly exceeds the longitudinal range.

As shown in FIGS. 11A-11B, in conventional slit-lamp-mounted Goldmann tonometry devices the lateral ranges far exceeds the relatively limited vertical range.

Longitudinal and Lateral 'Fine-Range of in-Tandem Horizontal Motion of Probe 110 Together with Microscope Assembly Most modern slit-lamp-mounted Goldmann tonometry devices provide both a mechanism for 'coarse horizontal motion' (for example, when attendant 190 directly moving carriage 20 with his/her hands) as well as a mechanism for 'fine horizontal motion.' To date, commercial slit-lamp-mounted Goldmann tonometers employ a 'hybrid-joystick control'—twisting of joystick 30 about its axis 6 serves to raise and lower mounted horizontal-orientation-constrained Goldmann tonometer probe 110 (i.e. vertically 'in-tandem with microscope assembly 40) while tilting of the joystick to the left or right can move the Goldmann tonometer probe 110 (i.e. laterally in-tandem with carriage 20 over fixed-position lower base 10 and/or laterally in-tandem with microscope assembly 40 over fixed-position lower base 10).

As is shown in FIG. 13A-13B, when joystick 30 is tilted completely to the left, this induces in-tandem lateral motion to-the-left (i.e. unless the probe 110 is range-bound by the 'overall lateral range' discussed above); and when joystick 30 is tilted completely to the right, this induces in-tandem lateral motion to-the-right ((i.e. unless the probe 110 is range-bound by the 'overall lateral range' discussed above). When the attendant removes his hands from joystick 30, joystick 30 does not return to an equilibrium upward orientation and there is no in-tandem horizontal motion resulting from the removal of the hands—instead, the orientation of joystick axis 6 remains as is, with the position of probe 110 relative to lower base 10 remaining as-is.

When joystick 30 is tilted to the left or right, there is a lateral deviation between the 'coarse motion only' position of probe tip 110 and the actual position of probe tip 110. When joystick 30 is pointing up (see FIG. 13C), there is no such deviation.

A Brief Discussion of FIGS. 14A-14B

FIGS. 14A-14B are 'side views' of the slit-lamp system of FIG. 1 both when the tonometry assembly is mounted to the slit-lamp (see FIG. 14A) and when in the absence of tonometry assembly (see FIG. 14B).

As is illustrated in FIG. 14B, it is possible to illuminate the patient's eyes by an intense, narrow beam of light substantially-vertically emitted by slit lamp light 70 of illumination column. This light is re-directed into a substantially horizontal direction by passive optical assembly 80 (e.g. a minor or reflector oriented at around 45 degrees).

In conventional slit-lamp systems, microscopy assembly 40 as well as optical assembly 80 are both supported over carriage 20 via one or more mediating elements—thus, the horizontal and/or vertical motion of microscopy assembly 40 and/or probe 110 may be 'in-tandem' with optical assembly 80 (i.e. to control the height of the horizontal beam of light that travels in a distal direction to the patient's eye (see FIG. 14B)) and/or with slit-lamp light 70 or any other portion or entirety of the illumination column.

Zeiss Configurations

In FIGS. 1, 4, 7-8 and 10 the vertical beam emitted by slit-lamp light is emitted in a downward direction from slit-lamp light 70. This is informally known as a 'Haag-Streit' slit-lamp configuration. FIGS. 15A-15B are examples of what is informally referred to as the 'Zeiss configuration.'

The following US patents provide potentially relevant background art, and are all incorporated herein by reference in their entirety: U.S. Pat. No. 2,235,319; U.S. Pat. No. 3,070, 997, U.S. Pat. No. 3,944,342; U.S. Pat. No. 4,175,839; U.S. Pat. No. 4,735,209; U.S. Pat. No. 5,363,155; U.S. Pat. No. 5,488,443, U.S. Pat. Nos. 6,072,623 and 6,083,160.

SUMMARY OF EMBODIMENTS

It is now disclosed for the first time a method of eye examination comprising: a. when a patient's body is in a side-lying position and when the patient's head is oriented sideways so that an inter-pupil vector between the patient's pupils is substantially co-linear with a gravitation vector, subjecting one of the patient's eyes to at least one eye examination selected from the group consisting of: i. a Goldmann tonometer examination; and ii. a slit-lamp biomicroscopy examination such that slices of the patient's eye at different depths are viewed in a binocular microscope, wherein the Goldmann tonometer examination is carried out by means of a horizontal-orientation-constrained applanation tonometry probe in contact with one of the patient's eyes to measure intraocular pressure (IOP) of the patient's eye such that at least one a first condition, a second condition, a third condition and a fourth condition is true, the conditions being defined a follows: i. according to the first condition, the Goldmann tonometer device is mounted to a slit-lamp which provides illumination for the IOP measurement; ii. according to the second condition, the horizontal-orientation-constrained applanation tonometry probe is horizontally moved by titling a stick of a joystick and/or vertically moved by means of a twisting a stick of a joystick so as to bring the tonometer probe into contact with the patient's eye; and/or iii. according to the third condition, cornea-applanation force for the applanation tonometer probe for the IOP measurement is provided by a spring-loaded controller that does not reside a common housing with the applanation tonometer probe; iv. according to the fourth condition, semi-circles of the cornea surface for the TOP measurement are viewable in a microscope assembly that is a Gallilean microscope and/or that is horizontally displaced from a proximal end of the tonometry probe by at least 10 cm.

In some embodiments, at least 2 or 3 or 4 of the conditions are true.

In some embodiments, i) the TOP measurement is carried out when the patient's head lays substantially flat on a stabilizing surface so that contact between a side of the patient's head and the stabilizing surface maintains the orientation of the inter-pupil vector and vertically immobilizes the patient's head; and ii) the TOP measurement is carried out to a patient's lower eye at a time when an elevation difference lower_eye_elevated between an elevation of the patient's lower eye and an elevation of the stabilizing surface is at most than 5 cm.

In some embodiments, the elevation difference lower_eye_elevated is at most than 3 cm.

In some embodiments, the TOP measurement is carried out when the patient's head lays substantially flat on a stabilizing surface so that a majority of a surface area of a side of the patient's head is in contact with the stabilizing surface so that the stabilizing surface maintains the orientation of the inter-pupil vector and vertically immobilizes the patient's head.

In some embodiments, the TOP measurement is carried out when the patient's head lays substantially flat on a stabilizing surface so that head-surface contact region has a width in a direction perpendicular to a vector between a chin and a mid-point between the pupils of at least 5 cm in at least one location.

In some embodiments, performed on a patient whose head is dimensioned to have a chin-head-top length of at least 15 cm or at least 20 cm and whose head is vertically and horizontally stabilized In some embodiments, the method is carried out at a time when the patient's head lays substantially flat on a stabilizing surface having an indentation region such that: i) both of the patient's eye are directly above the indentation region; and ii) at least a portion of a spring-container which is connected to probe via a vertical-orientation-constrained probe arm has a horizontal location that coincides with at least a portion of the indentation region.

In some embodiments, the TOP measurement is carried out when the patient's head lays substantially flat on a stabilizing surface located at a proximal end of a bed and whose elevation above a bed surface on which the patient's body lies is between 10 and 20 cm.

In some embodiments, the TOP measurement is carried out when the patient's head is in contact with a face-stabilization assembly that horizontally stabilizes the patient's head.

In some embodiments, wherein the TOP measurement is carried out at a time when the patient's chin and forehead are simultaneously in contact with the face-stabilization assembly at locations that are horizontally separated from each other by at least 25 cm.

In some embodiments, the patient is awake at a time of the at least one eye examination.

In some embodiments, wherein the Goldmann tonometry examination is carried out by means of a Goldmann tonometry device that lacks an illumination column.

In some embodiments, the at least one eye examination includes the biomicroscopy examination.

It is now disclosed for the first time a eye examination system comprising: a. a bed including a bed upper surface that is dimensioned to support an adult human and/or whose width is at least 40 cm and whose length is at least 1 meter and/or whose length is at least 1 meter and whose surface area is at least 5,000 cm$^2$; and b. a slit-lamp device including an illumination column and/or a Goldmann tonometer device that is directly or indirectly attached to the bed so as to mechanically constrain motion of the eye-examination device away from the bed, the system being configured such that at least one of an attached headrest feature and a pivot axis feature is true, the attached headrest and pivot axis features being defined as follows: (i) according to the attached headrest feature, the bed is directly or indirectly attached to a headrest such that a height of upper surface exceeds a height of bed surface, a surface area of the upper surface of the headrest is at most 30% of a surface area of the bed upper surface, and the headrest is disposed at or near one end of the bed; (ii) according to the pivot axis feature, translational motion of a base of the slit lamp device and/or Goldmann tonometer device is constrained to be around a pivot axis 640 disposed at or near one end of the bed, wherein the Goldmann tonometer device includes an horizontal-orientation-constrained applanation tonometer probe having a thicker proximal end and a thinner distal end, a microscope assembly, a joystick, a lower base and an upper base movable over the lower base to provide in-tandem horizontal motion of the upper base and the tonometer probe over the lower base, the joystick configured to regulate and/or to induce the in-tandem horizontal motion, the microscope assembly being configured to receive light which passes in a proximal direction through tonometer probe so that a location in contact with a distal end of the probe is in a field of view of the microscope assembly.

In some embodiments, the system includes the Goldmann tonometry device.

In some embodiments, the Goldmann tonometry device includes an illumination column of a slit lamp device.

In some embodiments, the system includes the slit lamp device including the illumination column.

In some embodiments, at least the attached headrest feature is true.

In some embodiments, at least the pivot axis feature is true.

In some embodiments, both of the attached headrest feature and the tonometer feature are true.

In some embodiments, the attached headrest feature is true and the system further includes a face immobilization assembly which when attached to or substantially brought into contact with headrest frames, in combination with the headrest upper surface and/or a planar extension thereof, a given region of space whose elevation exceeds an elevation of the headrest upper surface, the region of space being above headrest upper surface and/or horizontally displaced from the headrest upper surface by no more than 10 cm, a height of the framed given region being at least 8 cm and a length of the framed region being at least 20 cm.

In some embodiments, the face immobilization assembly is attached to headrest (for example, so that the headrest supports the weight of the face immobilization assembly).

In some embodiments, the face immobilization assembly is not in contact with headrest In some embodiments, the face immobilization assembly includes vertically-disposed forehead rest and chinrest that are horizontally separated from each other by at least 20 cm in a direction that is parallel to a central axis of the bed.

In some embodiments, the face immobilization assembly includes vertically-disposed forehead rest and chinrest, at least one of which is constructed of a rigid inner core and an outer softer and/or pliable layer.

In some embodiments, the face immobilization assembly includes vertically-disposed forehead rest and chinrest, at least one of which is includes a horizontally-oriented recess on a contact surface.

In some embodiments, i. the attached headrest feature is true; i. the headrest defines a first direction substantially parallel to the bed central axis and a second direction perpendicular to the first direction; ii. a length L of the headrest along the first direction is at least 30 cm and a width of the headrest along the second direction is at least 20 cm; iv. the headrest includes first and second edges substantially parallel to the bed central axis and disposed at opposite sides of the headrest; and v. for at least one of the first and second edges, the headrest includes an indentation disposed at the edge, such that a length of the indentation is at least 5 cm and/or at least 25% of the length L of the headrest along the first direction.

In some embodiments, the indentation region length is at most 80% of the headrest length.

In some embodiments, a depth of the indentation along the second direction is at most 50% of the length and/or at most 5 cm. and/or at most 30% of the width.

In some embodiments, a ratio between a surface area of the indentation and a surface area of the upper surface of headrest is at most 0.2 or at most 0.1 or at most 0.3 or at most 0.5.

In some embodiments, the headrest respectively includes at least two such indentations that are respectively disposed at the first and second edges.

In some embodiments, for one or both of the indentations, a ratio between a surface area of the indentation and a surface area of the upper surface of headrest is at most 0.2

In some embodiments, for one or both of such indentations, a center of the indentation is horizontally displaced by at least 8 cm along the first direction from any edge of the headrest.

In some embodiments, the headrest feature is true and the surface area of upper surface of headrest is at least 250 cm or at least 500 cm or at most 1,000 cm or at most 500 cm. In some embodiments, a ratio between a surface area of the bed surface and a surface area of the headrest is at least 5:1 or at least 10:1 or at least 20:1 or at least 30:1 and/or at most 50:1 or at most 30:1 or at most 20:1 or at most 10:1.

In some embodiments, the headrest feature is true and the upper surface comprises a soft or pliable material placed above a rigid support of headrest.

In some embodiments, the headrest is dimensioned so that a width of the headrest in a dimension substantially perpendicular to the bed central axis is at least 20 cm.

In some embodiments, the joystick is a dual mode joystick configured: i. to regulate and/or to induce the in-tandem horizontal motion of the microscope assembly and the tonometry probe by titling of a stick of the joystick; and ii. to induce in-tandem vertical motion of the microscope assembly and the horizontal-orientation-constrained applanation tonometer probe by twisting the stick of the joystick around its axis.

In some embodiments, a vertical range of the induced in-tandem vertical motion provided by the twisting of the stick of the joystick is at least 7 cm.

In some embodiments, i) the attached headrest feature is true, ii) the lower base includes a horizontal tonometer-base upper surface below upper base whose height is equal to a height of movable upper base within a tolerance of 15 cm; iii) a height of the tonometer-base upper surface is below a height of the upper surface of headrest by at most 50 cm.

In some embodiments, the tonometer motion feature is true and wherein the pivot axis is located substantially at a centerline of the bed along its elongate axis within a tolerance that is less than bed width.\

In some embodiments, the tolerance is less than 50% of the bed width and/or less than 15 cm. and/or less than 25% or the bed width and/or less 10 cm.

In some embodiments, the weight of the upper base and microscope is born at a location that coincides with the pivot axis In some embodiments, a radius of motion around the pivot axis at least 20 cm or at least 30 cm or at least 50 cm or at most 1 meter or at most 75 cm or at most 25 cm.

It is now disclosed a tonometry system comprising: a. an horizontal-orientation-constrained applanation tonometer probe having a thicker proximal end and a thinner distal end; b. a microscope assembly configured to receive light which passes in a proximal direction through tonometer probe so that a location in contact with a distal end the probe is in a field of view of the microscope assembly; c. a lower base; d. an upper base movable over the lower base to provide in-tandem horizontal motion of the upper base and the tonometer probe over the lower base, e. a dual mode joystick configured: i. to regulate and/or to induce the in-tandem horizontal motion by titling of a stick of the joystick; and ii. to induce in-tandem vertical motion of the microscope assembly and the horizontal-orientation-constrained applanation tonometer probe by twisting the stick of the joystick around its axis, wherein a vertical range of the induced in-tandem vertical motion provided by the twisting of the stick of the joystick is at least 7 cm.

It is now disclosed an eye examination system comprising: a. an horizontal-orientation-constrained applanation tonometer probe having a thicker proximal end and a thinner distal end; b. a microscope assembly configured to receive light which passes in a proximal direction through tonometer probe so that a location in contact with a distal end the probe is in a field of view of the microscope assembly; c. a lower base; d. an upper base movable over the lower base to provide in-tandem horizontal motion of the upper base and the tonometer probe over the lower base, e. an elevated head rest held at a constant orientation and position relative to the lower base, an elevation of an upper surface of head rest exceeding an elevation of a flat surface of lower base over which the lower base moves by at least 5 cm or by at least 10 cm, the elevated head rest having both lengths and widths that exceed 10 cm; f. a face immobilization assembly including first and second vertical elements connected to each other via an upper horizontal element, the face immobilization assembly configured in combination with the headrest upper surface and/or a planar extension thereof to frame a region of space such that: i. an elevation of the frame region of space exceeds an elevation of the headrest upper surface; ii. a horizontal location of the entire frame region of space is less than 5 cm from the headrest upper surface; iii. a height of the framed region of space is at least 8 cm; iv. a length of the framed region of space is at least 20 cm; and g. a motion controller assembly comprising one or more motion controllers at least one of which is joystick, the motion controller assembly being configured to: i. induce the in-tandem horizontal motion; and ii. to induce vertical motion of the tonometer probe relative to the lower base and relative to the face support surface, the motion controller assembly being configured such that a range of a distal end of the tonometry probe includes a location within the framed region of space and horizontally displaced from the elevated head rest by no more than 2 cm.

It is now disclosed a slit lamp device comprising: a. a lower base; b. an upper base movable over the lower base; c. a microscope assembly mounted onto the upper base to provide in-tandem horizontal motion of the upper base and the microscope assembly over the lower base, d. an illumination column including a slit-lamp light configured to emitted an intense thin beam of light in a substantially vertical direction; e. passive optical component(s) configured to re-direct the optical intense thin beam of light into substantially a horizontal direction away from the microscope, such that when the re-directed beam of light is incident upon a location of a reflective vertical plane, light of the re-directed beam is backwardly reflected towards microscope assembly such that the location of the vertical plane is in a field of view of the microscope assembly, e. a dual mode joystick configured: i. to regulate and/or to induce the in-tandem horizontal motion by titling of a stick of the joystick; and ii. to induce in-tandem vertical motion of the microscope assembly and the horizontal beam re-directed by twisting the stick of the joystick around its axis, the vertical motion of the horizontal beam modifying a height of a location in the field of view of the microscope, wherein a vertical range of the induced in-tandem vertical motion provided by the twisting of the stick of the joystick is at least 7 cm.

It is now disclosed a slit lamp device comprising: a. a lower base; b. an upper base movable over the lower base; c. a microscope assembly mounted onto the upper base to provide in-tandem horizontal motion of the upper base and the microscope assembly over the lower base, d. an illumination column including a slit-lamp light configured to emitted an intense thin beam of light in a substantially vertical direction; e. passive optical component(s) configured to re-direct the optical intense thin beam of light into substantially a horizontal direction away from the microscope, such that when the re-directed beam of light is incident upon a location of a reflective vertical plane, light of the re-directed beam is backwardly reflected towards microscope assembly such that the location of the vertical plane is in a field of view of the microscope assembly, f. an elevated head rest held at a constant orientation and position relative to the lower base, an elevation of an upper surface of head rest exceeding an elevation of a flat surface of lower base over which the lower base moves by at least 5 cm or at least 10 cm, the elevated head rest having both lengths and widths that exceed 10 cm, a horizontal distance between the slit-lamp light and the upper surface of head rest being less than 10 cm; g. a face immobilization assembly including first and second vertical elements connected to each other via an upper horizontal element, the face immobilization assembly configured in combination with the headrest upper surface and/or a planar extension thereof to frame a region of space such that: i. an elevation of the frame region of space exceeds an elevation of the headrest upper surface; ii. a horizontal location of the entire frame region of space is less than 5 cm from the headrest upper surface; iii. a height of the framed region of space is at least 8 cm; iv. a length of the framed region of space is at least 20 cm; and h. a joystick for inducing and/or regulating the in-tandem horizontal motion.

In some embodiments, the lower base is mounted onto a wheeled chassis and/or is a part of the wheeled chassis such that horizontal motion of the wheeled chassis causes in-tandem horizontal motion of the face support.

In some embodiments, the lower base bears the weight of head support and/or face immobilization assembly.

In some embodiments, a stick of joystick has a central location that is substantially upwards and/or joystick is mounted onto movable upper base.

BRIEF DESCRIPTION OF THE DRAWINGS

FIGS. 1-15 describe prior art tonometry and slit lamp methods and apparatus.

DESCRIPTION OF EMBODIMENTS

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

For brevity, some explicit combinations of various features are not explicitly illustrated in the figures and/or described. It is now disclosed that any combination of the method or device features disclosed herein can be combined in any manner—including any combination of features—any combination of features can be included in any embodiment and/or omitted from any embodiments.

The present inventors are now disclosing for the first time a Goldmann applanation tonometry method whereby (i) a patient's face is first immobilized so that an 'inter-pupillary 'vector' connecting his/her eyes is oriented vertically and the position of the patient's face is rigidly fixed in a 'sidewards' orientation (ii) at a time when a patient's body is in a side-lying position and when the patient's head is oriented sideways so that an inter-pupil vector 656 between the patient's pupils is substantially co-linear with a gravitation vector, employing a Goldmann tonometer device that includes a horizontal-orientation-constrained tonometry probe 110 in contact with one of the patient's eyes to measure intraocular pressure (TOP) of the patient's eye.

In different embodiments, the upper eye and/or the lower eye may be subjected to Goldmann applanation tonometry examination.

Figure 2A:
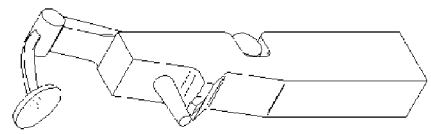
Figure 2B:
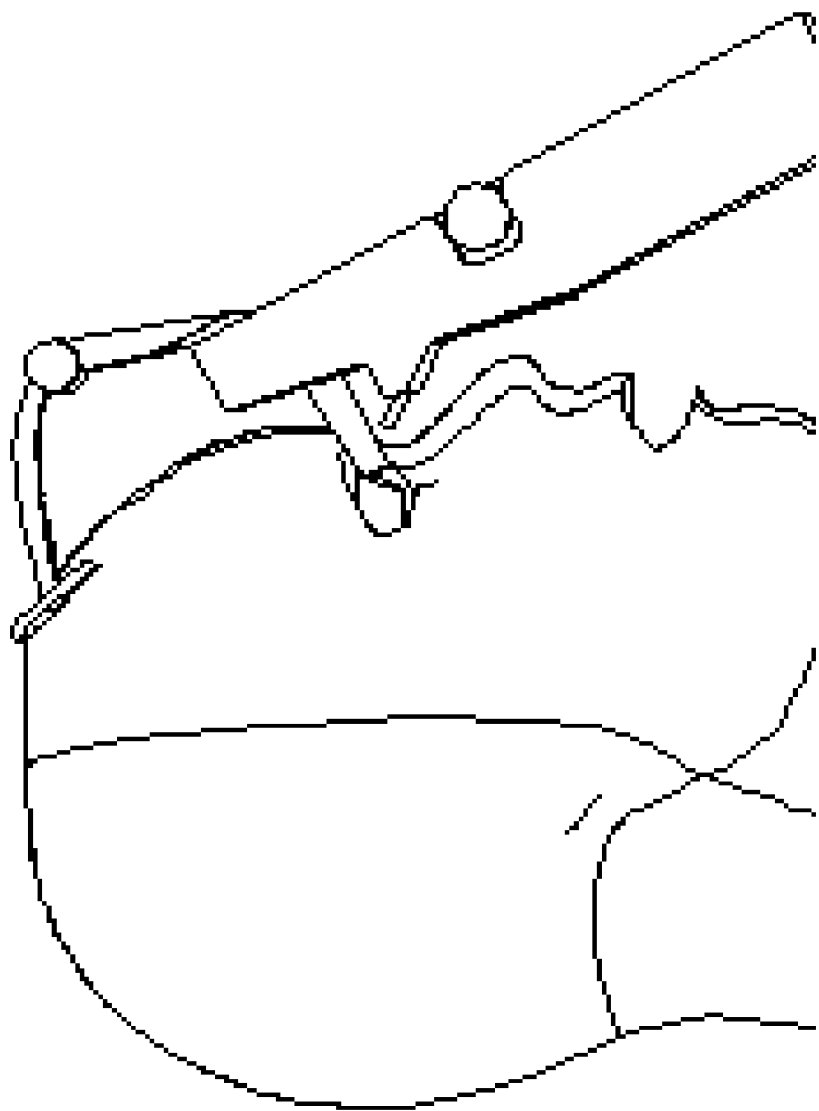
Figure 4:
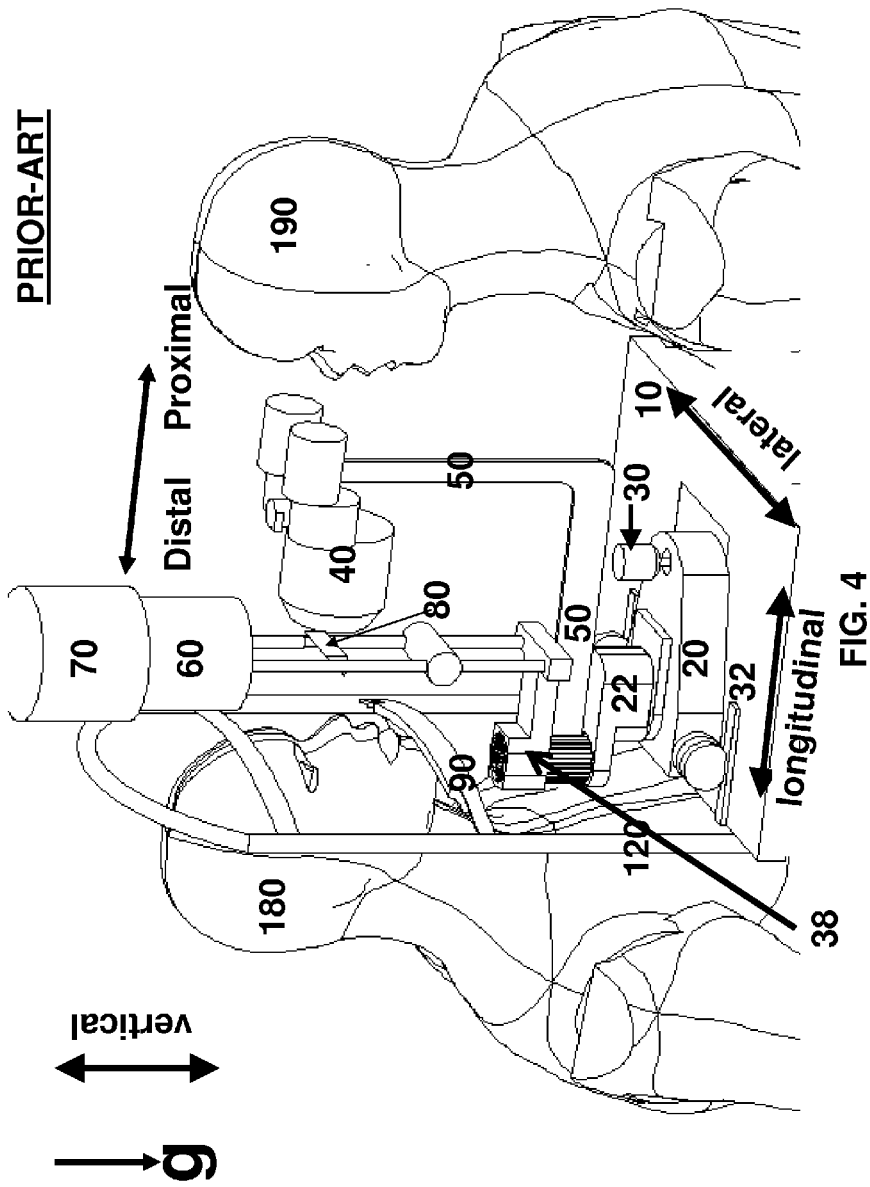
Figure 5A:
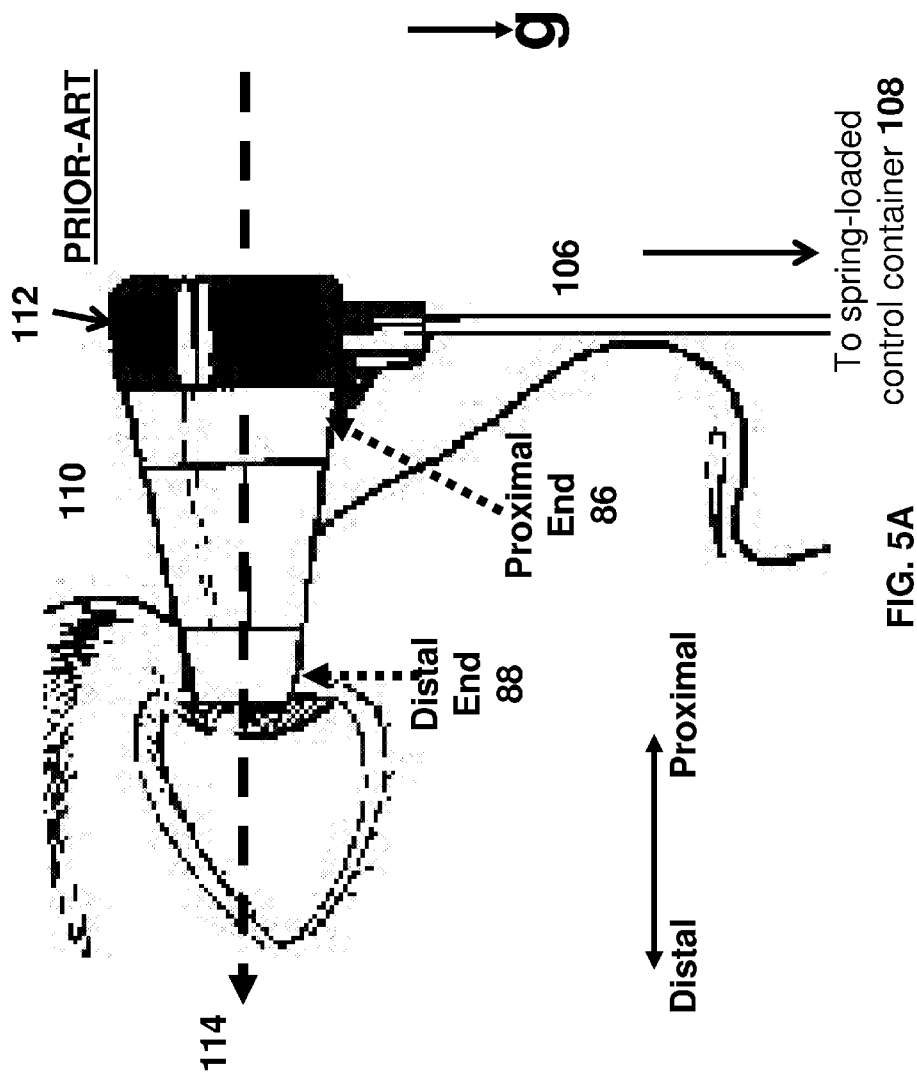
Figure 8A:
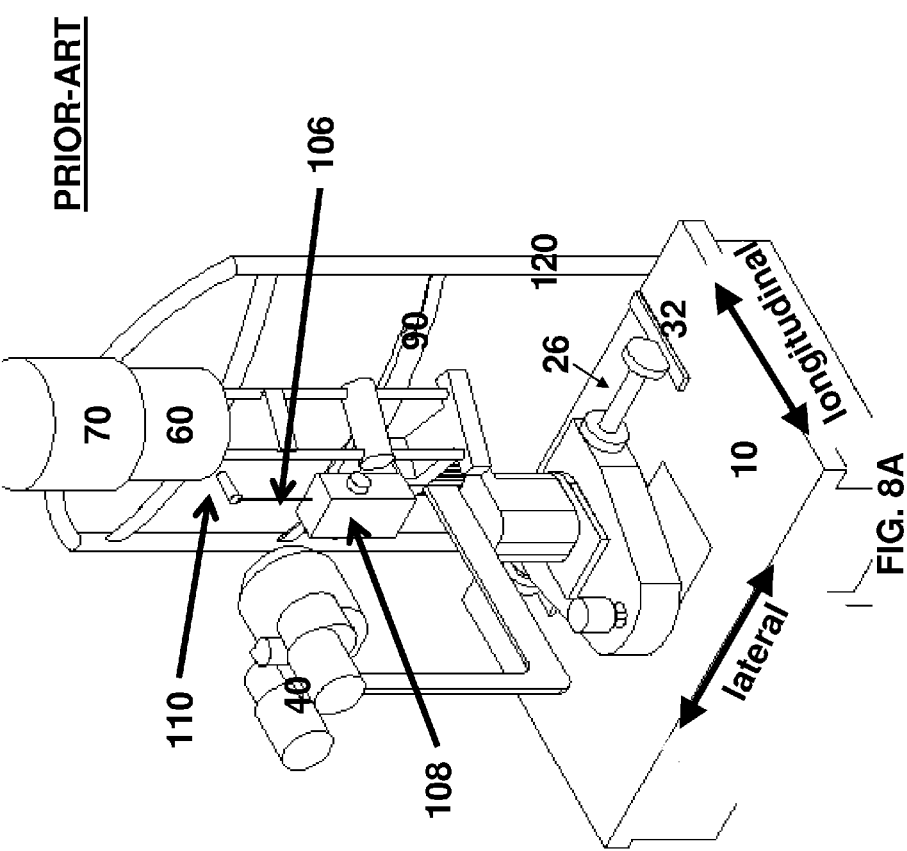
Figure 8C:
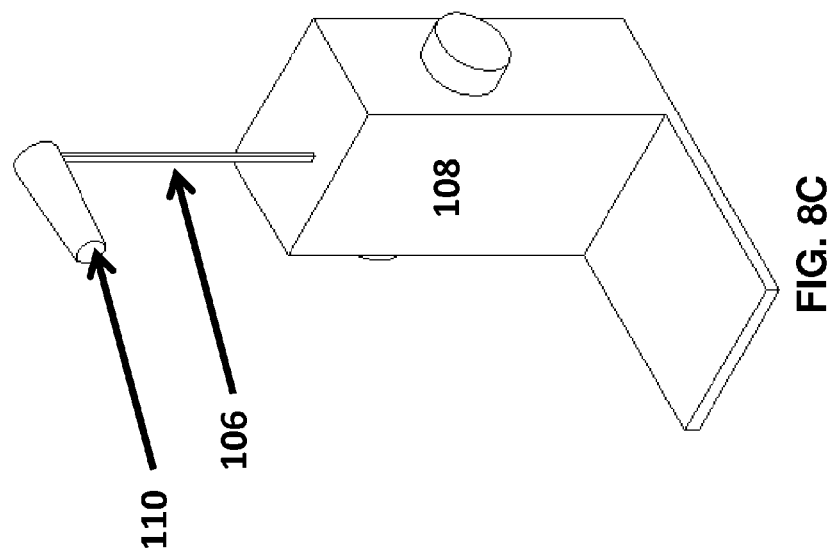
Figure 9A:
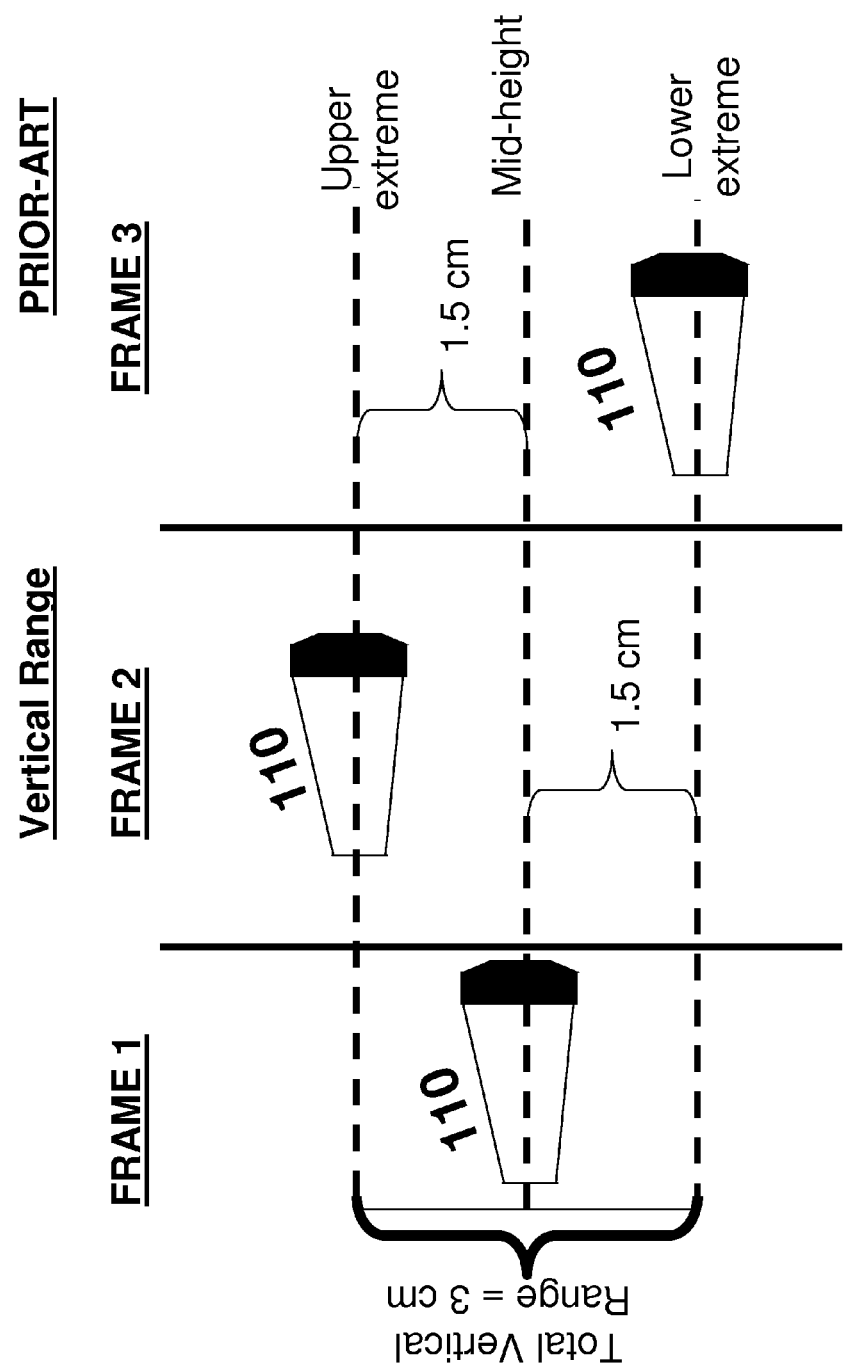
Figure 10A:
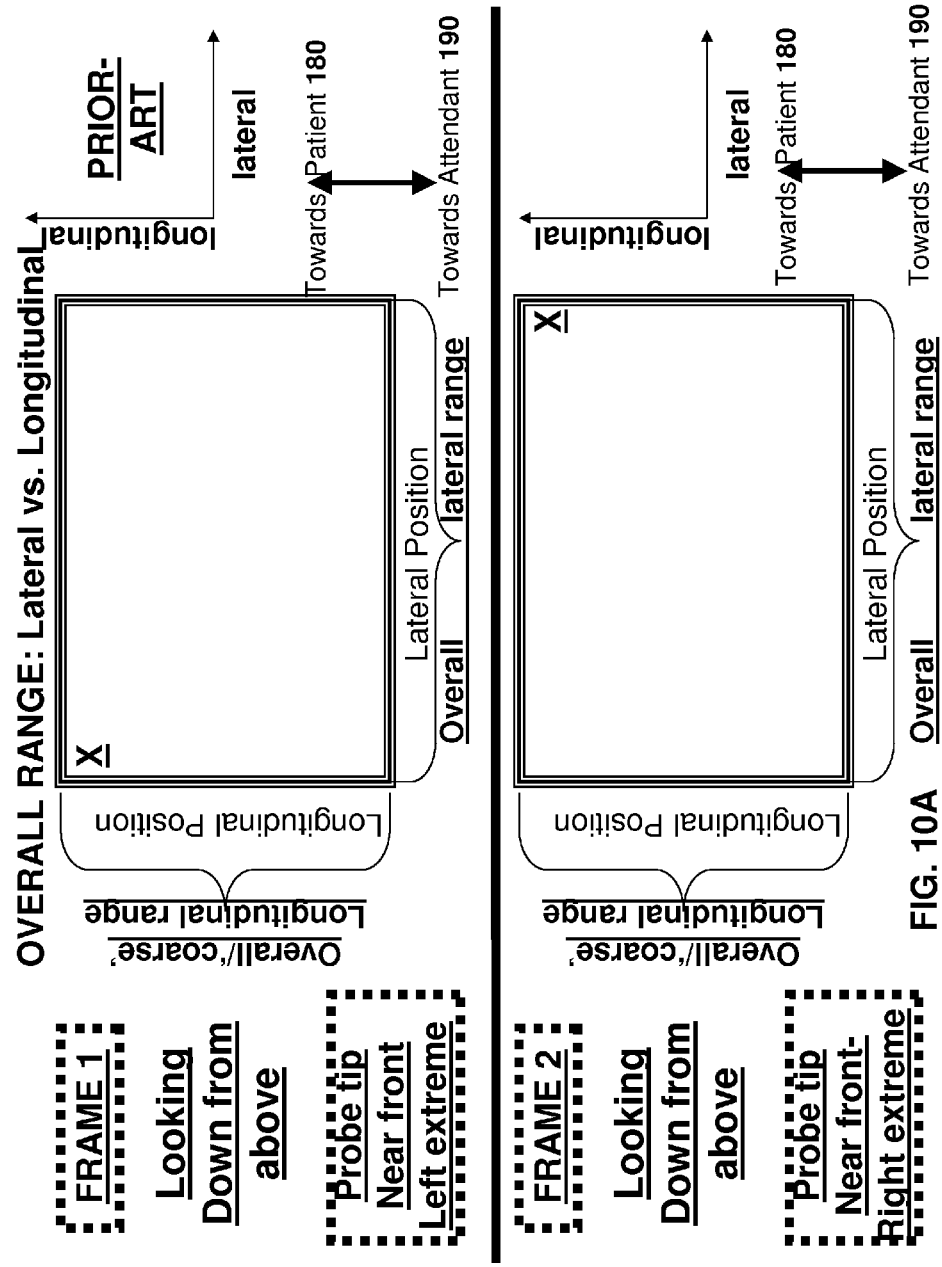
Figure 10B:
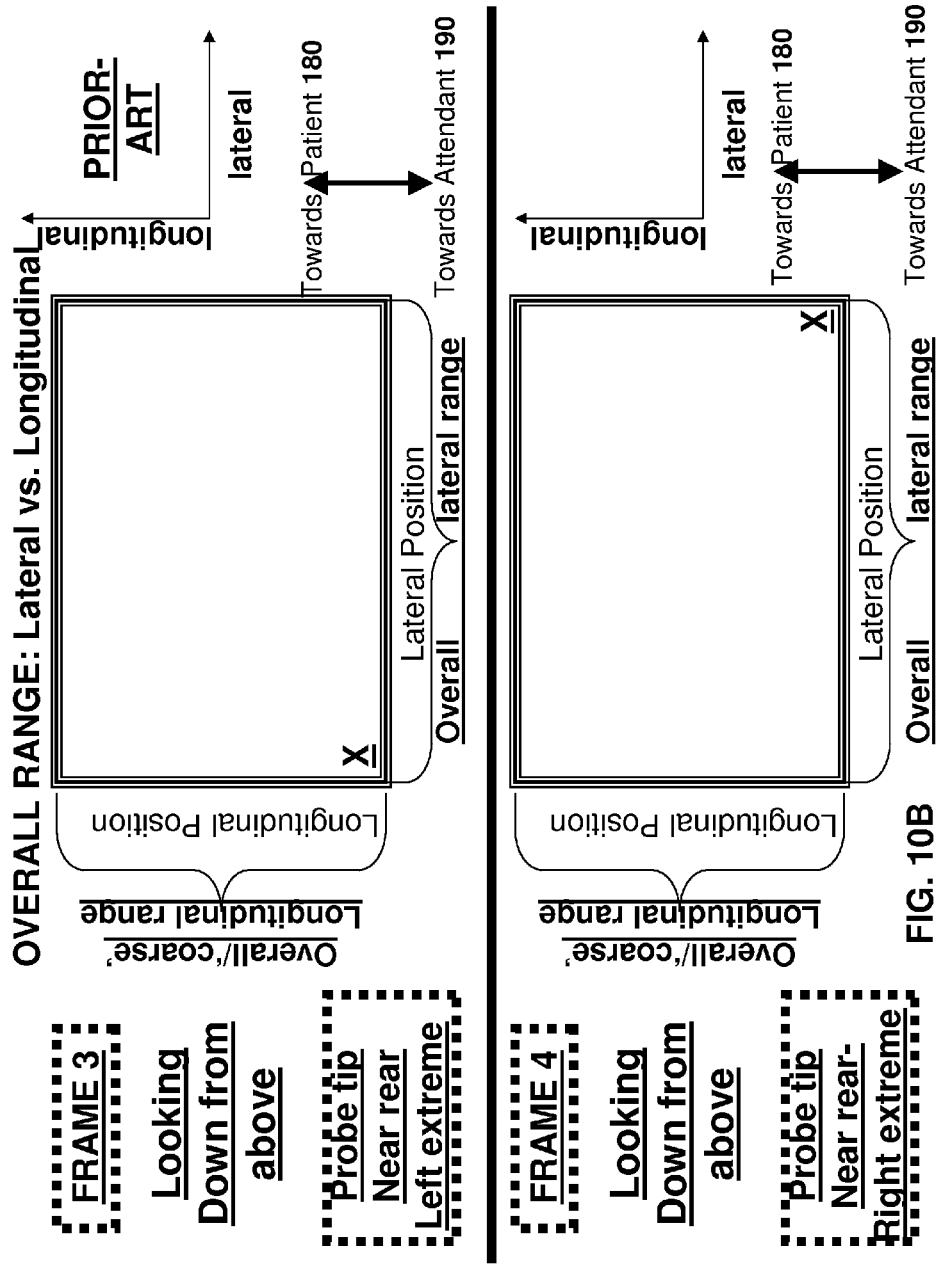
Figure 11B:
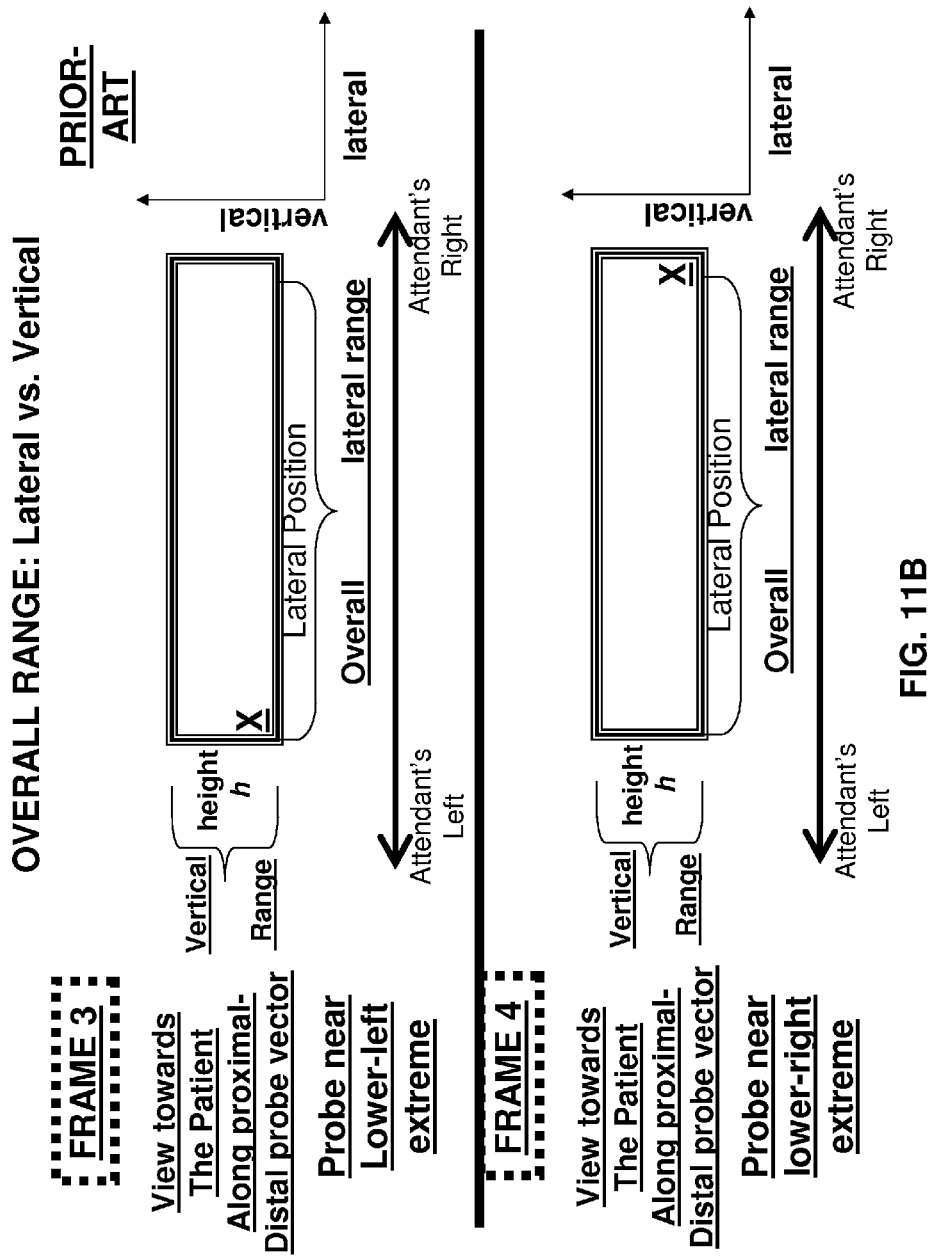
Figure 12:
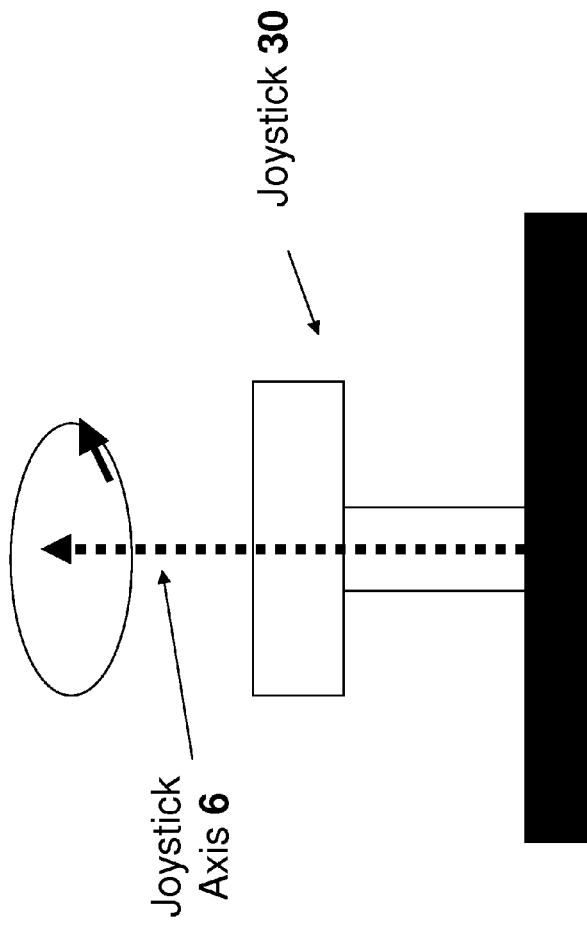
Figure 13A:
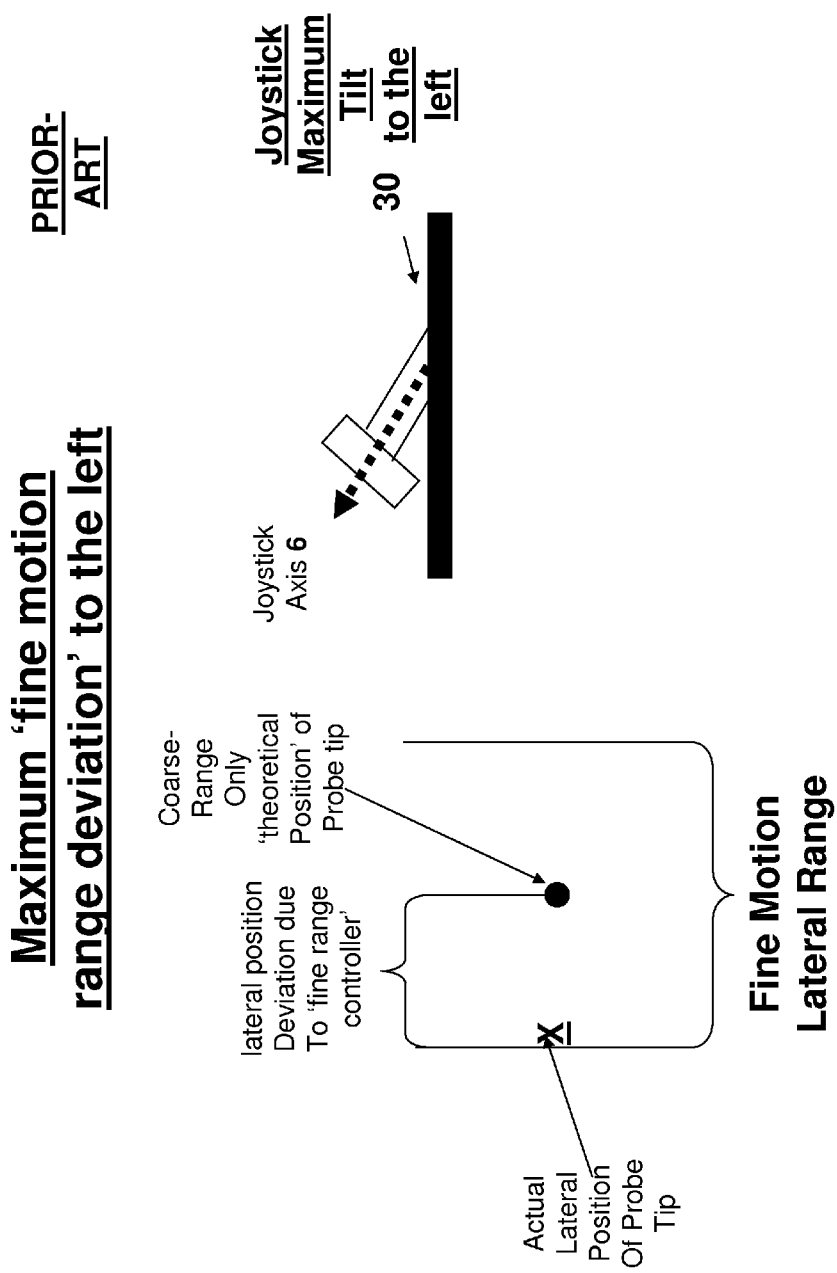
Figure 13B:
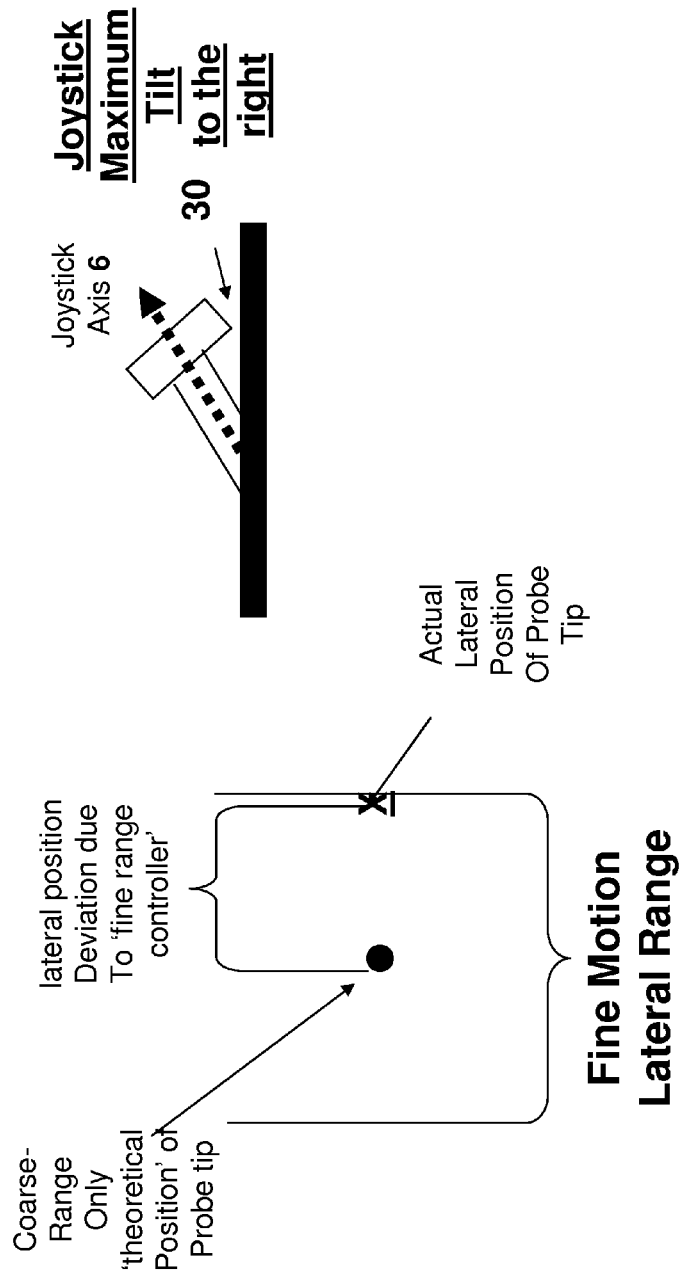
Figure 13C:
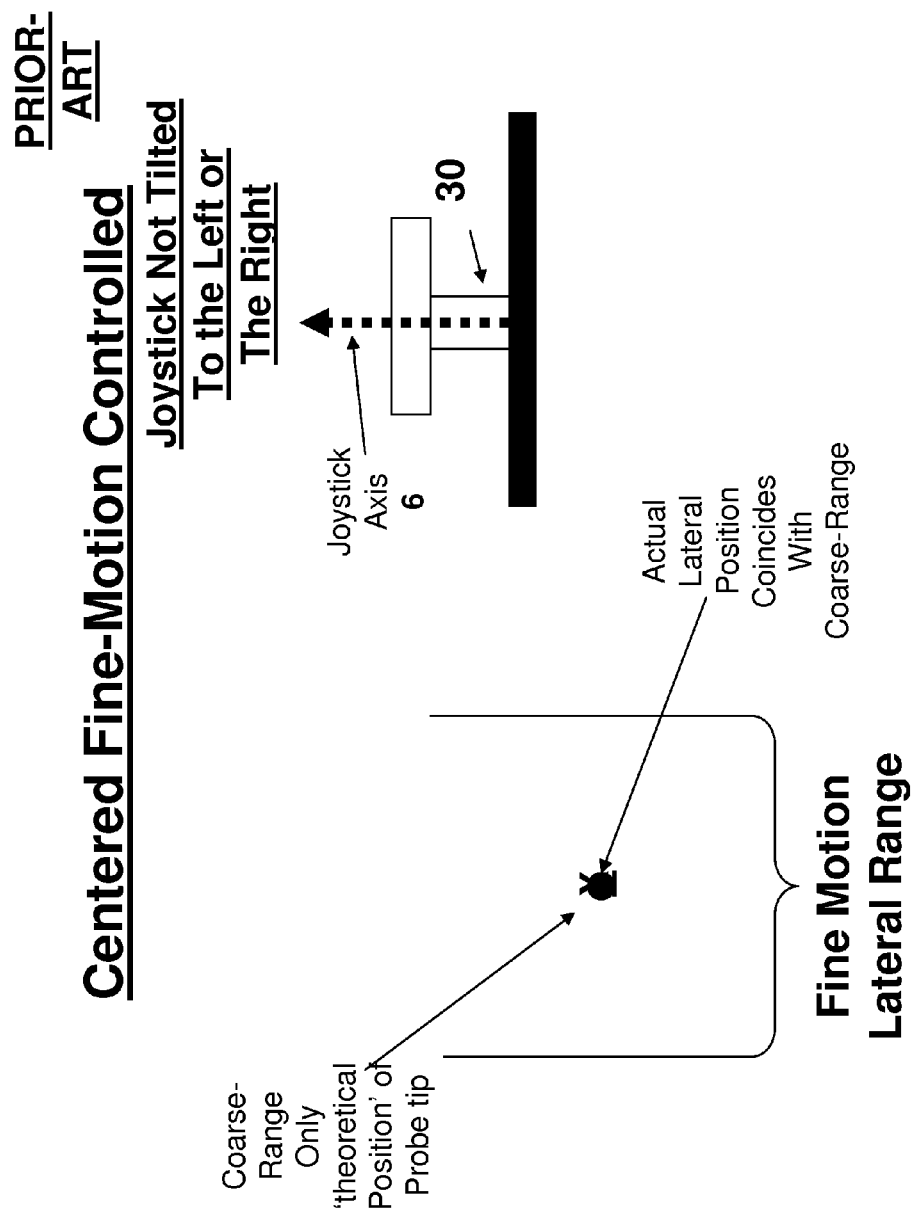
Figure 16:
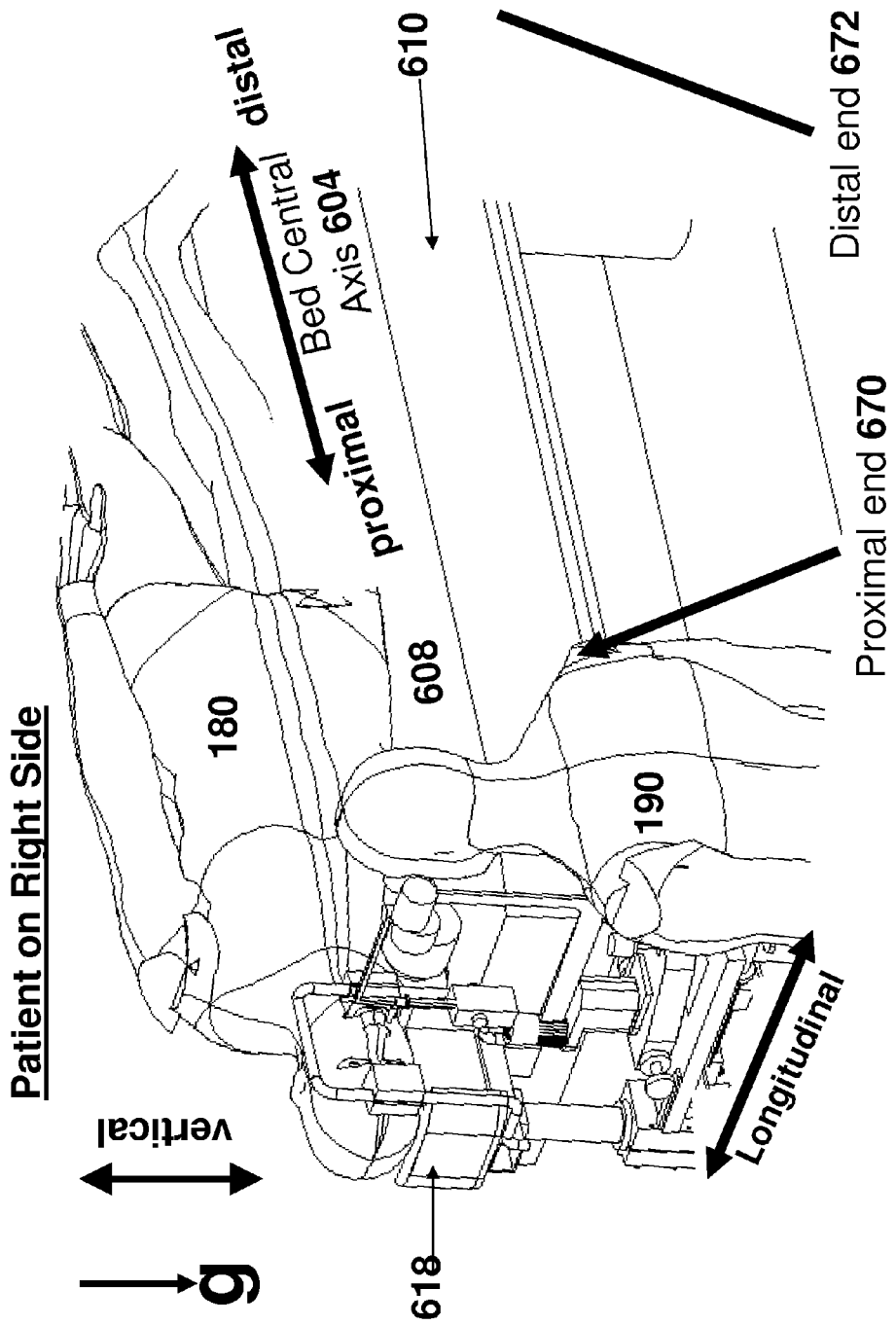
FIGS. 16-32 describe eye examination methods and/or tonometry apparatus and slit lamp apparatus and/or related apparatus according to some embodiments.
Figure 17:
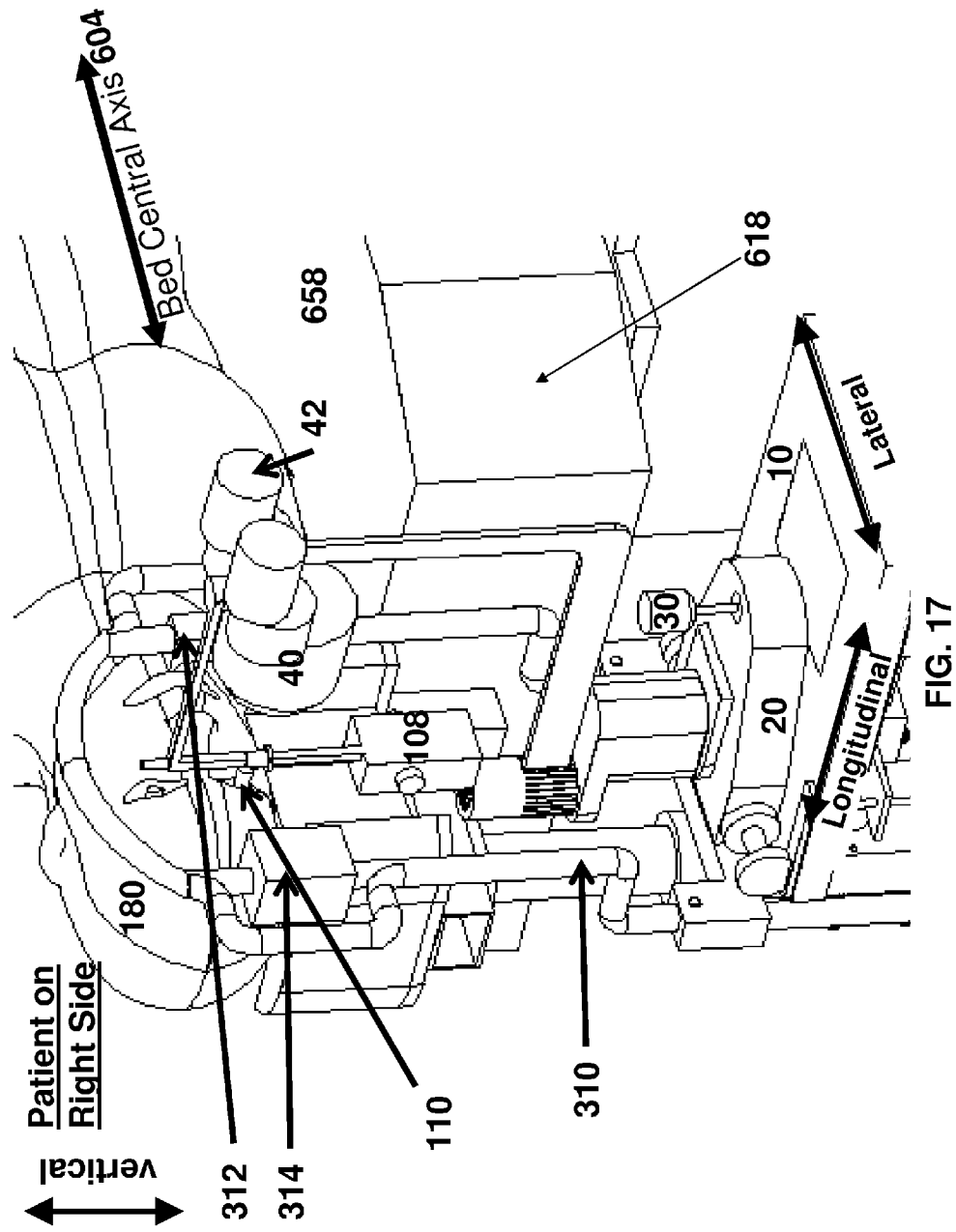

One example of 'side-lying eye examination' is illustrated in FIGS. 16-17, where a side-lying patient rests his body on bed surface 610 and rests his head on horizontal protruding headrest 618 which is elevated above bed surface 610. Vertical 'forehead rest' and 'chin-rest' elements are provided to prevent horizontal motion along a surface of head-rest 618.

Medical attendant 190 employs Goldmann tonometry device including a microscope assembly and Goldman tonometry probe 110 that is mounted so that the probe orientation is mechanically constrained to be horizontal and so that the probe 110 points away from microscope assembly 40 at the eye of patient 180. In the example of FIGS. 16-17, an illumination system other than an illumination column is used and the device is a 'Goldmann tonometry device.' Alternatively, the Goldmann tonometry device may include a slit-lamp illumination column (see, for example, FIG. 25) in order to illuminate the patient's cornea when in contact with the distal end of tonometry probe 110.

Figure 18:
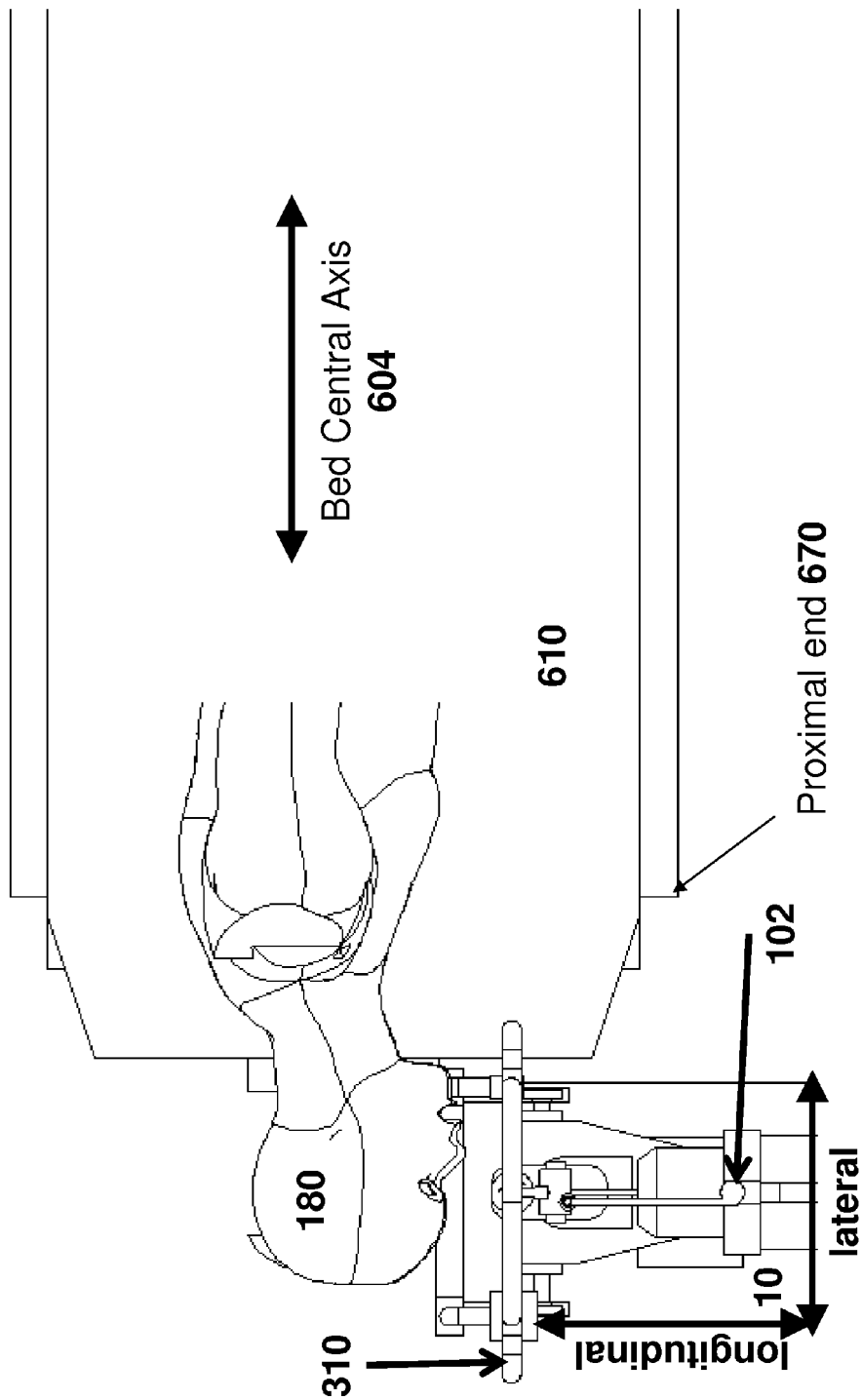
Figure 19:
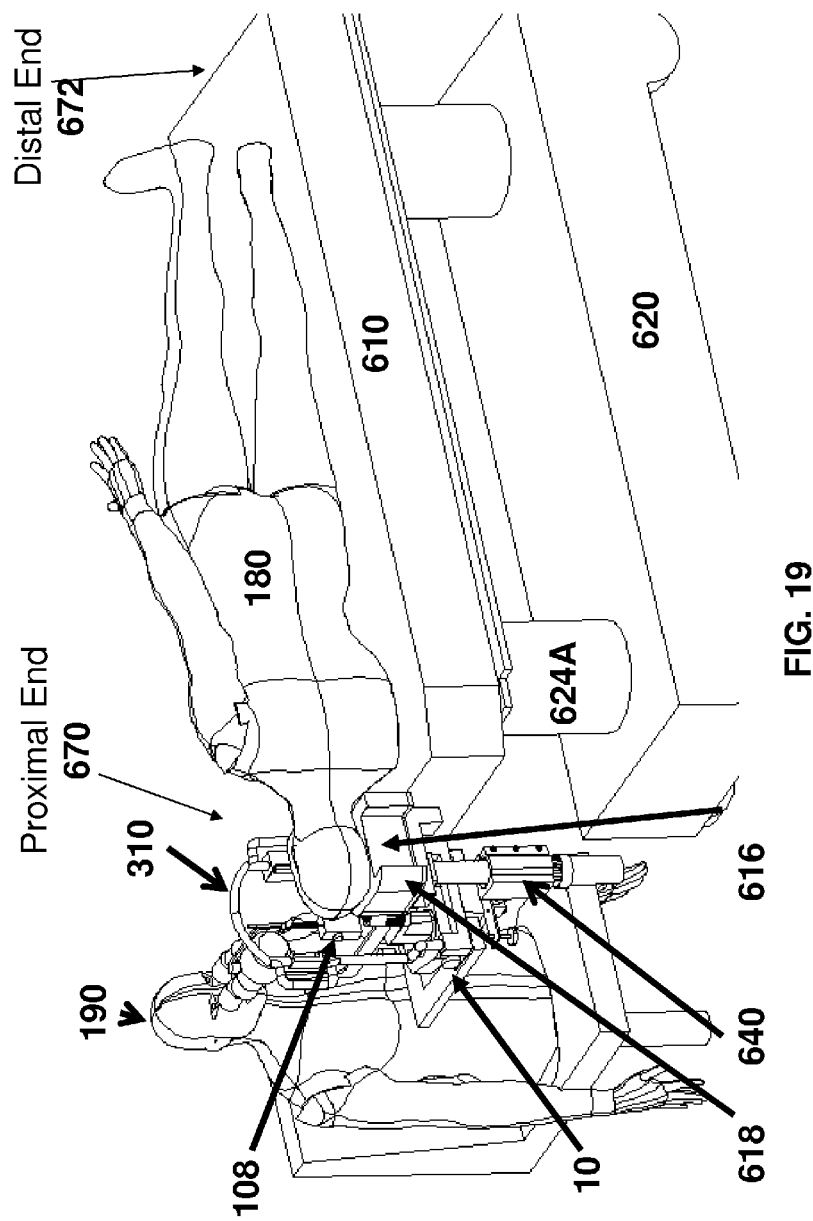

FIG. 18 illustrates a top view of a side-lying patient being subjected to a Goldmann applanation tonometry and/or slit-lamp examination. FIG. 19 is similar to FIGS. 16-18, but refers to examination of a patient 180 lying on his/her left side.

Figure 20B:
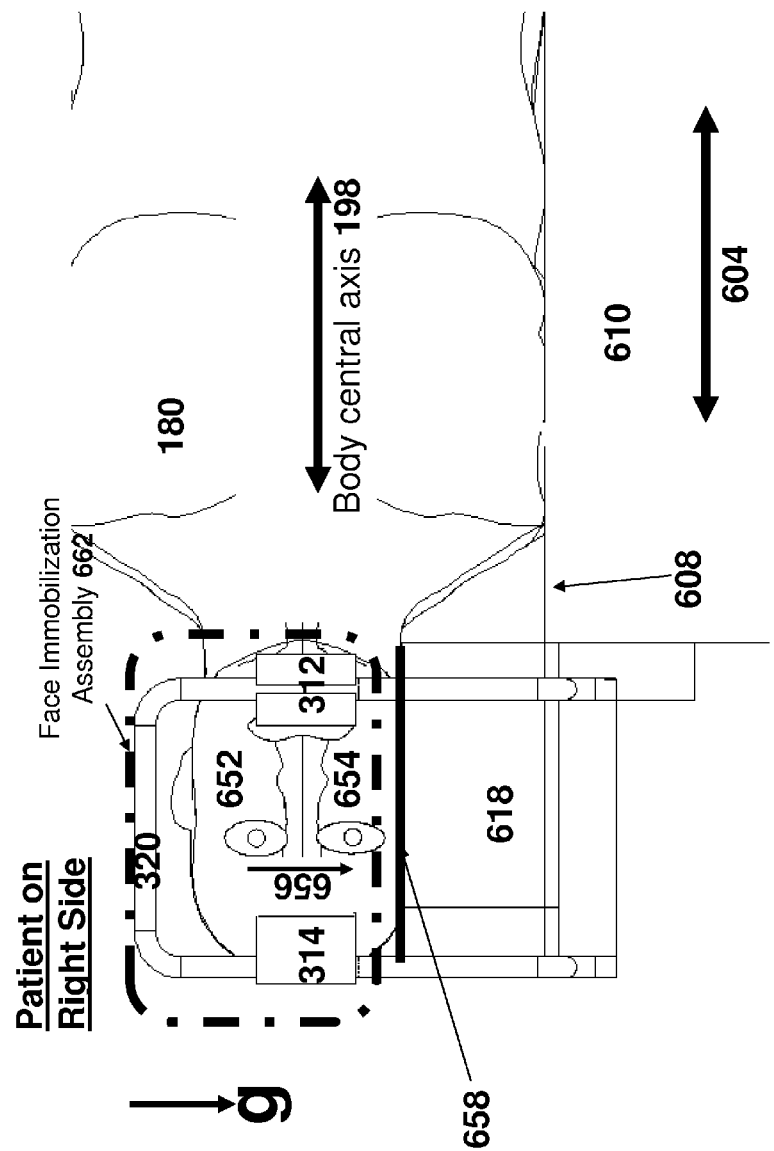

FIGS. 20A-20B illustrate immobilization of the patient's face during eye examination in accordance with some embodiments. As illustrated in FIG. 20A, laying the patient's face 'flat' on upper surface 658 of headrest 618 serves to (i) 'horizontal-orientation-immobilize' the patient's face to maintain the face in a constant substantially horizontal orientation and (ii) to 'vertically-immobilize' the face to maintain the face at a constant elevation without upward or downward motion.

This is illustrated in FIG. 20B, where 'inter-pupillary vector' (labeled as 656) is substantially vertical. FIG. 20B also illustrates the feature whereby a center of a pupil of the 'lower eye' 654 (the 'upper eye' is labeled as 652) is only slightly elevated by a length lower_eye_elevated (for example, lower_eye_elevated is at most 5 cm above, or at most 3 cm above or at most 2 cm above) above the 'horizontal face-support surface 658' which is the upper surface 658 of headrest 618.

In different embodiments, the upper 652 and/or the lower 654 eyes are subjected to a biomicroscopy and/or Goldmann applanation tonometry examination.

Another feature illustrated in FIG. 20B is the 'horizontal immobilization' of the patient's face to prevent horizontal motion and/or to prevent horizontal motion axis in the direction along the central axis of patient 198. In FIG. 20B, the 'horizontal immobilization' is provided by the presence of (i) a vertically-oriented lower-face-immobilization element 312 in contact with the patient's chin; and (ii) a vertically-oriented upper-face-immobilization element 314 in contact with the patient's forehead.

In some embodiments, as illustrated in FIG. 20C, the surface 658 vertically immobilizing is fixedly elevated at a height height_difference that exceeds the bed upper surface 608 on which the body is resting. In some embodiments, a minimum value of height_difference is at least 5 cm or at least 10 cm and/or a maximum value of height_difference is at most 30 cm or at most 20 cm. In some embodiments, a ratio between lower_eye_elevated and height_difference is at most 0.3.

Some embodiments relate to subjecting a side-lying patient to a Goldmann tonometry examination using a slit-lamp mounted Goldmann tonometer and/or a Goldmann tonometer device that lacks an illumination constant.

Some embodiments relate to subjecting a side-lying patient to a biomicroscopy examination using a slit-lamp (e.g. including an illumination column). In these embodiments, there is no requirement to carry out any tonometry examination.

Goldmann Tonometry Devices

In some embodiments, the Goldman tonometer device includes a Goldmann tonometer assembly mounted to a slit-lamp device and/or part of a 'hybrid biomiscropy device' (see, for example, FIG. 25). In other embodiments, an illumination source other than a slit lamp light and/or other than an illumination column is provided (see, for example, FIG. 32 and the accompanying discussion).

Thus, in contrast to conventional systems where a presence of a slit lamp and/or illumination column is required, this is not a requirement.

A 'Goldmann tonometry device' is any device that includes a mounted horizontally-constrained tonometry probe that is mechanically constrained in a horizontal orientation.

In different embodiments, the 'Goldmann tonometry device' may provide any combination of the following features:

(i) an applanation tonometry probe that is mounted so that an orientation of the tonometry probe (i.e. the orientation of a central axis 114) is mechanically constrained (i.e. according to the 'mounting') to be horizontal or nearly horizontal;

(ii) an applanation tonometry probe mounted 'in the air' without resting on a tabletop or other flat surface;

(iii) a connecting element (e.g. probe arm 106) between an applanation probe 110 and a spring-loaded controller 108 such that the applanation probe and the container do not reside in the same housing—e.g. probe and a container of the controller 108 are horizontally and/or vertically distanced from each other (e.g. by at least several cm);

(iv) a microscope assembly 40 (e.g. a Gallilean microscope having a monocular or binocular eyepiece 42) that moves horizontally and/or vertically in-tandem with the mounted tonometry probe;

(v) a tonometry probe 110 (and in some embodiments, a spring-loaded controller container 108) mounted to (and at a higher elevation of) an upper base 20 or carriage or platter that is movable (i.e. slidable or glidable or rollable or otherwise movable) over the lower base 10. Although in some embodiments the upper base 20 or carriage or platter moves over lower base by means of wheels, there is no requirement of wheels, and none of the terms (a) upper base (b) carriage and (c) carriage requires a presence of wheels;

(vi) Typically, there is some sort of significant resistance to movement of upper base 20 over an upper surface of a lower base 10—for example, due to a heavy weight of upper base 20 (e.g. having a weight that is at least 2 kg or at least 3 kg or at least 4 kg or at least 5 kg) and/or a combination of upper base 20 and elements mounted to and supported by upper base 20 (e.g. the combination of elements has a weight that is at least 4 kg or at least 5 kg or at least 6 kg or at least 10 kg or at least 15 kg);

(vii) 'in-tandem' horizontal motion of applanation probe 110 together with (i.e. any combination of) upper base 20 and/or microscope assembly 40 (e.g. including monocular or binocular microscope eyepiece 42) and/or slit lamp light 70 and/or illumination column and/or optical elements 80. In some embodiments, a joystick 30 (e.g. a joystick whose 'central stick orientation' is generally upwards and/or a joystick mounted to upper case 20) is provide to induce and/or regulate the horizontal motion. In some embodiments, the joystick controls 'fine motion' while another mechanism of controlling 'coarse motion' (e.g. manually moving upper base 20) is provided;

(viii) a microscope assembly 30 which receives light from the tonometry probe and/or which is horizontally displaced from a proximal end of tonometry probe (e.g. at a time of normal operation so that the probe is in contact with a cornea of the patient) by at least 10 cm or at least 15 cm or at least 20 cm) and/or does not reside in a common housing from with tonometry probe.

(ix) 'in-tandem vertical motion' between applanation tonometry probe 110 and microscope 30 relative to lower base—for example, regulated by any mechanical or electrical or motorized controller(s). In some embodiments, twisting of a stick of a joystick 30 about its axis controls the 'in-tandem vertical motion' to raise or lower applanation tonometry probe 110.

Goldmann Tonometry Measurements

In some embodiments, both an upper and a lower eye are subjected to a TOP measurement by a Goldmann tonometry device. In other embodiments, it is possible to subject one or both eyes to the TOP measurement.

A 'sidelying position' refers to the situation where the patient's body or a significant portion thereof 'below the neck' is lying sidewards.

Other embodiments may refer to the case where at least the patient's head is oriented sideways so that an inter-pupil vector 656 between the patient's pupils is substantially co-linear with a gravitation vector—for example, when the patient is 'lying down' in a prone or supine position.

In some embodiments, an adult is subjected to the measurements, where the adult's face is characterized by one or more (i.e. any combination of) the following features: (i) an inter-pupillary distance that is at least 7 cm; and/or (ii) a distance between a chin and a head top that is at least 15 cm or at least 20 cm.

In some embodiments, it is possible to (i) first measure (i.e. using the same Goldmann tonometry device) the TOP of one or more of the eyes when the patient is in one of a 'left lying' and 'right lying' positions and (ii) then to measure the TOP of one or more of the eyes when the patient is in the other of the 'left lying' and 'right lying' positions.

A Brief Description of 'Bed Features' 610

Figure 23:
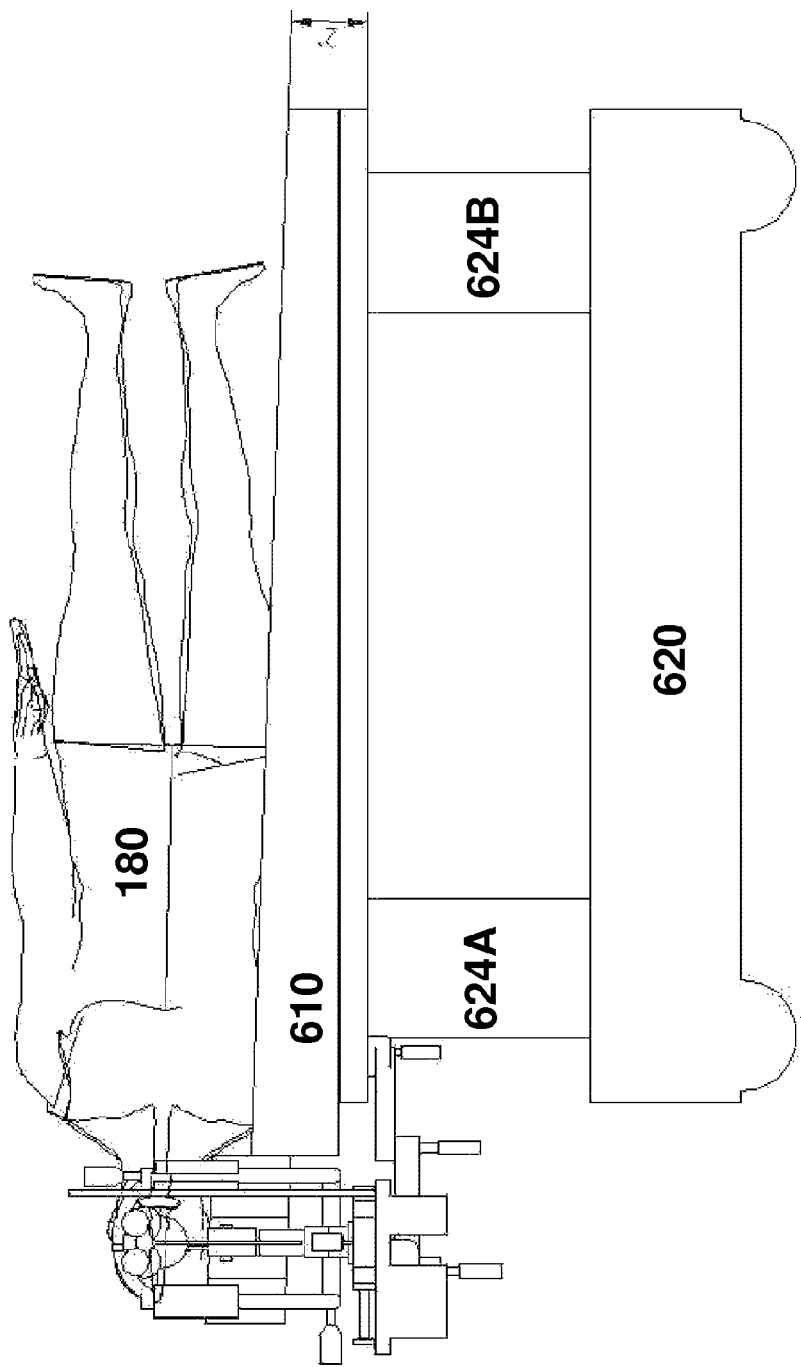

In some embodiments, a bed 610 may be provided. The bed may provide any of the following features (i.e. any combination of one or more of the features):

a) the bed upper surface 608 is generally flat—either completely flat or possibly tilted (see, for example, FIG. 23);

b) the bed upper surface 608 is dimensioned to support an adult human or a significant portion (e.g. at least half) thereof;

c) in some embodiments, the bed surface 608 has a width of at least 30 cm and/or at least 40 cm and/or at least 50 cm and/or at least 60 cm;

d) in some embodiments, the bed surface 608 has a length of at least 0.75 and/or 1 and/or 1.25 and/or 1.5 meters and/or at least 1.5 times the width and/or at least 2 times the width;

e) in some embodiments, the bed surface 608 has a surface area of at least 5,000 cm^2 and/or at least 7,500^2 cm and/or at least 10,000 cm^2 and/or at least 15,000 cm^2.

In various locations in the disclosure, a bed is labeled as 610, a bed upper surface is labeled as 608, a bed central axis is labeled as 604, a bed proximal end is labeled as 670, and a bed distal end is labeled as 672.

A Brief Description of Headrest 618 Features

Various embodiments provide a 'head-rest' 618. In some embodiments, this headrest 618 is attached to bed 610.

Figure 21A:
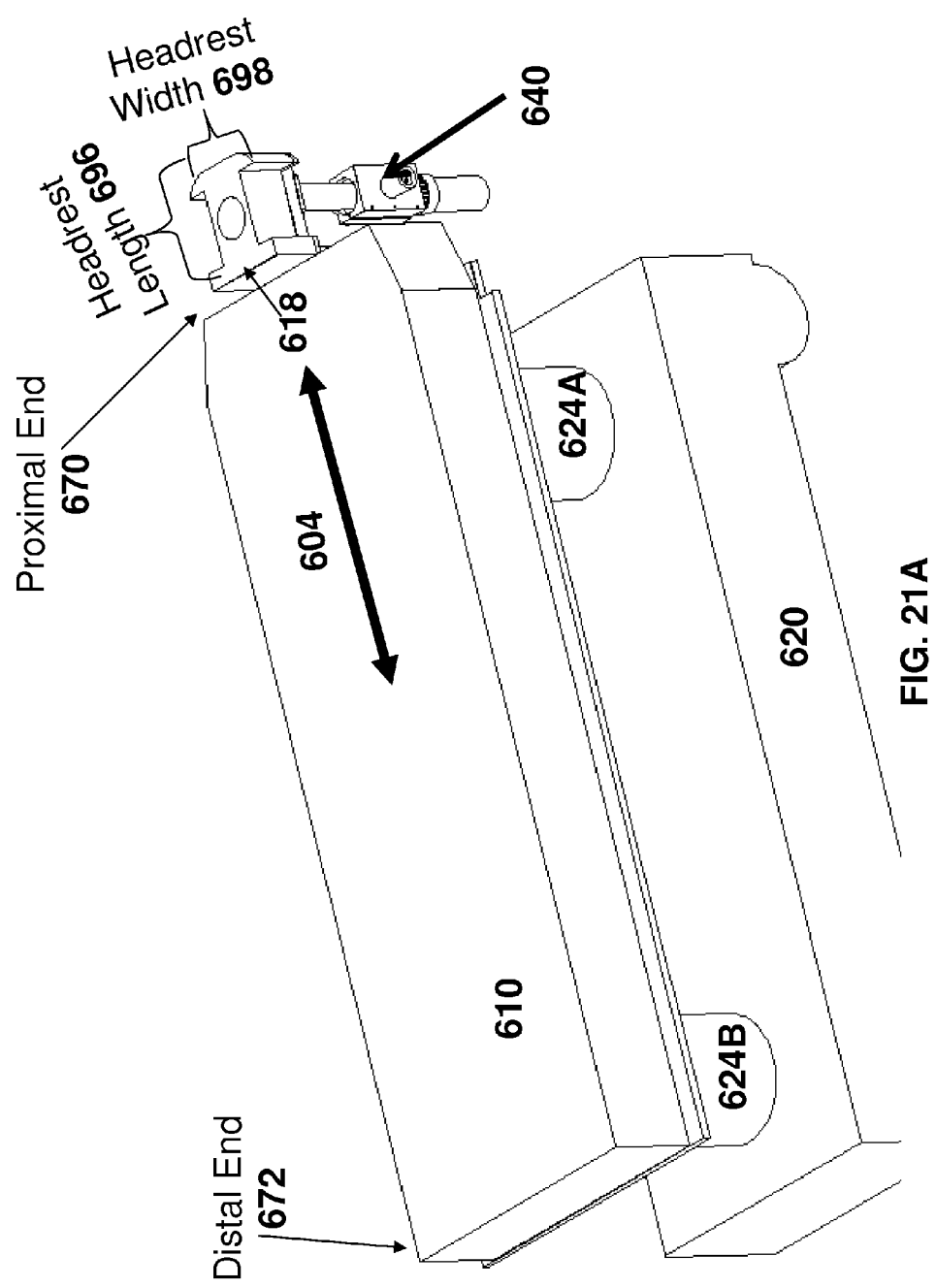

This headrest 618 may be mounted to a Goldmann tonometry device base 10 (see, for example, FIG. 25) or may be attached to or mounted to bed 610 (see, for example, FIG. 21).

In some embodiments, an upper surface 658 of this 'head-rest 618' is significantly smaller than the bed upper surface 608—for example, by a factor of at least 5 or at least 10, or at least 20 or at least 30.

Figure 21B:
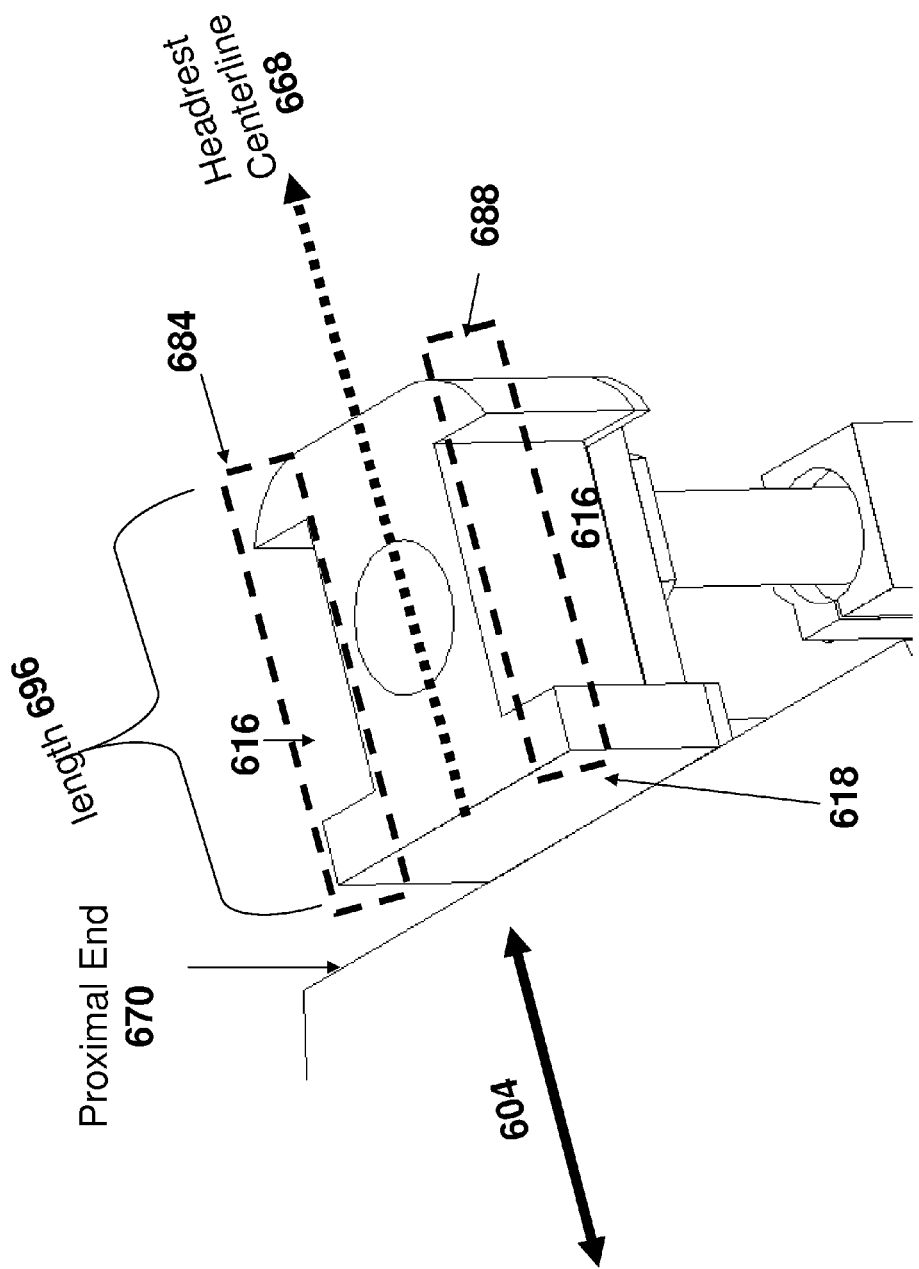

As will be discussed below, and referring to FIG. 21B, in some embodiments, the headrest includes a notch or 'indentations' 616 of that is at or near one of the edges 684 or 688 (for example, edges that generally are parallel to head rest centerline 668 and/or to bed elongate axis 604). In the example of FIG. 21, these indentation regions or notches 616 are provided on both edges in parallel. In other embodiments, it is possible to provide no indentation region or an indentation region only in one edge region.

The function of the notch is to provide a free space that can be occupied by tonometer controller container 108 during examination—see FIG. 17 where at least a portion of container 108 is within indentation 616.

In the figures, the 'length' of headrest 618 is labeled as 696, the 'width' is labeled as 698, and the thickness is labeled as 694. Clearly the length and width are substantially horizontal and perpendicular to each other.

In different embodiments, the 'length' is the dimension of headrest 618 in a direction that is (i) parallel to bed axis 604; and/or (ii) parallel to an upper face immobilizer element 310 of face immobilization assembly 662 and/or (iii) parallel to a line segment connecting chin 312 and forehead immobilizer 314; and/or (iv) perpendicular to a direction of applanation tonometer probe 110 during normal operation of the device and/or (vi) parallel to a 'lateral dimension' of a tabletop of lower base 10 over which (in FIG. 24C, and in any embodiment, this may be the 'smaller dimension' of the tabletop) upper base or carriage 20 moves and/or (vi) perpendicular to a 'normal configuration direction' of a monocular or binocular eyepiece 42 of microscope assembly 40; and/or (vii) a direction of an edge (684 or 688) within which there is an indentation 616 for tonometer control container 108.

The 'width' of the headrest is the dimension of the headrest in a dimension perpendicular to the length dimension.

In some embodiments, both of the length and the width are at least 7.5 cm and/or at least 10 cm and/or at least 15 cm.

In different embodiments, the 'length' of headrest is at least 20 cm and/or at least 25 cm and/or at least 30 cm.

In different embodiments, the 'width' of headrest is at least 10 cm and/or at least 15 cm and/or at least 20 cm—i.e. enough to accommodate and vertically immobilize a side of a patient's head.

In some embodiments, headrest 618 includes an indentation 616—for example, in a illustrated in FIGS. 21A-21D. In those figures, indentation region 616 is along an edge 684 and/or 688 that is parallel to a bed central axis 704. Although respective indentation regions along each edge appear in various figures, this is not a limitation.

Figure 21D:
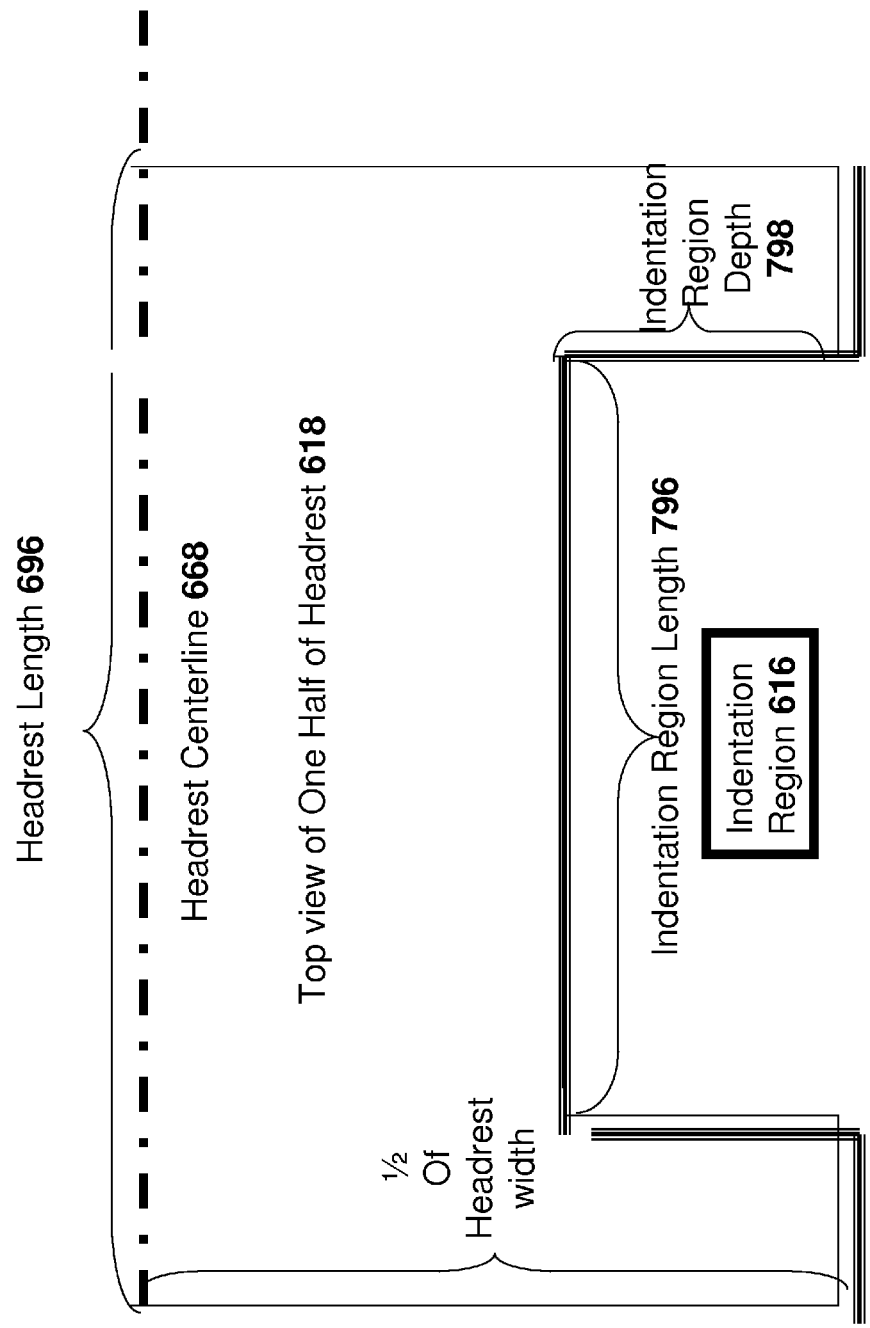

FIG. 21D illustrates the lengths 796 (i.e. in the horizontal direction parallel to a bed central axis 704) and depth 798 of one non-limiting example of an indentation region. Although the indentation region in FIG. 21D is illustrated as rectangular, this is not a limitation. In embodiments, at least a portion of container 108 of Goldmann tonometry assembly is located within the indentation region Face Immobilization Assembly 662

Figure 24A:
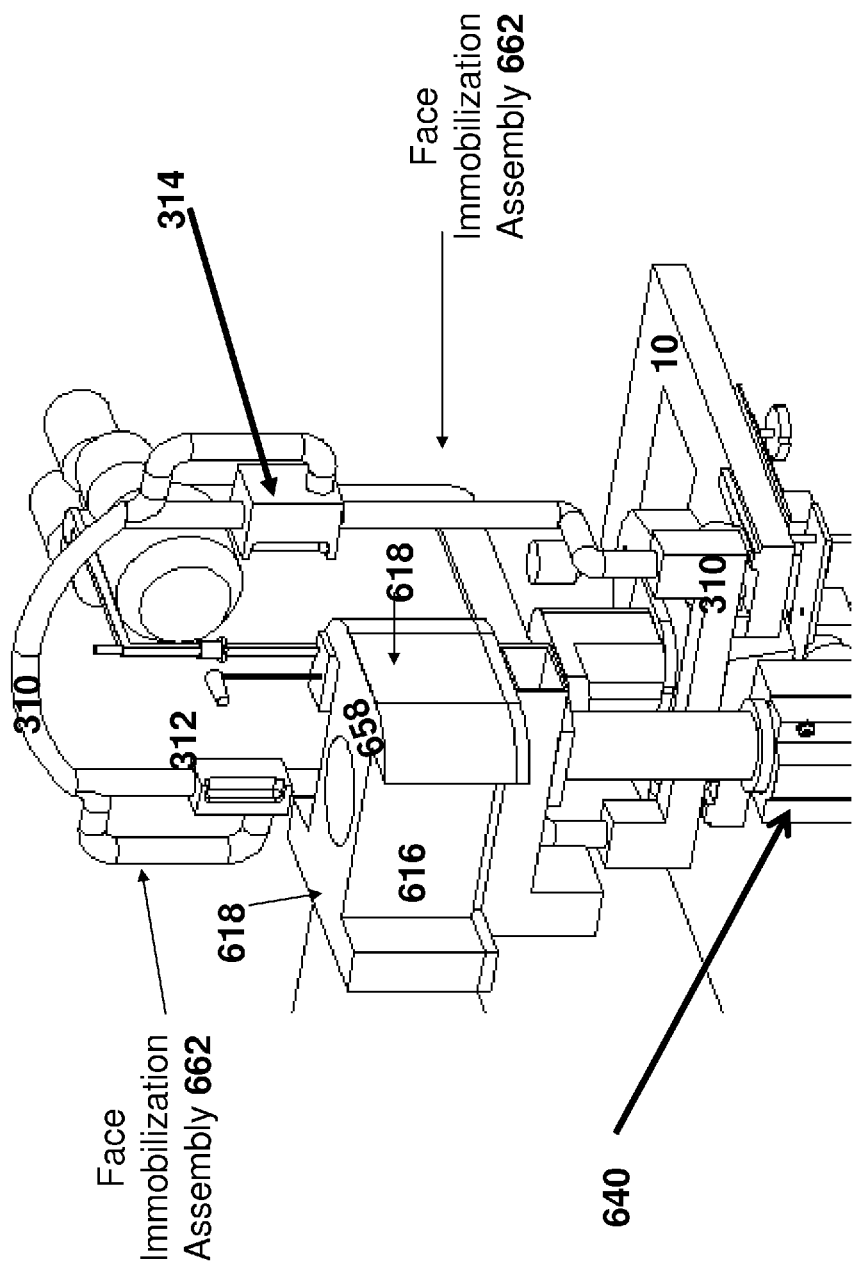
Figure 24B:
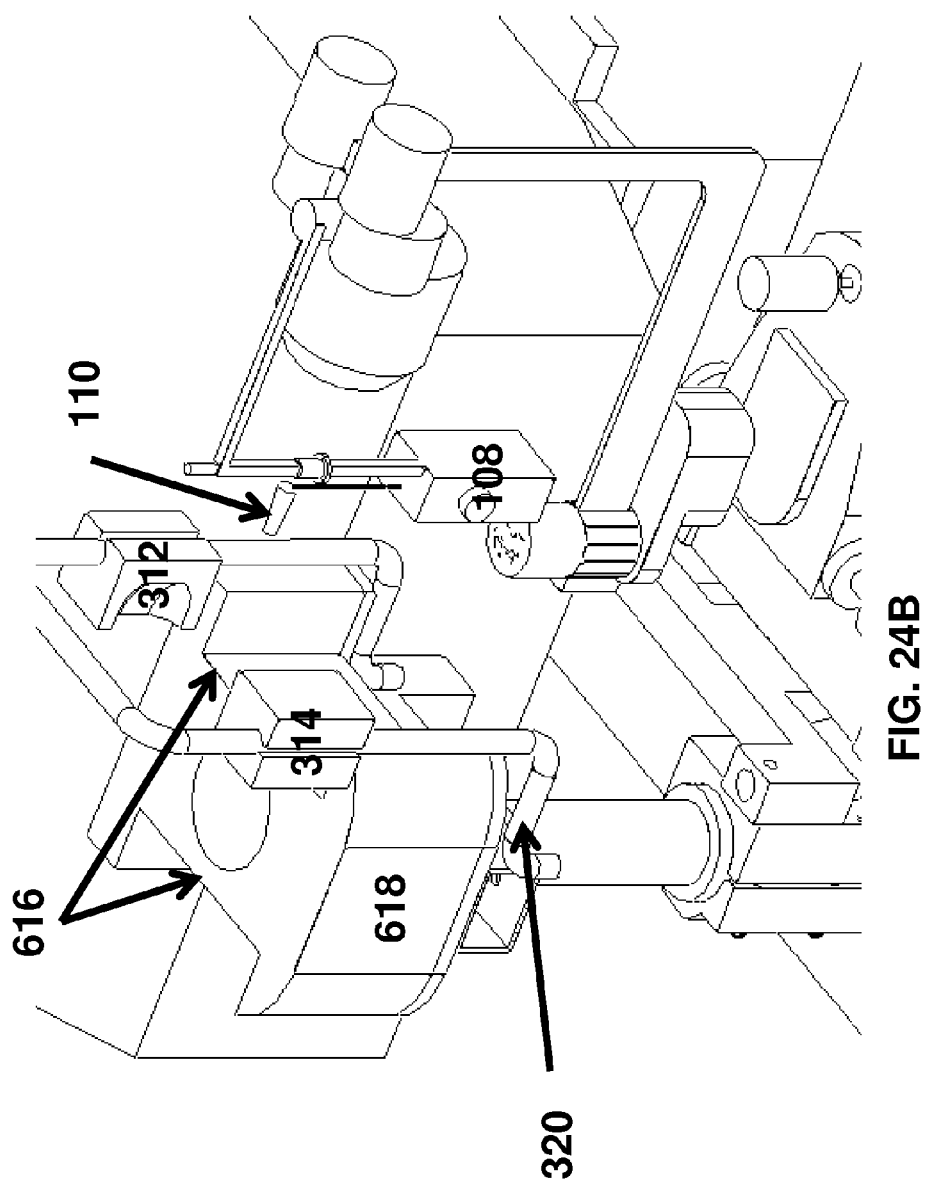
Figure 25A:
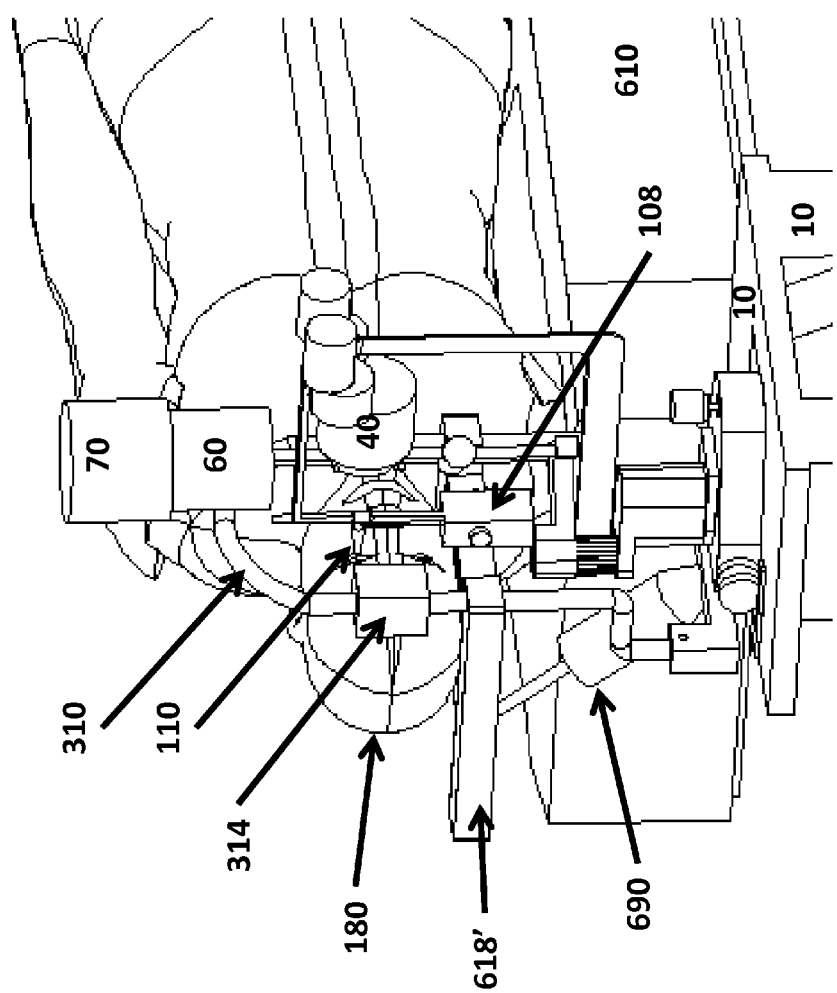
Figure 25B:
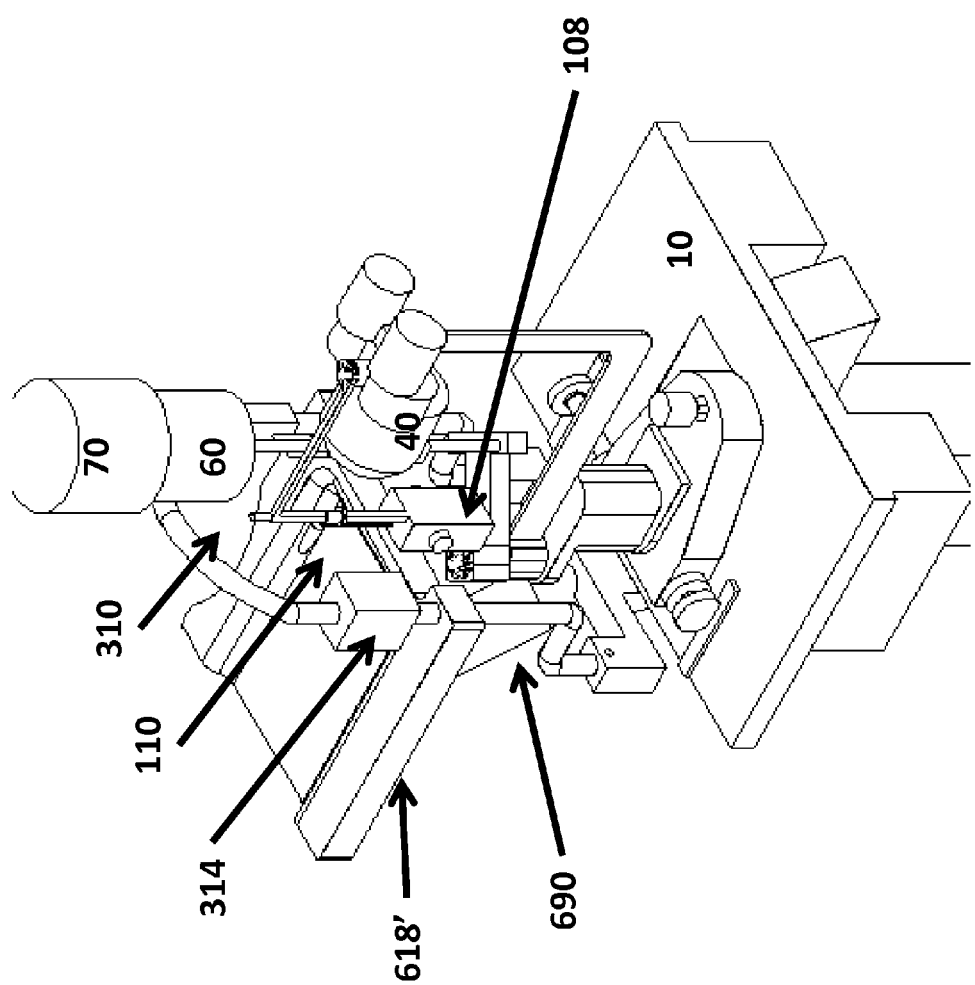
Figure 25C:
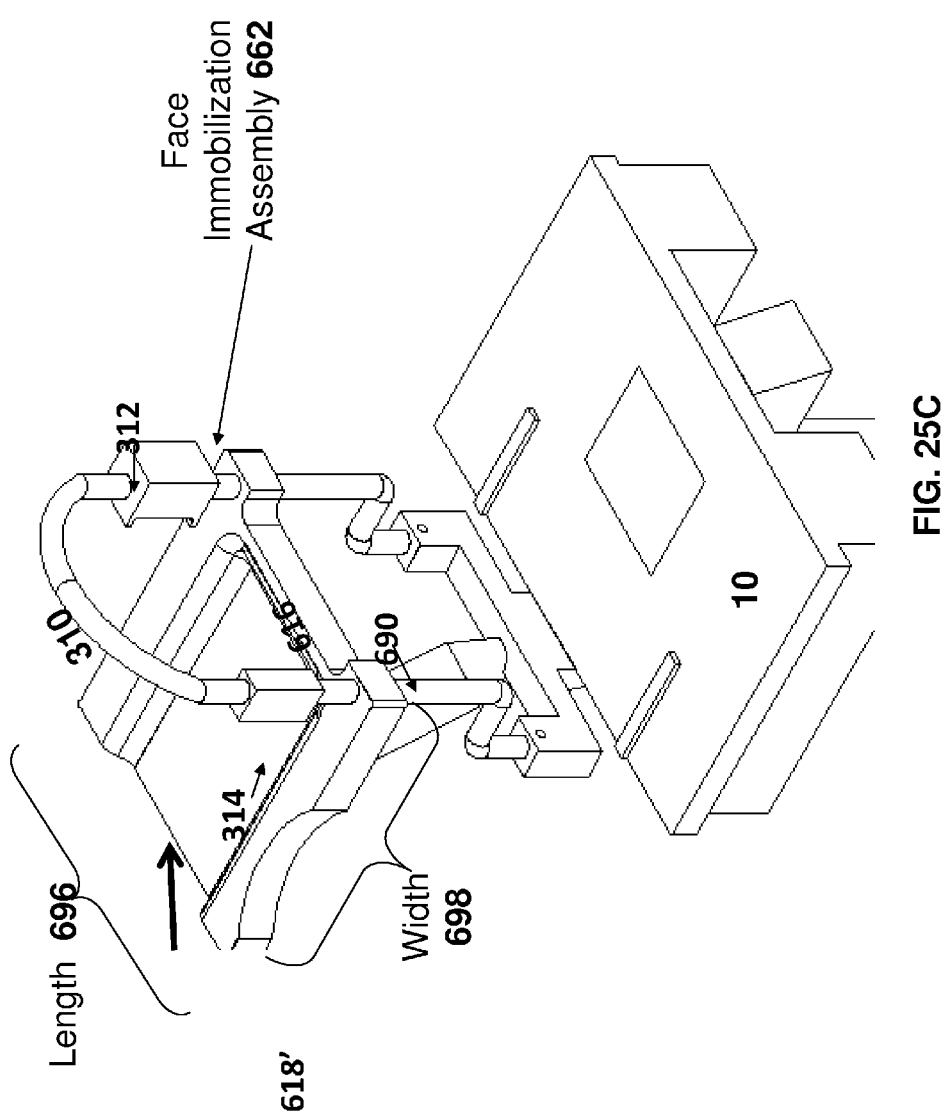
Figure 25D:
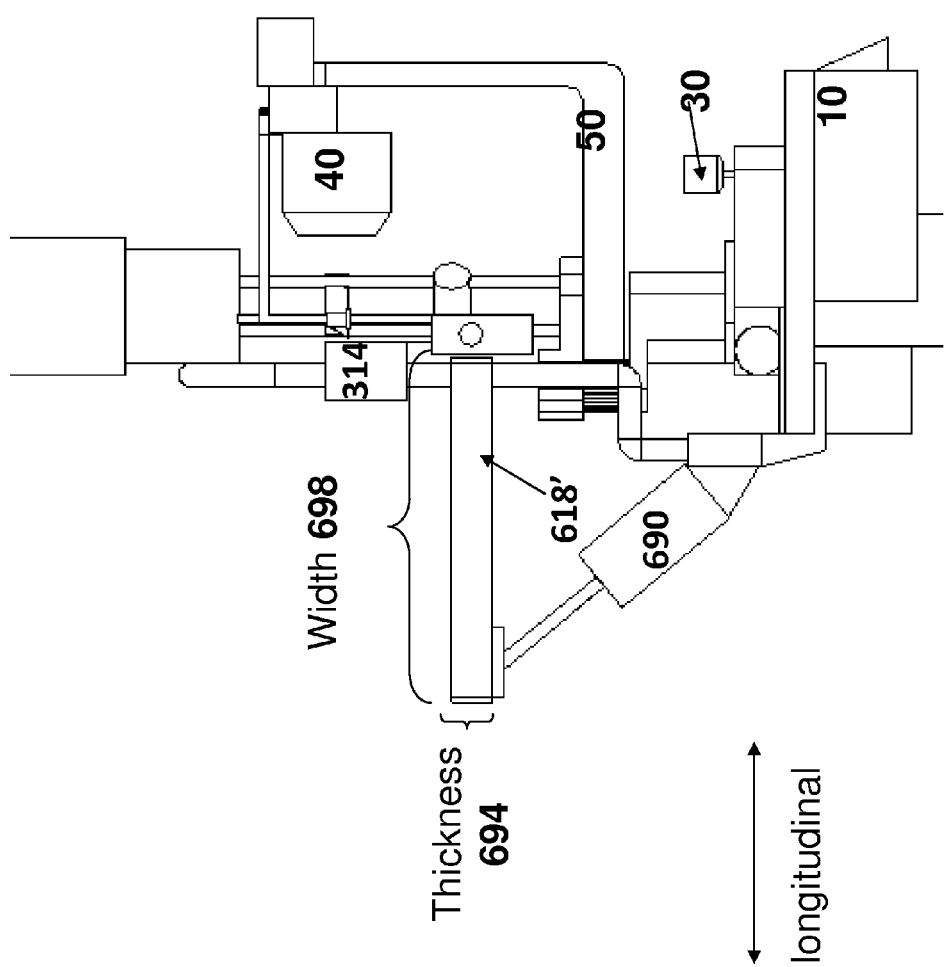

In some embodiments, headrest 618 (i.e. for example, attached to or localized to a proximal end 670 of bed 610 as in FIG. 24 or mounted to a base of a slit lamp and/or to a base of tonometry device as in FIG. 25) may be coupled attached to or brought into near contact or actual contact with a face immobilization assembly 660. When the patient's head is vertically immobilized and held to a constant orientation by an upper surface 658 of headrest 618, face immobilization 662 serves (e.g. in cooperation with headrest 618) to prevent horizontal motion of the patient's head to 'horizontally immobilize the patient's head.

Figure 22A:
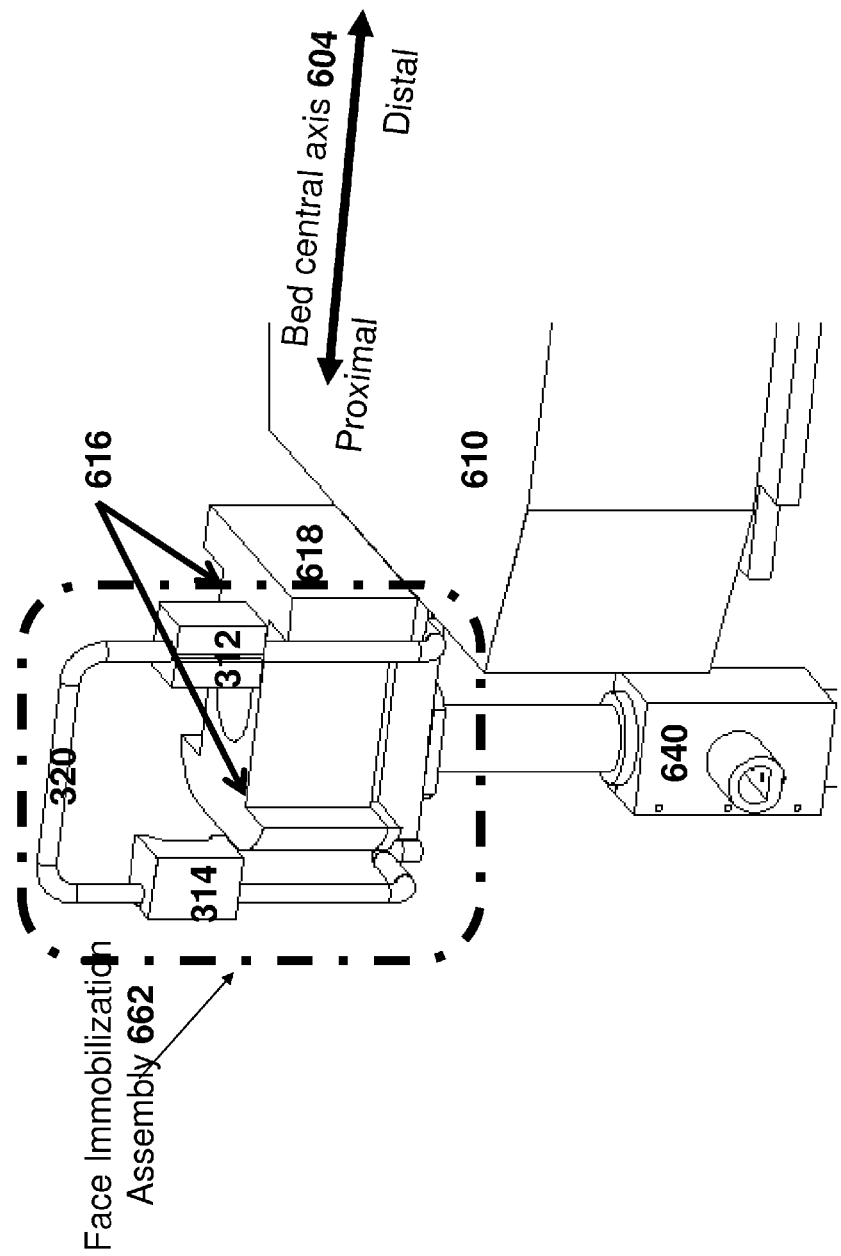

In some embodiments, face immobilization assembly 662 (see, for example FIG. 20B or FIG. 22A or FIG. 22C) includes a plurality of vertical elements 312 and 314 which (i) are rigid or include a rigid portion (e.g. for example, 'tubes' such as 'metal tubes'); (ii) are rigidly connected to each other and (for example, via a rigid upper horizontal element 310 such as a rigid tube).

Face immobilization assembly 662 is configured to 'frame an infinitely thin region of space (i.e in 2 dimensions) having a height (e.g. at least 8 cm or at least 10 cm or at least 15 cm) and a length (e.g. at least 20 cm or at least 22.5 cm or at least 25 cm or at least 27.5 cm or at least 30 cm) to an immobilized sideways-oriented human head (e.g. adult) located at a location of the 'frame region.'

Some embodiments (see, for example, FIG. 22) relate to an apparatus including a bed 610, a headrest 618 mechanically coupled to the bed at or near a proximal end 670 of bed 610, and a face immobilization assembly 662 which (i) in a first configuration, is rigidly attached to the headrest 618 at first edge 684 and (ii) in a second configuration, is rigidly attached to the headrest 618 at a second edge, the edges being on opposite sides of headrest 618 and parallel to each other.

In FIG. 22, it is possible to snap down and/or face immobilization assembly 662 from headrest and then to redeploy on the other side and/or on an opposing edge of headrest 618. Alternatively, it may be possible to rotate the face immobilization assembly 662 between positions.

Probe Range—Tonometer

In some embodiments, a joystick 30 (for example, a dual-use joystick) or any other 'vertical motion controller' is operative to vertically move horizontal-motion-constrained probe 110 relative to a slit lamp base 10. This vertical motion may be 'in-tandem motion' of probe 110 together with any combination of (i.e. one or more of) (i) microscopy assembly 40 (and/or with monocular or binocular eyepiece 42—for example, an eyepiece 42 whose orientation is constrained to be horizontal) and/or (ii) a top of base column 22 and/or (iii) a passive optical component (e.g. 80) for controlling a height of a horizontal beam of light directed toward probe 110.

As noted above, in some embodiments, it is possible to (i) first measure IOP of one of an upper eye and lower eye and (ii) then to measure IOP of the other of the upper eye and a lower eye. Thus, in some embodiments, a 'large vertical range' control may be provided to induce in-tandem vertical motion of horizontally-orientation-constrained applanation probe 110 and one or more additional elements (e.g. microscope assembly 40). This 'large vertical range' will exceed an average interpupillary distance of a significant portion of the adult population—for example, the 'large vertical range' may be at least 6 cm or at least 7 cm or at least 8 cm or at least 9 cm In some embodiments, this is a 'dual mode' joystick for inducing and/or controlling horizontal motion by tilting the joystick. In these embodiments, twisting a stick of the joystick provides the 'larger vertical range'.

Figure 26:
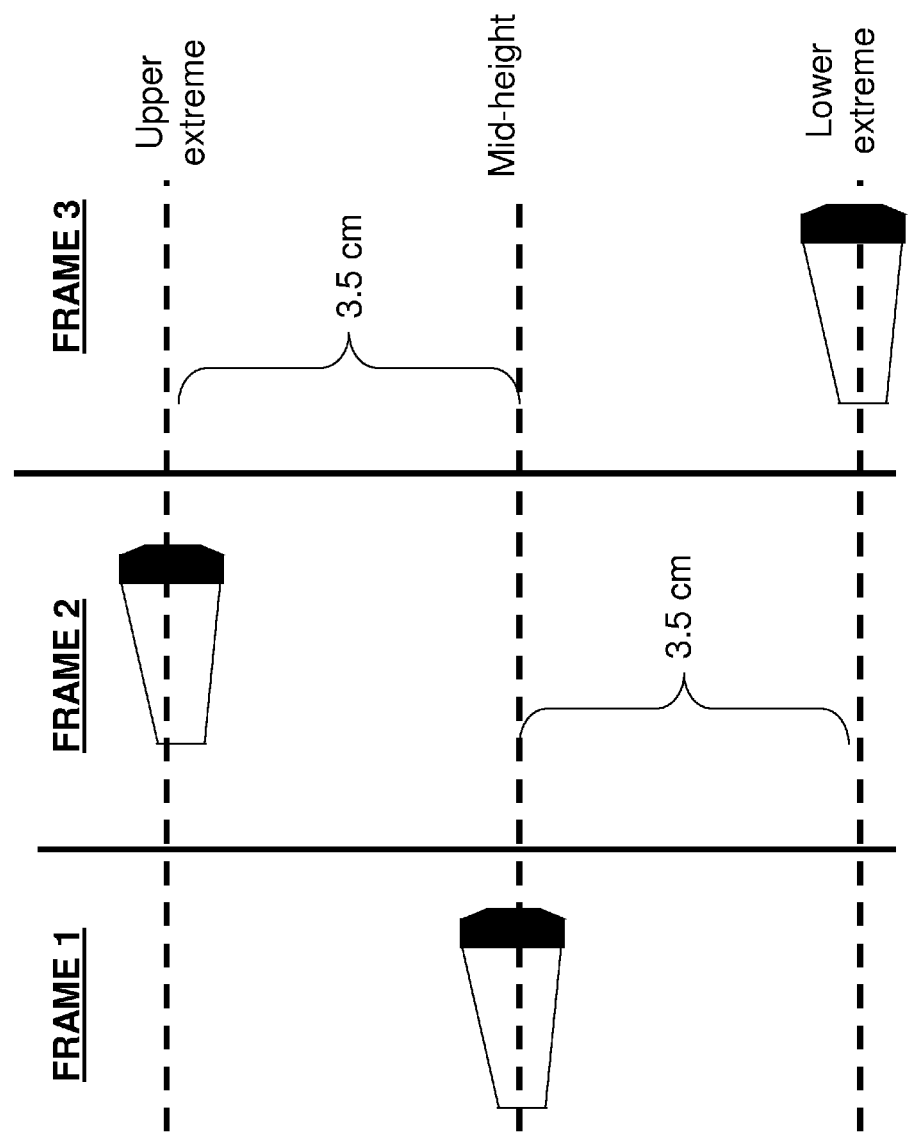
Figure 27A:
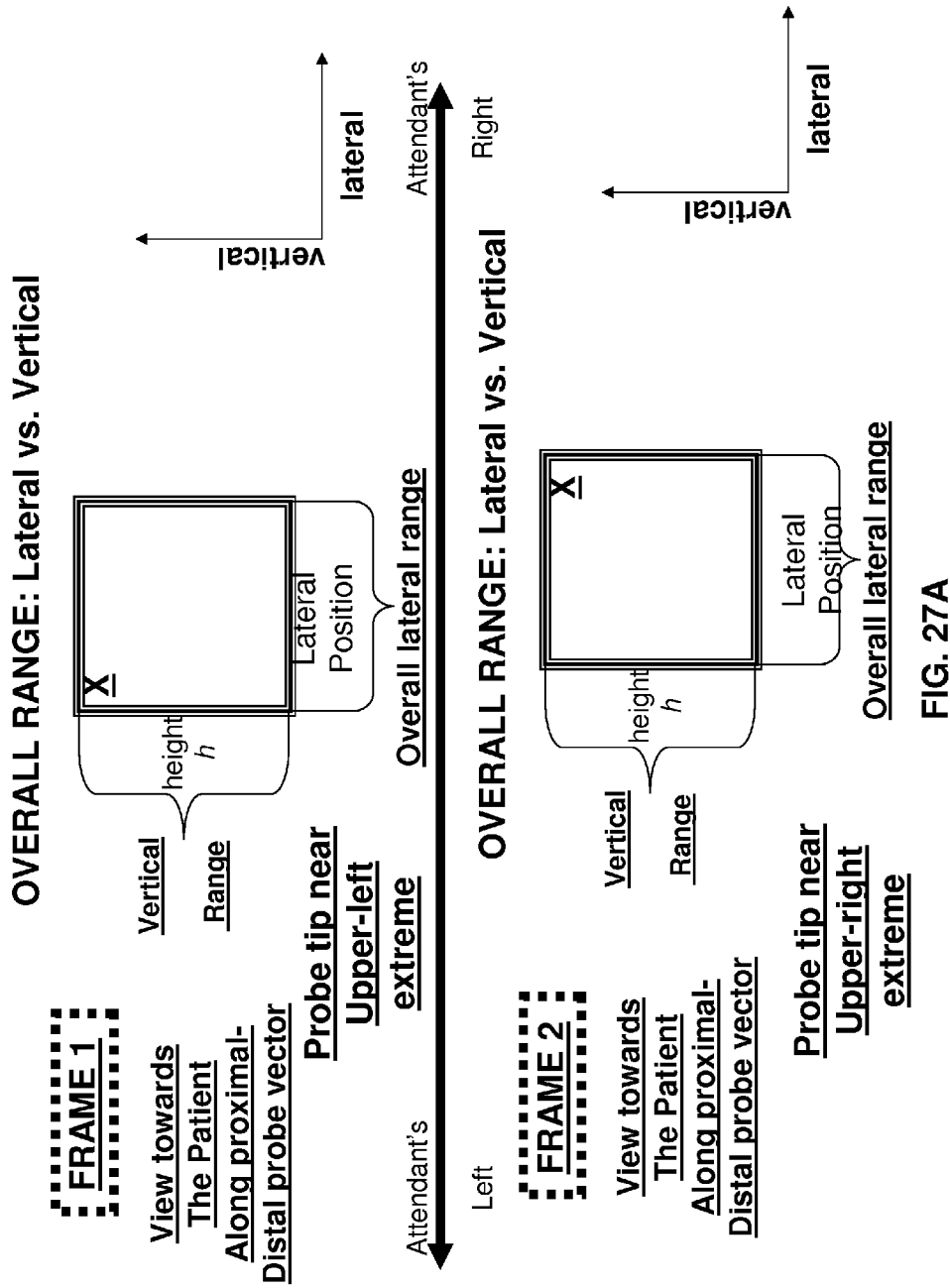
Figure 28A:
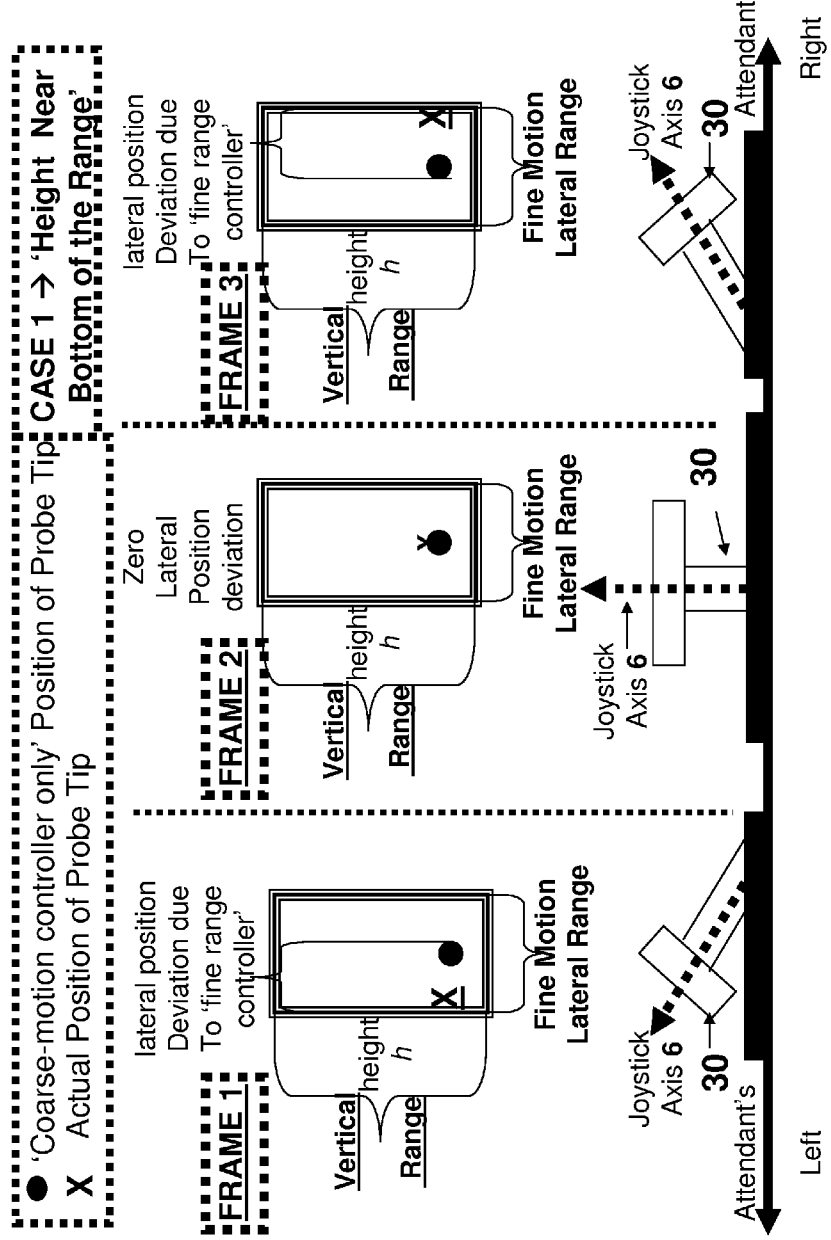
Figure 28B:
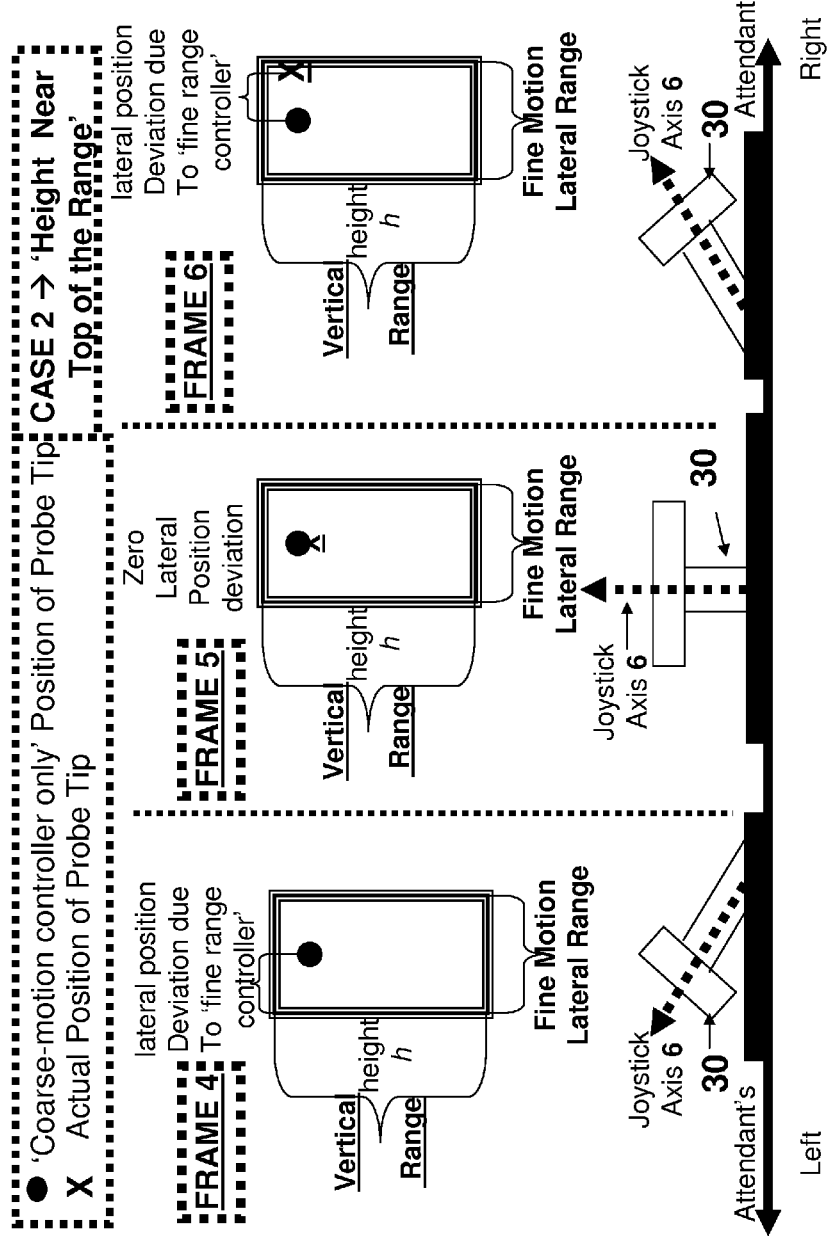

The case of '7 cm' is illustrated in FIG. 26. FIGS. 27-28 provide non-limiting examples of ratios between the vertical range and other ranges. For example, as illustrated in FIG. 27, the vertical range may be at least 0.75 or at least the same as or at least 1.2 times or at least 1.4 times the lateral range.

FIG. 28 provides another example of relative ranges.

Probe Range—Slit Lamps

In some embodiments, a larger vertical range (e.g. at least 7 cm or any other number mentioned above in the contact of Goldmann tonometry devices) may be provided.

As noted in the background section, some slit lamp devices (e.g. with or without Goldmann tonometers) include passive optical element(s) (e.g including a reflector or minor angled at 45 degrees from the horizon) for re-directing substantially vertical light from slit-lamp light 70 into a horizontal direction at a given 'height.' This height may be regulated, for example, by twisting a stick of a joystick.

It is now disclosed for the first time a slit lamp device comprising: a. a lower base 10; b. an upper base 20 movable over the lower base 10; c. a microscope assembly 40 mounted onto the upper base 20 to provide in-tandem horizontal motion of the upper base 20 and the microscope assembly 40 over the lower base 10, d. an illumination column including a slit-lamp light 70 configured to emit an intense thin beam of light in a substantially vertical direction; e. passive optical component(s) 80 configured to re-direct the optical intense thin beam of light into substantially a horizontal direction away from the microscope, such that when the re-directed beam of light is incident upon a location of a reflective vertical plane, light of the re-directed beam is backwardly reflected towards microscope assembly 40 such that the location of the vertical plane is in a field of view of the microscope assembly, e. a dual mode joystick configured: i. to regulate and/or to induce the in-tandem horizontal motion by titling of a stick of the joystick; and ii. to induce in-tandem vertical motion of the microscope assembly and the horizontal beam re-directed by twisting the stick of the joystick around its axis, the vertical motion of the horizontal beam modifying a height of a location in the field of view of the microscope, wherein a vertical range of the induced in-tandem vertical motion provided by the twisting of the stick of the joystick is at least 7 cm.

Constraining Motion

Some embodiments relate to constraining motion of a slit lamp and/or Goldmann tonometry device. For example, a bed or any other object may limit or 'constrain' a motion of Goldmann tonometer device and/or a slit lamp device (i.e. the entire device or any part thereof such as weight-bearing lower base 10 or a portion thereof) by preventing translational or rotational motion of the Goldmann tonometer and/or slit lamp device from one place to another and/or from one orientation to another.

In the present disclosure, 'constraining' of motion of Goldmann tonometer and/or the slit-lamp device away from the bed may refer to (i) the case where the motion is prevented altogether immobilizing the Goldmann tonometer and/or the slit-lamp device altogether (i.e. in absolute terms or relative to bed 610) and/or (ii) where there is not necessarily 'complete prevention' of the motion of the Goldmann tonometer and/or the slit-lamp device away from the bed—in this case, the motion of the Goldmann tonometer and/or the slit-lamp device away from the bed is met with a counterforce form bed—i.e. so that bed 610 is 'dragged along' with the Goldmann tonometer and/or the slit-lamp device according to the motion away from the bed.

The 'motion away' is motion which, if it were not for the prevention of the counterforce would cause the Goldmann tonometer and/or the slit-lamp device to move away from the bed—there is no requirement for the distance between the Goldmann tonometer and/or the slit-lamp device and the bed to either increase or to be altogether prevented from increasing.

Pivot Axis

In some embodiments, motion of the Goldmann tonometer and/or the slit-lamp device may be constrained to a rotational motion around a pivot axis.

Figure 29A:
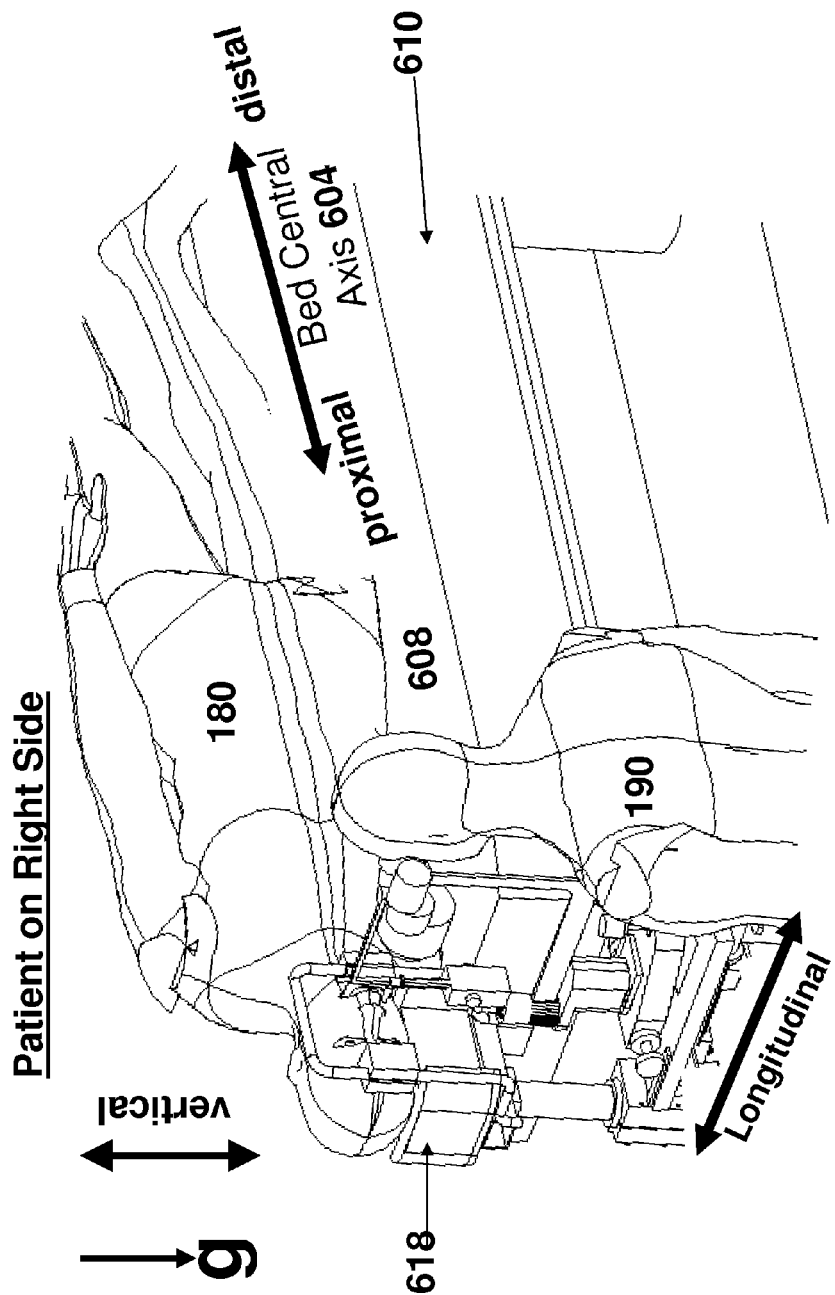
Figure 29B:
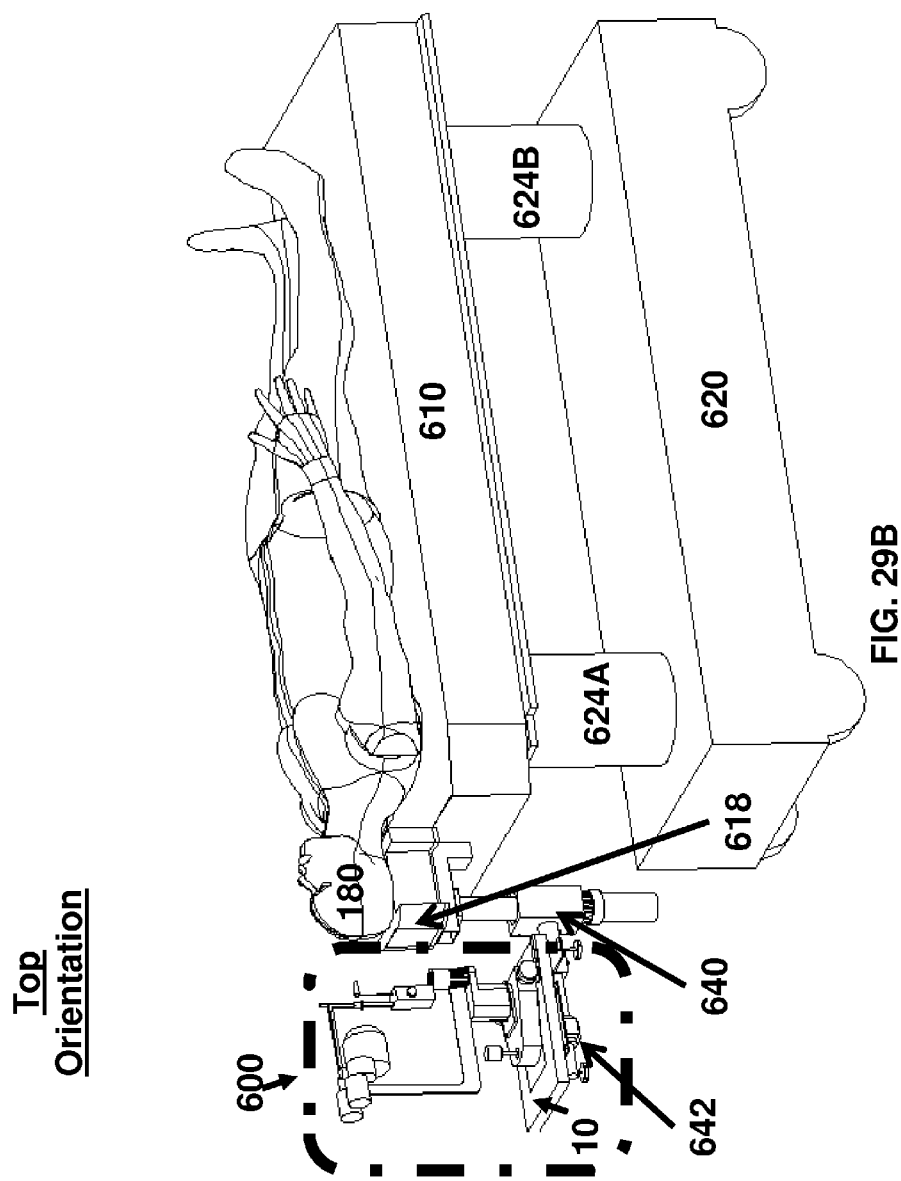
Figure 30A:
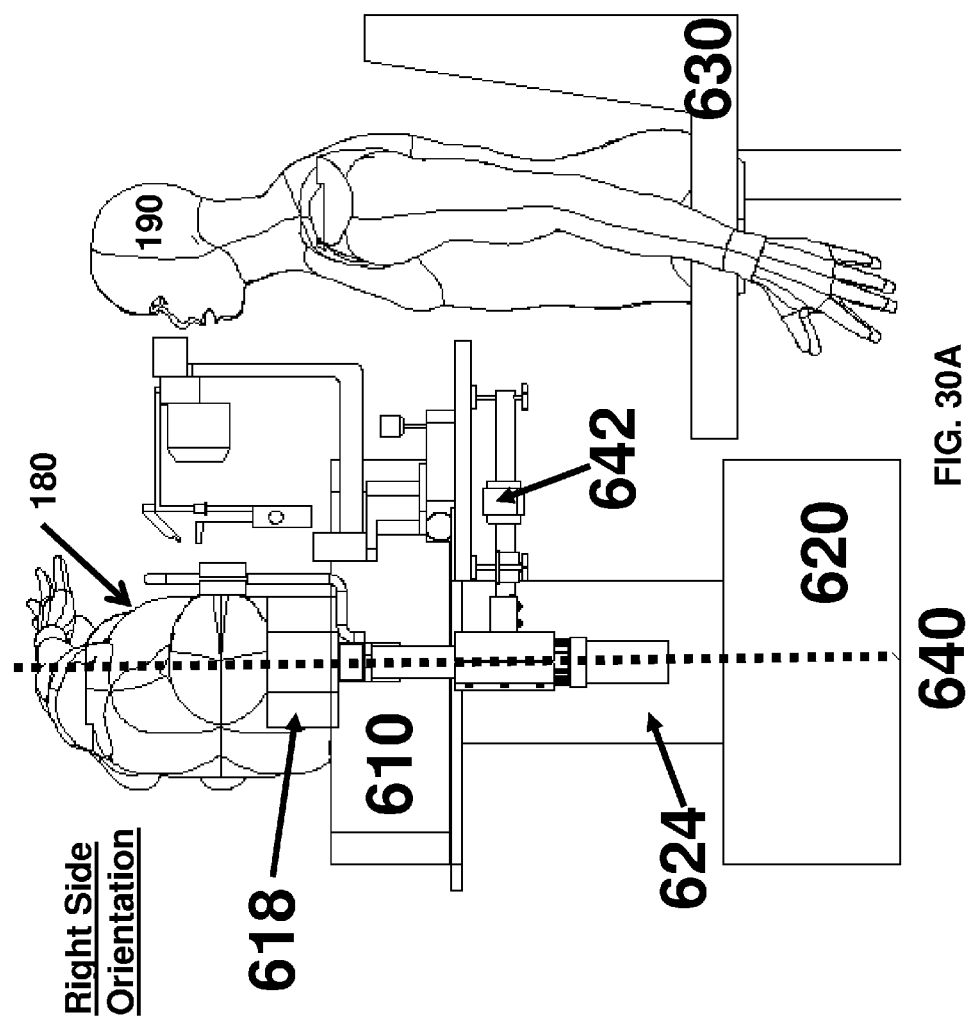
Figure 30B:
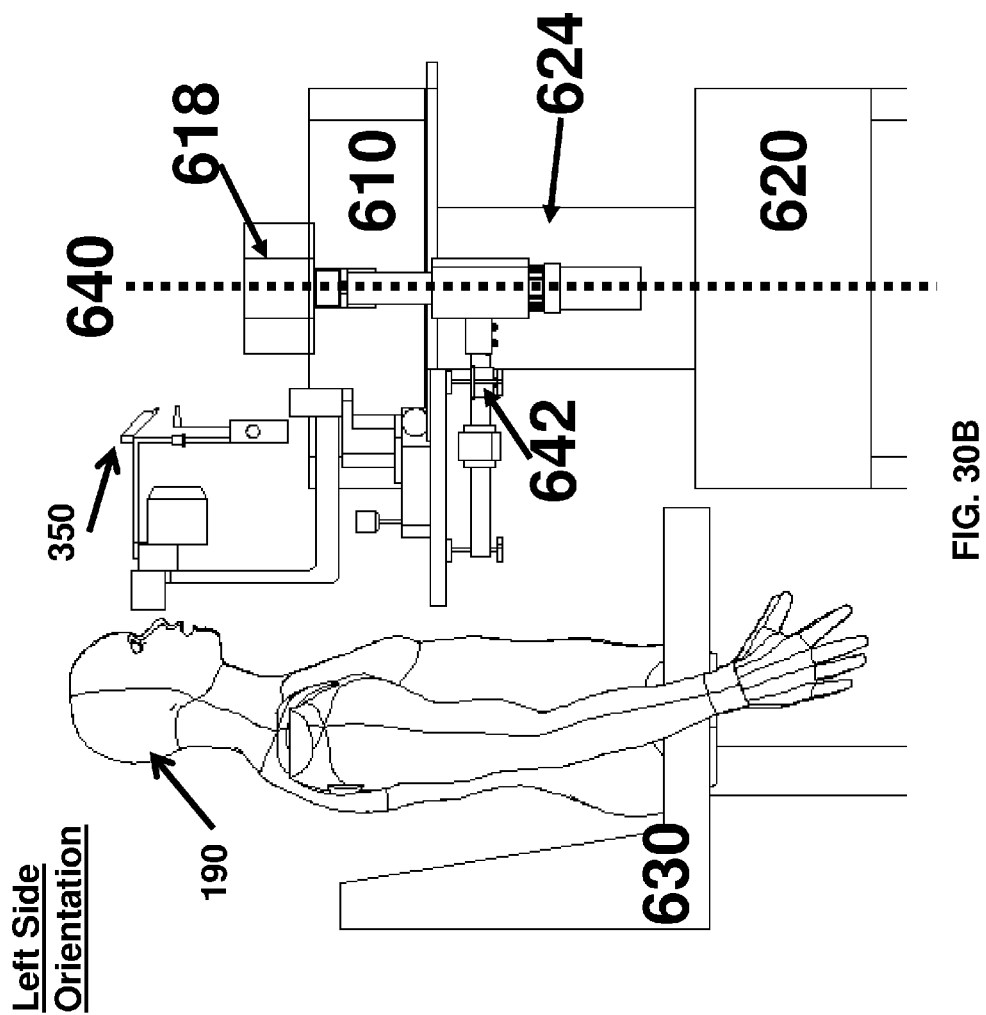

In the example of FIG. 29-30, the slit lamp device and/or Goldmann tonometer device may literally rotate around axis 640—for example, slit lamp and/or Goldmann tonometer device is mounted to or connected to bed assembly via mounting arm 642 which may 'hang below' an upper portion of bed 610 and/or may be directly or indirectly attached to bed assembly in any other manner.

Figure 31A:
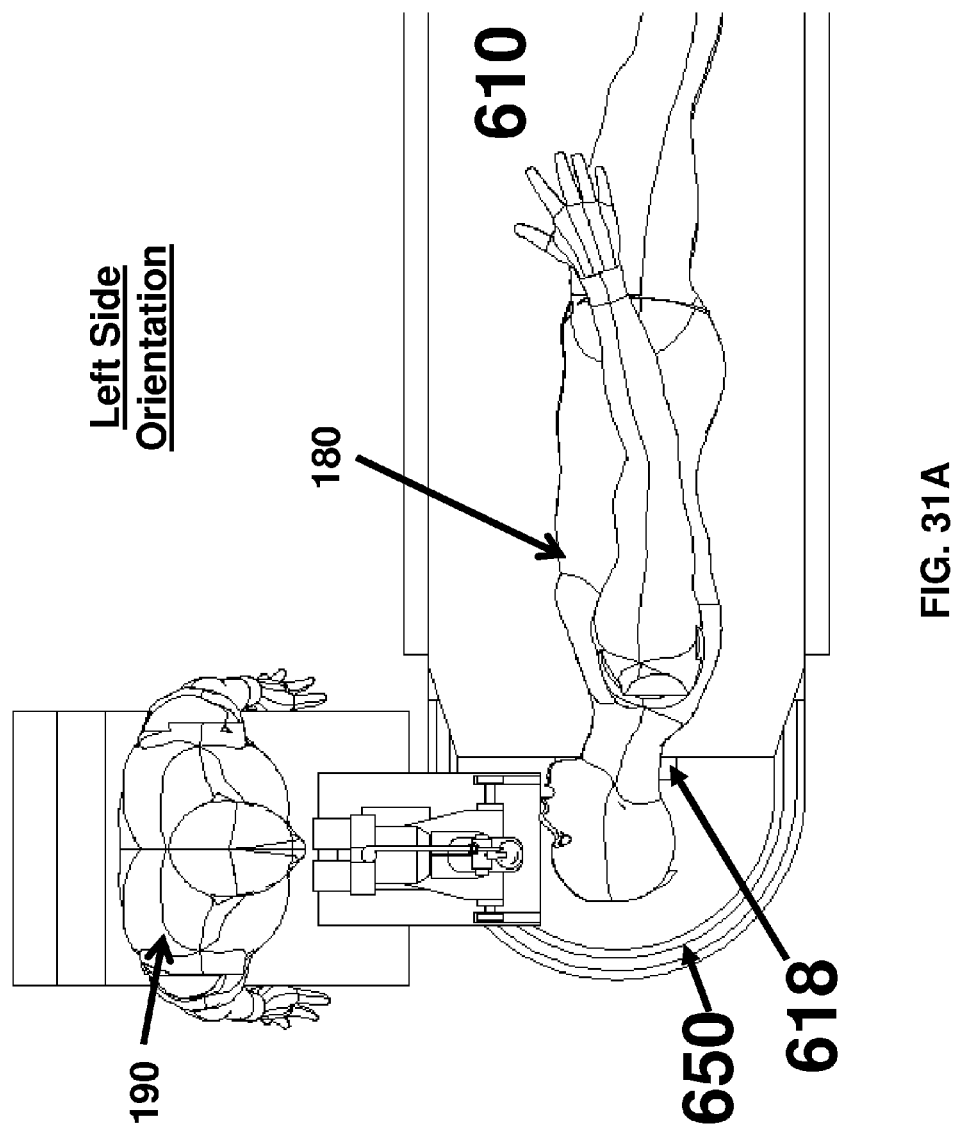
Figure 31B:
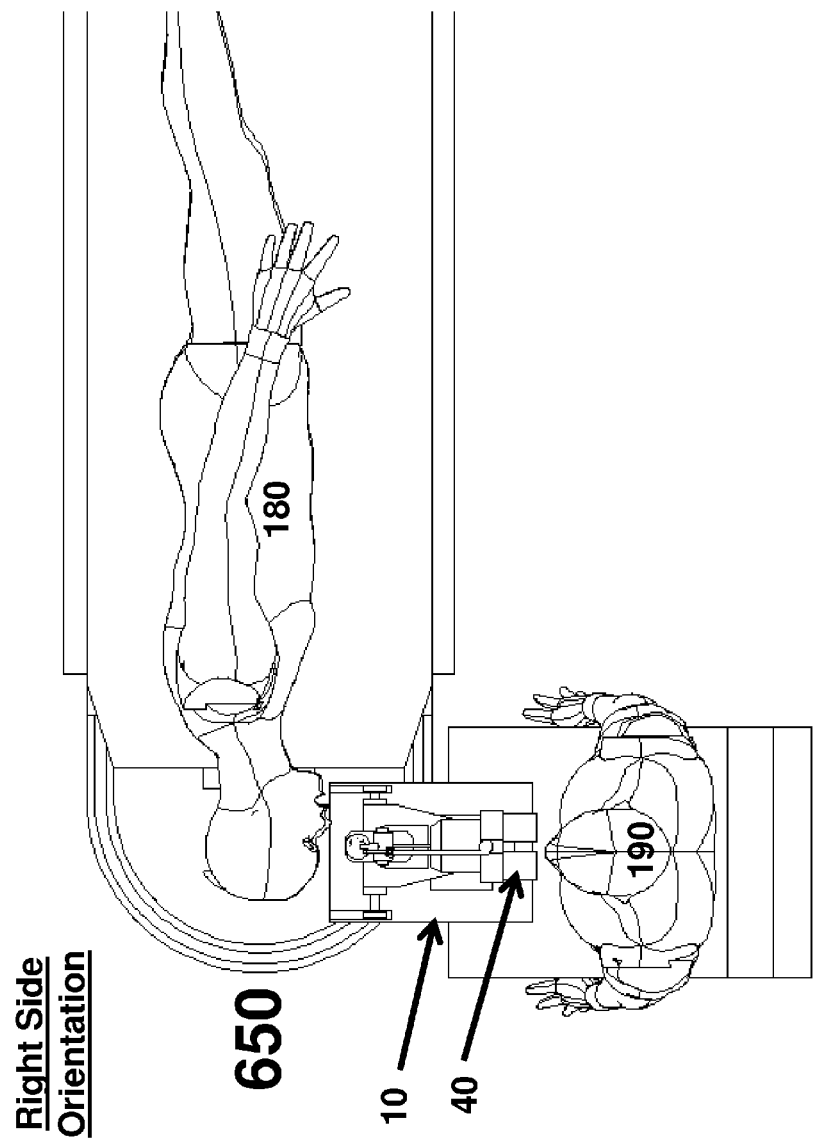

In another non-limiting example, rather than have the Goldmann tonometry and/or slit lamp device pivot, it is possible to mount slit lamp apparatus onto a track 650 via vertical mounting element 654 so that slit lamp apparatus 600 may slide along track 650—also see FIG. 31.

Goldmann Tonometry Device Lacking an Illumination Column

Figure 32B:
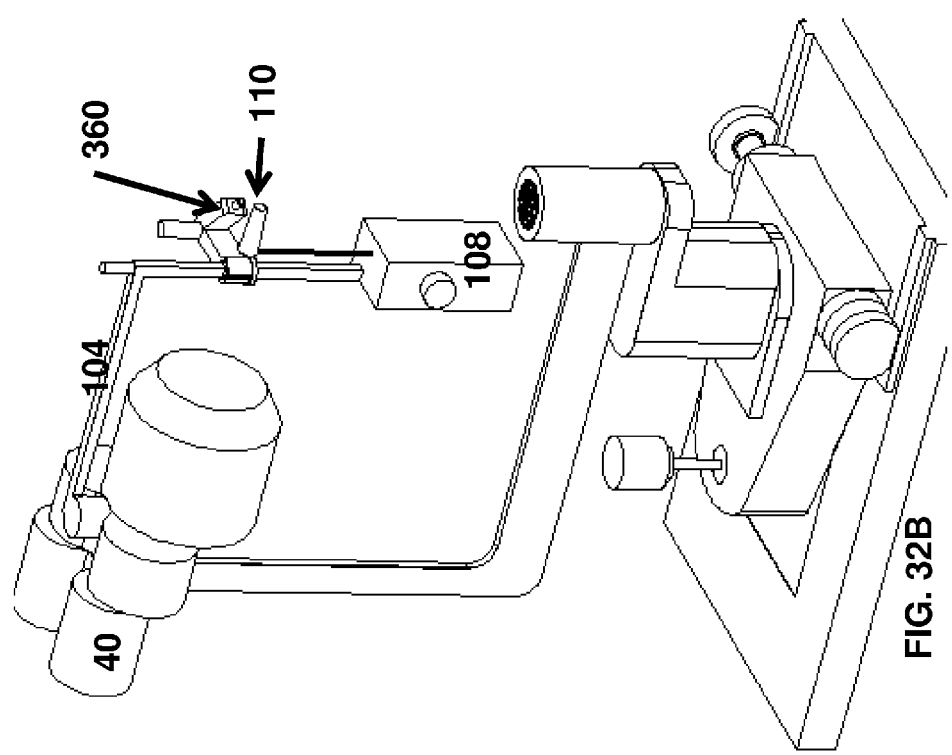

In some embodiments, a source of illumination such as 350 of FIG. 32A or 360 of FIG. 32B emits a beam of light to tonometry probe (for example, to a location at or near a distal end of the probe 10). This may obviate the need for an illumination column. In some embodiments, the light is blue such as cobalt blue.

Additional Discussion

In some embodiments, any combination of the following features may be provided for any apparatus and/or method disclosed herein:

(i) Some embodiments relate to a Goldmann tonometry device that is mechanically coupled to and/or attached to a 'bed assembly' including a bed upper surface 608 configured to support a human adult (or majority thereof) body. In one example, a smaller 'protruding head rest' 618 is attached to a larger bed 610, and the patient 180 can rest his/her head on the head rest 618 during tonometry measurements (see FIGS. 16, 20 and other figures). In one example, the bed is supported on a wheeled chassis such that motion of the bed chassis cause the Goldmann tonometry device to 'follow' the bed chassis. In one example, motion of the tonometry device relative to the bed is constrained to rotational motion around a pivot axis 640 at or near one end of the bed (in one example, wheels of bed 610 are illustrated at the bottom of FIG. 19);

(ii) Some embodiments relate to a Goldmann tonometry device that is mechanically coupled to and/or attached to a headrest 618 whose length is at least 20 cm and/or at least 25 cm and/or at least 30 cm whose 'width' of headrest is at least 10 cm and/or at least 15 cm and/or at least 20 cm—i.e. enough to accommodate and vertically immobilize a side of a patient's head. The headrest may be (see, for example FIG. 25) rigidly attached to a lower base 10 (e.g. to a frame of and/or a surface and/or any portion of the base) so that the lower base 10 can 'pull' the headrest 618. The headrest has a length (e.g. at least 22.5 cm or at least 25 cm or at least 30 cm) that can vertically immobilize and orientationally-immobilize most adult human heads and also has a 'significant surface area' (e.g. at least 200 cm^2) and/or a significant 'depth' in a direction perpendicular to the length.

(iii) Some embodiments relate to a face immobilization assembly 662 configured to 'frame' a human face or head (i.e. in cooperation with an upper surface 658 of headrest 618) to 'horizontally immobilize the human face or head.' The face immobilization assembly includes (see, e.g. FIG. 22) a plurality of vertical elements—for example, chinrest 312 and forehead rest 314) for this purpose and/or for preventing horizontal motion of a face to which a chin and/or forehead is engaged. In some embodiments, the chinrest and/or forehead rest 314 are constructed of some sort of rigid 'core' to which an outer softer and/or pliable layer of materials is applied. Alternatively or additionally, 'sideward depression' (i.e. pointing substantially horizontally) on a rigid vertical element may be provided at a location where the patient 180 rests his/her chin and/or forehead. The face immobilization assembly 662 may be attached to a tonometer base 10 and/or to a headrest 618 and/or to a bed 610. In some embodiments, a height of the vertical elements (and a height of the 'frame region') is at least 7 cm and/or at least 10 cm.

In some embodiments (see FIG. 22), a headrest includes two 'modes' or 'configurations'—a first mode when the face immobilization assembly is mounted to and/or attached to a first side of the headrest and a second mode when the face immobilization assembly is mounted to and/or attached to a second side of the headrest 618.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to. The term "or" is used herein to mean, and is used interchangeably with, the term "and/or," unless context clearly indicates otherwise. The term "such as" is used herein to mean, and is used interchangeably with, the phrase "such as but not limited to".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A system for performing an eye examination on a patient, the system comprising:
   a. a horizontal-orientation-constrained applanation tonometer probe having a thicker proximal end and a thinner distal end;
   b. a microscope assembly configured to receive light so that a location in contact with a distal end of the tonometer probe is in a field of view of the microscope assembly;

c. a lower base;
d. an upper base movable over the lower base to provide in-tandem horizontal motion of the upper base and the tonometer probe over the lower base,
e. an elevated headrest configured to be held at a constant orientation and position relative to the lower base, an elevation of an upper surface of the head rest exceeding an elevation of a flat surface of the lower base over which the upper base is configured to move by at least 5 cm, the elevated head rest having a length that exceeds 10 cm and a width that exceeds 10 cm;
f. a face immobilization assembly including first and second vertical elements connected to each other via an upper horizontal element, the face immobilization assembly, in combination with the upper surface of the headrest and/or a planar extension of the upper surface of the headrest, configured to frame a region of space such that:
  (i) an elevation of the framed region of space exceeds an elevation of the upper surface of the headrest;
  (ii) a horizontal location of the entire framed region of space is less than 5 cm from the upper surface of the headrest;
  (iii) a height of the framed region of space is at least 8 cm; and
  (iv) a length of the framed region of space is at least 20 cm; and
g. a motion controller assembly comprising one or more motion controllers, at least one of the one or more motion controllers being a joystick, the motion controller assembly being configured:
  (i) to induce the in-tandem horizontal motion of the upper base and the tonometer probe over the lower base; and
  (ii) to induce vertical motion of the tonometer probe relative to the lower base and relative to the upper surface of the headrest,
wherein the headrest and the face immobilization assembly are configured to immobilize a head of the patient while the patient's head is positioned laterally for at least a duration of an eye examination.

2. The system of claim 1 wherein the lower base is mounted onto a wheeled chassis, the wheeled chassis being configured for horizontal motion that causes horizontal motion of the headrest.

3. The system of claim 1 wherein the lower base is part of a wheeled chassis, the wheeled chassis being configured for horizontal motion that causes horizontal motion of the headrest.

4. The system of claim 1 wherein the lower base supports the headrest.

5. The system of claim 1 wherein the lower base supports the face immobilization assembly.

6. The system of claim 1 wherein the joystick is mounted onto the movable upper base.

7. The system of claim 1 further comprising a source of illumination configured to emit a beam of light to the distal end of the tonometry probe.

8. The system of claim 1 wherein the microscope assembly comprises a slit lamp.

9. The system of claim 1 wherein the motion controller assembly is configured (i) to induce the in-tandem horizontal motion of the upper base and the tonometer probe over the lower base; and (ii) to induce vertical motion of the tonometer probe relative to the lower base and relative to the upper surface of the headrest, such that a range of a distal end of the tonometry probe includes a location within the framed region of space.

10. The system of claim 1 wherein the motion controller assembly is configured (i) to induce the in-tandem horizontal motion of the upper base and the tonometer probe over the lower base; and (ii) to induce vertical motion of the tonometer probe relative to the lower base and relative to the upper surface of the headrest, such that a range of a distal end of the tonometry probe includes a location that is (A) within the framed region of space and (B) horizontally displaced from the elevated head rest by no more than 2 cm.

* * * * *